(12) United States Patent
Roper

(10) Patent No.: US 9,028,837 B2
(45) Date of Patent: May 12, 2015

(54) METHODS AND COMPOSITIONS FOR POXVIRUS A35R PROTEIN

(71) Applicant: East Carolina University, Greenville, NC (

METHODS AND COMPOSITIONS FOR POXVIRUS A35R PROTEIN

STATEMENT OF PRIORITY

This application is a divisional application of, and claims priority to, U.S. patent application Ser. No. 13/491,356, filed on Jun. 7, 2012, which is a divisional application of, and claims priority to, U.S. patent application Ser. No. 12/281,099, filed on Aug. 28, 2008 and issued as U.S. Pat. No. 8,202,521 on Jun. 19, 2012, which is a 35 U.S.C. §371 national phase application of PCT International Application No. PCT/US2006/007393, filed on Mar. 1, 2006, the entire contents of each of which are incorporated by reference herein.

FIELD OF THE INVENTION

The present invention relates to poxvirus A35R protein, antibodies thereto, and nucleic acids encoding the A35R protein and their use in diagnostic and therapeutic methods.

BACKGROUND ART

Poxviruses are large double-stranded DNA viruses with genomes that range from 130 to 379 kbp. Poxviruses have worldwide distribution and infect a wide variety of animals, including insects, birds and mammals. Since the eradication of smallpox and the cessation of vaccination programs, various poxvirus infections have begun to re-emerge clinically worldwide. Variola virus continues to present a bioterrorism threat and several other poxviruses infect humans, causing morbidity and mortality: molluscum contagiosum virus (MCV), monkeypox virus, Tanapox virus, Yaba-like disease virus, cowpox virus and Cantagalo virus (evolved from a vaccinia virus (VV) vaccine strain). The prevalence of poxviruses in animals and humans and their propensity for recombination and gene acquisition suggest that it would be unwise to discount them as important human pathogens. This is especially true, since most emerging infectious diseases are zoonoses, crossing from animals to humans, and poxviruses are known to acquire mutations and become highly pathogenic in a new animal species.

The A35R gene is highly conserved in mammalian-tropic poxviruses. VV is the model poxvirus to study the A35R protein (called A35R in Copenhagen strain, 0158 in WR strain and a number of other designations in all mammalian-tropic poxviruses) and its role in the virus life cycle. The present invention provides the discovery that the A35R protein has immunoregulatory activity. Thus, the present invention overcomes previous shortcomings in the art by providing an A35R protein and biologically active fragments thereof, as well as nucleic acids encoding this protein and its fragments and antibodies and inhibitors specific thereto. These compositions are used, for example, in methods of diagnosing, treating and preventing infection by poxvirus, treating and preventing other disorders and in modulating immune responses.

SUMMARY OF THE INVENTION

The present invention provides a method of modulating an immune response in a subject, comprising administering to the subject an immunomodulating amount of an A35R protein or active fragment thereof of vaccinia virus or other poxvirus and/or administering an immunomodulating amount of a nucleic acid encoding an A35R protein or active fragment thereof of vaccinia virus or other poxvirus.

Further provided herein is a method of treating or preventing an autoimmune disorder in a subject, comprising administering to the subject an effective amount of an A35R protein or active fragment thereof of vaccinia virus or other poxvirus and/or administering an effective amount of a nucleic acid encoding an A35R protein or active fragment thereof of vaccinia virus or other poxvirus.

In addition, the present invention provides a method of reducing the likelihood of transplant rejection in a transplant recipient, comprising administering to the subject an effective amount of an A35R protein or active fragment thereof of vaccinia virus or other poxvirus and/or administering an effective amount of a nucleic acid encoding an A35R protein or active fragment thereof of vaccinia virus or other poxvirus.

Also included is a method of enhancing an immune response to a poxvirus vaccine in a subject, comprising administering to the subject an immunogenic amount of a poxvirus vaccine engineered to lack nucleic acid encoding an A35R protein and/or to lack A35R protein activity.

In additional embodiments, the present invention provides a method of enhancing an immune response in a subject to a heterologous antigen encoded by a poxvirus vector, comprising administering to the subject an immunogenic amount of a poxvirus vector comprising nucleic acid encoding the antigen and wherein the poxvirus vector is engineered to lack nucleic acid encoding an A35R protein and/or to lack A35R protein activity.

Furthermore, the present invention provides a method of treating or preventing a detrimental immune response in a subject, comprising administering to the subject an effective amount of an A35R protein or active fragment thereof of vaccinia virus or other poxvirus protein and/or administering an effective amount of a nucleic acid encoding an A35R protein or active fragment thereof of vaccinia virus or other poxvirus.

A method is also provided herein of treating or preventing a detrimental immune response in a subject wherein the detrimental immune response is caused by A35R protein activity, comprising administering to the subject an effective amount of a substance that inhibits A35R protein activity.

The present invention further provides a method of enhancing an immunomodulating effect of a substance, comprising combining the substance with an A35R protein or active fragment thereof of vaccinia virus or other poxvirus and/or combining the substance with a nucleic acid encoding an A35R protein or active fragment thereof of vaccinia virus or other poxvirus.

Additionally provided herein is a method of treating or preventing a poxvirus infection in a subject, comprising administering to the subject an effective amount of an inhibitor of A35R protein activity.

Further embodiments of this invention include a method of diagnosing a poxvirus infection in a subject, comprising: a) contacting a sample from the subject with an antibody that specifically binds A35R protein under conditions whereby an antigen/antibody complex can form; and b) detecting formation of the antigen/antibody complex, thereby diagnosing poxvirus infection in a subject.

Also provided herein is a method of diagnosing poxvirus infection in a subject, comprising: a) contacting a sample from the subject with an A35R protein or antigenic fragment thereof under conditions whereby an antigen/antibody complex can form; and b) detecting formation of the antigen/antibody complex, thereby diagnosing poxvirus infection in a subject.

A method is also provided herein of detecting poxvirus in a sample, comprising: a) contacting the sample with an antibody that specifically binds A35R protein under conditions whereby an antigen/antibody complex can form; and b) detecting formation of the antigen/antibody complex, thereby detecting poxvirus in the sample.

Further provided herein is a method of detecting an antibody to poxvirus in a sample, comprising: a) contacting the sample with an A35R protein or antigenic fragment thereof under conditions whereby an antigen/antibody complex can form; and b) detecting formation of the antigen/antibody complex, thereby detecting an antibody to poxvirus in the sample.

In addition, the present invention provides a method of identifying nucleic acid comprising a nucleotide sequence encoding A35R protein in a sample, comprising: a) contacting the sample with an oligonucleotide comprising a nucleotide sequence that is complementary to the nucleotide sequence encoding A35R protein, under conditions whereby nucleic acid hybridization can occur; and b) detecting nucleic acid hybridization, thereby detecting nucleic acid comprising the nucleotide sequence encoding A35R protein in the sample.

Additional embodiments include a method of identifying nucleic acid comprising a nucleotide sequence encoding A35R protein in a sample, comprising: a) contacting the sample with a pair of oligonucleotide primers that are complementary to the nucleotide sequence encoding A35R protein, under conditions whereby nucleic acid amplification can occur; and b) detecting nucleic acid amplification, thereby detecting nucleic acid comprising the nucleotide sequence encoding A35R protein in the sample.

The present invention additionally provides a method of treating cancer in a subject, comprising administering to the subject a poxvirus engineered to lack A35R protein activity and in some embodiments, the poxvirus can further comprise: a) nucleic acid encoding a costimulatory molecule (e.g., B7.1, ICAM-1, LFA-3); b) nucleic acid encoding a tumor antigen; and/or c) nucleic acid encoding an immunomodulatory protein, in any combination.

In other embodiments, the present invention provides a composition comprising A35R protein and a pharmaceutically acceptable carrier and a composition comprising a poxvirus engineered to lack A35R activity and a pharmaceutically acceptable carrier and a composition consisting essentially of a nucleotide sequence encoding a poxvirus A35R protein and a pharmaceutically acceptable carrier.

Various other objectives and advantages of the present invention will become apparent from the following detailed description.

DETAILED DESCRIPTION OF THE INVENTION

The present invention is based on the unexpected discovery that the A35R protein of poxvirus has immunomodulating activity. Thus, in one embodiment, the present invention provides a method of modulating an immune response in a subject, comprising administering to the subject an effective amount of an A35R protein or active fragment thereof of vaccinia virus or other poxvirus and/or administering to the subject an effective amount of a nucleic acid encoding an A35R protein or active fragment thereof of vaccinia virus or other poxvirus.

Further provided in this invention is a method of treating and/or preventing an autoimmune disorder in a subject, comprising administering to the subject an effective amount of an A35R protein or active fragment thereof of vaccinia virus or other poxvirus and/or administering an effective amount of a nucleic acid encoding an A35R protein or active fragment thereof of a vaccinia virus or other poxvirus. Nonlimiting examples of autoimmune disorders that can be treated and/or prevented by the methods of this invention include arthritis (e.g., rheumatoid arthritis or RA), multiple sclerosis (MS), diabetes (e.g., insulin dependent diabetes mellitus or IDDM), systemic lupus erythematosus (SLE), myasthenia gravis, Crohns' disease, regional enteritis, vasculitis, ulcerative colitis, Sjogren's syndrome, ankylosing spondylitis, polymyositis and any other autoimmune disorder now known or later identified. The methods of the present invention can further be employed to treat allergies, allergic reactions, and any other disease or disorder associated with an aberrant and/or undesirable immune response or reaction.

Additionally provided is a method of reducing the likelihood of transplant rejection (or increasing the likelihood of successful transplantation) in a transplant recipient, comprising administering to the transplant recipient an effective amount of an A35R protein or active fragment thereof of vaccinia virus or other poxvirus and/or administering to the transplant recipient an effective amount of a nucleic acid encoding an A35R protein or active fragment thereof of vaccinia virus or other poxvirus. The reduction in the likelihood of transplant rejection or increase in the likelihood of successful transplantation is in comparison to the likelihood of transplant rejection or likelihood of successful transplantation in a transplant recipient that did not receive an A35R protein or active fragment thereof or a nucleic acid encoding an A35R protein or active fragment thereof, as such likelihoods would be know and/or determined according to art-known standards. Furthermore, the protein, active fragment and/or nucleic acid of these methods can be administered to the transplant recipient at any time relative to the transplantation (i.e., before, after and/or simultaneously, in any combination.

In additional embodiments of this invention, a method is provided of enhancing an immune response to a poxvirus vaccine in a subject, comprising administering to the subject an immunogenic amount of a poxvirus vaccine engineered to lack nucleic acid encoding an A35R protein and/or to lack A35R protein activity. Thus, the poxvirus used in the vaccine can have a complete or partial deletion of the nucleotide sequence encoding the A35R protein or the poxvirus of the vaccine can have an alteration in the nucleotide sequence encoding the A35R protein (e.g., a deletion, substitution, insertion, stop codon, missense mutation, nonsense mutation, or any other mutation), the end result being a lack of A35R protein activity in a cell or subject to which the poxvirus vaccine has been delivered or introduced. Nonlimiting examples of poxviruses that can be altered according to the methods of this invention to lack A35R protein activity are the attenuated Modified Vaccinia Ankara (MVA) vaccine, the DRYVAX vaccine, the Acambis vaccines (ACM1000 and ACM2000), as well as any other poxvirus vaccine now known or later identified.

Also provided herein is a method of enhancing an immune response in a subject to a heterologous antigen encoded by a poxvirus vector, comprising administering to the subject an immunogenic amount of a poxvirus vector comprising nucleic acid encoding the antigen and wherein the poxvirus vector is engineered to lack nucleic acid encoding an A35R protein and/or to lack A35R protein activity. As noted above, the poxvirus used in the vaccine can have a complete or partial deletion of the nucleotide sequence encoding the A35R protein or the poxvirus of the vaccine can have an alteration in the nucleotide sequence encoding the A35R protein (e.g., a deletion, substitution, insertion, top codon, missense mutation, nonsense mutation, or any other mutation), the end result being a lack of A35R protein activity in a cell or subject to which the poxvirus vaccine has been delivered or introduced. The use of poxviruses as vectors to deliver antigens for vaccine is known in the art. Nonlimiting examples of such vectors include those described for rabies vaccines in Rupprecht et al. (*Virus Research* 111:101-105 (2005)); HW vaccines in Cebere et al. (*Vaccine* 24:417-425 (2006)); tuberculosis vaccines in Xing et al. (*Curr. Gene Ther.* 5:485-482 (2005)); and for cancer immunotherapies in Kaufman et al. (*Curr. Gene Ther.* 17:239-244 (2006)).

In the methods provided herein for enhancing an immune response, such an enhancement is identified by comparison with an immune response in a subject that did not receive the protein, active fragment and/or nucleic acid of this invention. Such comparative studies can be carried out according to well known protocols in the art for detecting and/or measuring any number of immune responses. Nonlimiting examples of an immune response that can be enhanced by the methods of this invention include antibody response (e.g., protective antibody response; neutralizing antibody response), cytotoxic T cell response, T helper response, interleukin-2 (LL-2) production; and vaccine efficacy.

Further provided herein is a method of treating or preventing a detrimental immune response in a subject, comprising administering to the subject an effective amount of an A35R protein or active fragment thereof of vaccinia virus or other poxvirus protein and/or an effective amount of a nucleic acid encoding an A35R protein or active fragment thereof of a vaccinia virus or other poxvirus.

Also provided herein is a method of treating or preventing a detrimental immune response in a subject wherein the detrimental immune response is caused by A35R protein activity, comprising administering to the subject an effective amount of a substance that inhibits A35R protein activity. A substance that inhibits A35R activity, can be, but is not limited to a ligand (e.g., an antibody or antibody fragment) that specifically binds an A35R protein or active fragment thereof and/or a nucleic acid that inhibits transcription or translation of nucleic acid encoding an A35R protein or active fragment thereof (e.g., an antisense nucleic acid that binds a coding sequence of the A35R protein, an interfering RNA that inhibits or suppresses transcription and/or translation of the A35R protein, a ribozyme, etc.) Furthermore, small molecules and other compounds and substances that inhibit the activity of A35R could be used in the methods of this invention.

A detrimental immune response as described herein can be, for example, a detrimental immune response produced by an agent comprising the A35R protein or nucleic acid encoding the A35R protein. Examples of a detrimental immune response include but are not limited to allergic reaction or allergy, immune-mediated inflammation of the organs (e.g., heart; central nervous system; kidney; liver), pathogen-induced immunopathology, autoimmune diseases and disorders (e.g., diabetes, SLE, MS), etc.

In other embodiments of this invention, the detrimental immune response can be an immune response produced by a bioterrorism agent (e.g., an immune response that is harmful to a subject that can be modulated by delivery to the subject of the A35R protein or active fragment thereof and/or nucleic acid of this invention). Examples of such bioterrorism agents include but are not limited to infectious biological agents such as pathogenic bacteria (e.g., *Yersinia* causing plague; *Bacillus anthracis* causing anthrax; *Francisella tularensis*), viruses (e.g., influenza; SARS coronavirus; Ebola virus; Marburg virus;), toxins, etc., as well as any other agent now known or later identified that can be used as a bioterrorism agent.

In yet other embodiments, the detrimental immune response can be produced by the presence, either naturally or unnaturally, in the bioterrorism agent, of the A35R protein or active fragment thereof or a nucleic acid encoding the A35R protein or active fragment thereof. In such embodiments, the detrimental immune response is treated by delivery to the subject of a substance as described herein that inhibits or reduces A35R protein activity. Examples of such bioterrorism agents can include smallpox, vectors comprising A35R activity and other infectious agents and toxic agents as described herein that are engineered to have A35R activity.

In yet further embodiments of this invention, a method is provided of enhancing an immunomodulating effect of a substance, comprising combining the substance with an A35R protein or active fragment thereof of vaccinia virus or other poxvirus and/or combining the substance with a nucleic acid encoding an A35R protein or active fragment thereof. Such a substance that has an immunomodulating effect can be but is not limited to steroids, immunosuppressive drugs, interferons, corticosteroids, azathioprine, cyclophosphamide, prednisone, methotrexate, rituximab, etc., as well as any other immunomodulating agent now known or later identified.

An enhancement of an immunomodulating effect of a substance would be identified by comparison of an immunomodulating effect of the substance in a subject with and without the presence of the A35R protein or active fragment thereof or nucleic acid encoding the A35R protein or active fragment thereof. As used herein, an "immunomodulating effect" is any action or activity of a cell or tissue of the immune system. Such an immunomodulating effect can be positive or negative, an enhancement or an inhibition, an increase or a decrease in a response, activity and/or reaction. Ways to detect and/or measure an immunomodulating effect are known in the art and include standard protocols such as those used to detect and/or measure antibody production or activity, T lymphocyte proliferation or activity, cytotoxicity and/or cytokine production or activity.

The present invention additionally provides a method of treating or preventing a poxvirus infection in a subject, comprising administering to the subject an effective amount of an inhibitor of A35R protein activity. As noted above, a substance that inhibits A35R activity, can be, but is not limited to a ligand, an antibody or an antibody fragment that specifically binds an A35R protein or active fragment thereof, a nucleic acid that inhibits transcription or translation of nucleic acid encoding an A35R protein or active fragment thereof and/or a drug or other substance that acts to inhibit A35R activity (e.g., immunosuppressive drugs, steroids, interferon, etc.)

The method of treating or preventing infection caused by poxvirus in a subject can be carried out, for example, by contacting an immune cell of the subject with any of the polypeptides, fragments, nucleic acids, vectors and/or antibodies of this invention. The cell can be, for example, a CD8$^+$ T cell which is contacted with the polypeptide and/or fragment of this invention in the presence of a class I MHC molecule, which can be a soluble molecule or it can be present on the surface of a cell which expresses class I MHC molecules. The cell can also be any cell that can take up and express exogenous nucleic acid and produce the polypeptides and/or fragments of this invention. In some embodiments, the polypeptides and/or fragments of this invention can be produced by a cell that secretes them, whereby the polypeptide and/or fragment is produced and secreted and then taken up and subsequently processed by an antigen presenting cell or other class I MHC-expressing cell and presented to the immune system for induction of an immune response. In other embodiments, the nucleic acids and/or vectors of this invention can be directly introduced into an antigen presenting cell and/or other class I MHC-expressing cell in which the polypeptide and/or fragment is produced and processed directly and presented to the immune system on the cell surface.

As set forth above, it is contemplated that in the methods wherein the compositions of this invention are administered to a subject or to a cell of a subject, such methods can further comprise the step of administering a suitable adjuvant to the subject or to a cell of the subject. The adjuvant can be in the composition of this invention or the adjuvant can be in a separate composition comprising the suitable adjuvant and a pharmaceutically acceptable carrier. The adjuvant can be administered prior to, simultaneous with, and/or after administration of the composition containing any of the polypeptides, fragments, nucleic acids and/or vectors of this invention. For example, QS-21, similar to alum, complete Freund's adjuvant, SAF, etc., can be administered within days/weeks/hours (before or after) of administration of the composition of this invention. The effectiveness of an adjuvant can be determined by measuring the immune response directed against the polypeptide and/or fragment of this invention with and without the adjuvant, using standard procedures, as described herein and as are well known in the art.

The subject of this invention can be any subject in need of the immune response of this invention and/or in need of treatment for or prevention from poxvirus infection, as well as any subject in whom it is desirable to induce an immune response to poxvirus. Such a subject can be any type of animal that is susceptible to infection by a poxvirus of this invention, as well as any animal to which the proteins, active fragments thereof and nucleic acids of this invention can be administered according to the methods of this invention. For example, an animal of this invention can be a mammal, a bird or a reptile. In certain embodiments, the subject of this invention is a human.

Symptoms of poxvirus infection can include fever, headache, muscle and/or joint aches, fever, rash, inflammation, etc. Appropriate treatment can lead to a reduction in the severity of and/or elimination of one or more of these symptoms.

The compositions of this invention can be administered to a cell of a subject or to a subject either in vivo or ex vivo. For administration to a cell of the subject in vivo, as well as for administration to the subject, the compositions of this invention can be administered orally, parenterally (e.g., intravenously), by intramuscular injection, by intraperitoneal injection, subcutaneous injection, transdermally, extracorporeally, topically or the like. Also, the compositions of this invention can be pulsed onto dendritic cells, which are isolated or grown from a subject's cells, according to methods well known in the art, or onto bulk peripheral blood mononuclear cells (PBMC) or various cell subfractions thereof from a subject.

The exact amount of the composition required will vary from subject to subject, depending on the species, age, weight and general condition of the subject, the particular composition used, its mode of administration and the like. Thus, it is not possible to specify an exact amount for every composition of this invention. However, effective amount can be determined by one of ordinary skill in the art using only routine experimentation given the teachings herein.

As an example, to a subject diagnosed with poxvirus infection or known to be at risk of being infected with poxvirus or in whom it is desirable to induce an immune response to poxvirus, between about 0.1 µg/kg to about 10 g/kg of a polypeptide and/or biologically active fragment of this invention can be administered subcutaneously and can be in an adjuvant, at hourly, daily and/or weekly intervals until an evaluation of the subject's clinical parameters indicate that the subject is recovered from infection by poxvirus and/or the subject demonstrates the desired immunological response. Alternatively, a polypeptide and/or fragment of this invention can be pulsed onto dendritic cells at a concentration of between about 0.1 ng to about 500 mg and the dendritic cells can be administered to the subject intravenously at the same time intervals. The treatment can be continued or resumed if the subject's clinical parameters indicate that poxvirus infection is present and can be maintained until the infection is no longer detected by these parameters and/or until the desired immunological response is achieved.

If ex vivo methods are employed, cells or tissues can be removed and maintained outside the subject's body according to standard protocols well known in the art. The polypeptides and/or biologically active fragments of this invention can be introduced into the cells via known mechanisms for uptake of polypeptides into cells (e.g., phagocytosis, pulsing onto class I MEC-expressing cells, liposomes, etc.). The cells can then be infused (e.g., in a pharmaceutically acceptable carrier) or transplanted back into the subject per standard methods for the cell or tissue type. Standard methods are known for transplantation or infusion of various cells into a subject.

The pharmaceutical compositions of this invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration are preferably presented as unit dose suppositories. These can be prepared by admixing the composition with one or more conventional solid carriers, such as for example, cocoa butter and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, Pharmaceutical Research 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The present invention further provides a medicament and the preparation thereof for use in treating and/or preventing the disease and disorders described herein by employing the same steps as described in the methods disclosed herein. Also provided herein is a medicament and the preparation thereof for use in modulating (enhancing, treating or preventing a detrimental immune response, inhibiting, etc.) an immune response according to the steps of the methods described herein. It is further contemplated that the methods, compositions and medicaments of this invention can be used for veterinary application as well as in applications involving humans.

Furthermore, the nucleic acids and vectors of this invention can be administered orally, intranasally, parenterally (e.g., intravenously), by intramuscular injection, by intraperitoneal injection, transdermally, extracorporeally, topically or the like. In the methods described herein which include the administration and uptake of exogenous DNA into the cells of a subject (i.e., gene transduction or transfection), the nucleic acids of the present invention can be in the form of naked DNA or the nucleic acids can be in a vector for delivering the nucleic acids to the cells for expression of the polypeptides and/or fragments of this invention. The vector can be a commercially available preparation or can be constructed in the laboratory according to methods well known in the art.

Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system, which can package a recombinant retroviral genome. The recombinant retrovirus can then be used to infect and thereby deliver to the infected cells nucleic acid encoding the polypeptide and/or fragment of this invention. The exact method of introducing the exogenous nucleic acid into mammalian cells is, of course, not limited to the use of retroviral vectors. Other techniques are widely available for this procedure including the use of adenoviral vectors, alphaviral vectors, adeno-associated viral (AAV) vectors, lentiviral vectors, pseudotyped retroviral vectors and vaccinia viral vectors, as well as any other viral vectors now known or developed in the future. Physical transduction techniques can also be used, such as liposome delivery and receptor-mediated and other endocytosis mechanisms. This invention can be used in conjunction with any of these or other commonly used gene transfer methods.

As one example, the nucleic acid of this invention is delivered to the cells of a subject in a vaccinia virus vector, the dosage for administration of vaccinia virus to humans can typically range from about $10^4$ to $10^9$ pfu per injection, but in some embodiments, can be as high as $10^{12}$, $10^{15}$ and/or $10^{20}$ pfu per injection.

As another example, if the nucleic acid of this invention is delivered to the cells of a subject in an adenovirus vector, the dosage for administration of adenovirus to humans can range from about $10^4$ to $10^9$ plaque forming units (pfu) per injection, but can be as high as $10^{12}$, $10^{15}$ and/or $10^{20}$ pfu per injection.

In some embodiments, a subject will receive a single injection of a viral vector comprising a nucleic acid of this invention. If additional injections are necessary, they can be repeated at daily/weekly/monthly intervals for an indefinite period and/or until the efficacy of the treatment has been established. As set forth herein, the efficacy of treatment can be determined by evaluating the symptoms and clinical parameters described herein and/or by detecting a desired immunological response.

The exact amount of the nucleic acid or vector required will vary from subject to subject, depending on the species, age, weight and general condition of the subject, the particular nucleic acid or vector used, its mode of administration and the like. Thus, it is not possible to specify an exact amount for every nucleic acid or vector. However, an appropriate amount can be determined by one of ordinary skill in the art using only routine experimentation given the teachings herein.

The present invention further provides a method of diagnosing a poxvirus infection in a subject, comprising: a) contacting a sample from the subject with an antibody that specifically binds an A35R protein under conditions whereby an antigen/antibody complex can form; and b) detecting formation of the antigen/antibody complex, thereby diagnosing poxvirus infection in a subject.

Also provided herein is a method of diagnosing poxvirus infection in a subject, comprising: a) contacting a sample from the subject with an A35R protein or antigenic fragment thereof under conditions whereby an antigen/antibody complex can form; and b) detecting formation of the antigen/antibody complex, thereby diagnosing poxvirus infection in a subject.

In other embodiments, a method is provided of detecting poxvirus in a sample, comprising: a) contacting the sample with an antibody that specifically binds A35R protein under conditions whereby an antigen/antibody complex can form; and b) detecting formation of the antigen/antibody complex, thereby detecting poxvirus in the sample.

Further provided is a method of detecting an antibody to poxvirus in a sample, comprising: a) contacting the sample with an A35R protein or antigenic fragment thereof under conditions whereby an antigen/antibody complex can form; and b) detecting formation of the antigen/antibody complex, thereby detecting an antibody to poxvirus in the sample.

The present invention provides a method of detecting a nucleic acid comprising a nucleotide sequence encoding A35R protein in a sample, comprising: a) contacting the sample with an oligonucleotide comprising a nucleotide sequence that is complementary to the nucleotide sequence encoding A35R protein, under conditions whereby nucleic acid hybridization can occur; and b) detecting nucleic acid hybridization, thereby detecting nucleic acid comprising the nucleotide sequence encoding A35R protein in the sample.

Additionally provided is a method of detecting nucleic acid comprising a nucleotide sequence encoding A35R protein in a sample, comprising: a) contacting the sample with a pair of oligonucleotide primers that are complementary to the nucleotide sequence encoding A35R protein, under conditions whereby nucleic acid amplification can occur; and b) detecting nucleic acid amplification, thereby detecting nucleic acid comprising the nucleotide sequence encoding A35R protein in the sample.

A sample of this invention can be any sample in which poxvirus proteins and/or nucleic acids can be present. For example, the sample can be a body fluid, cells or tissue, including but not limited to, blood, serum, plasma, saliva, sputum, broncheoalveolar lavage, urine, semen, joint fluid, cerebrospinal fluid and cells, fluids and/or tissue from all organs to which poxvirus antigens can disseminate including lung, liver, heart, brain, kidney, spleen, muscle, etc. A sample of this invention can also include a substance not obtained from the body of a subject of this invention. Examples of such a sample include but are not limited to, a water sample, a food or foodstuff sample, a plant or plant material sample, a soil or dirt sample, an effluent sample, etc.

In further embodiments, the compositions of this invention can also be used to treat or prevent cancer in a subject. Thus, in additional embodiments, the present invention provides a method of treating cancer in a subject, comprising administering to the subject a poxvirus engineered to lack A35R protein activity. A poxvirus employed in these methods would be a poxvirus that is specific for cancer cells.

In other embodiments, the present invention provides a method of treating cancer in a subject, comprising administering to the subject a poxvirus engineered to lack A35R protein activity and wherein the poxvirus can further comprise a) nucleic acid encoding a costimulatory molecule (e.g., B7.1, ICAM-1, LFA-3, etc., as known in the art); b) nucleic acid encoding a tumor antigen; and c) nucleic acid encoding an immunomodulatory protein or molecule. These nucleic acids can be present separately and/or in any combination in the poxvirus genome.

The present invention further provides compositions. Thus, in one embodiment, provided herein is a composition comprising A35R protein and a pharmaceutically acceptable carrier. In other embodiments, a poxvirus engineered to lack A35R activity is provided. Further provided is a composition comprising a poxvirus engineered to lack A35R activity and a pharmaceutically acceptable carrier. Also provided herein is an isolated nucleic acid encoding an A35R protein or active fragment thereof of a vaccinia virus or other poxvirus. Additionally provided herein is a composition comprising an isolated nucleic acid encoding an A35R protein or active fragment thereof of a vaccinia virus and a pharmaceutically acceptable carrier. In further embodiments, the present invention provides a composition comprising an antibody that specifically binds an A35R protein or active fragment thereof and a pharmaceutically acceptable carrier, as well as an antibody that specifically binds an A35R protein or active fragment thereof.

As indicated herein, the present invention provides biologically active fragments of the proteins of this invention, as well as antibodies that specifically bind the proteins and/or fragments of the proteins of this invention.

Further provided are isolated nucleic acids comprising, consisting essentially of and/or consisting of nucleotide sequences that encode the proteins and fragments of this invention. In particular, the present invention provides an isolated nucleic acid comprising, consisting essentially of, and/or consisting of the nucleotide sequence of Vaccinia virus Copenhagen strain (SEQ ID NO:1):

```
atggacgccgcgtttgttattactccaatgggtgtgttgactataacaga tacattgtatgatgatctcgatatttcaatcatggactttataggaccat
```

-continued

```
acattataggtaacataaaaactgtccaaatagatgtacgggatataaaa tattccgacatgcaaaaatgctactttagctataagggtaaaatagttcc tcaggattctaatgatttggctagattcaacatttatagcatttgtgccg catacagatcaaaaaataccatcatcatagcatgcgactatgatatcatg ttagatatagaagataaacatcagccatttttatctattcccatctattga tgtttttaacgctacaatcatagaagcgtataacctgtatacagctggag attatcatctaatcatcaatccttcagataatctgaaaatgaaattgtcg tttaattcttcattctgcatatcagacggcaatggatggattataattga tgggaaatgcaatagtaatttttttatca.
```

Further provided herein is the nucleotide sequence of the A35R protein of all of the poxviruses identified in Table 1 by virus name, gene name for the A35R ortholog, the GenBank® database accession number, the number of amino acids and the location of the start and stop sites of the open reading frame (ORF) for A35R. Each of these nucleotide sequences is incorporated by reference herein in their entirety.

Additionally provided is a nucleic acid comprising, consisting essentially of, and/or consisting of a nucleotide sequence that encodes an amino acid sequence comprising, consisting essentially of, and/or consisting of the amino acid sequence or a biologically active fragment of any of the following amino acid sequences:

*Vaccinia* virus Copenhagen strain A35R (SEQ ID NO: 2):
MDAAFVITPMGVLTITDTLYDDLDISIMDFIGPYIIGNIKTVQIDVRDIKYSDMQKCYFS

YKGKIVPQDSNDLARFNIYSICAAYRSKNTIIIACDYDIMLDIEDKHQPFYLFPSIDVFN

ATIIEAYNLYTAGDYHLIINPSDNLKMKLSFNSSFCISDGNGWIIIDGKCNSNFLS;

*Variola* virus strain Garcia A39R gene/protein: (SEQ ID NO: 3):
MDTTFVITPMGMLTITDTLYDDLDISIMDFIGPYIIGNIKTVQIDVRDIKYSDMQKCYFS;
and

*Variola* virus strain India A38R: (SEQ ID NO: 4):
MDTTFVITPMGMLTITDTLYDDLDISIMDFIGPYIIGNIKTVQIDVRDIKYSDMQKCYFS.

Further provided herein is a nucleic acid that is the complement of each and any of the nucleic acids of this invention.

The present invention also provides an isolated A35R protein, which can be a protein having the amino acid sequence of SEQ ID NO:2. Also provided herein is the amino acid sequence for the A35R protein of the poxviruses identified in Table 1, as available in the GenBank® database. These amino acid sequences are incorporated by reference herein in their entirety. Specific examples of nucleotide sequences of poxviruses of this invention, such as Bovine popular stomatitis virus (SEQ ID NO:8), Camelpox virus (SEQ ID NO:9), Cowpox virus (SEQ ID NO:10), Deerpox virus (SEQ ID NO:11), Ectromelia virus (SEQ ID NO:12), Goatpox virus Pellor (SEQ ID NO:13), lumpy skin disease virus (SEQ ID NO:14), Molluscum contagiosum virus (SEQ ID NO:15), Monkeypox virus (SEQ ID NOS:16, 17 and 18), Myxoma virus (SEQ ID NO:19), Orf virus (SEQ ID NO:20), Rabbitpox virus (SEQ ID NO:21), Rabbit fibroma virus (SEQ ID NO:22), sheeppox virus (SEQ ID NO:23), Swinepox virus (SEQ ID NO:24), Vaccinia virus (SEQ ID NOS:25, 26, 27, 28 and 29), Yaba-like disease virus (SEQ ID NO:30) and Yaba-like monkey tumor virus (SEQ ID NO:31) are provided in Table 2. Specific examples of amino acid sequences of poxviruses of the invention, such as Bovine popular stomatitis virus (SEQ ID NO:32), Deerpox virus (SEQ ID NO:33), lumpy skin disease virus (SEQ ID NO:34), Molluscum contagiosum virus (SEQ ID NO:35), Myxoma virus (SEQ ID NO:36), Orf virus (SEQ ID NO:37), sheeppox virus (SEQ ID NO:38), Swinepox virus (SEQ ID NO:39), Vaccinia virus (SEQ ID NO:40), Variola virus (SEQ ID NO:41), Yaba-like disease virus (SEQ ID NO:42) and Yaba-like monkey tumor virus (SEQ ID NO:43) are provided in Table 3.

Also provided herein are probes and primers for the detection of the nucleic acids of this invention and such primers and/or probes can be used alone and/or in any combination. Probes and primers of this invention can be prepared according to art known methods for identifying primer pairs and probes using art-known procedures and/or commercially available software for identifying regions that are optimal for priming and probing protocols. As would be known to one of ordinary skill in the art, any part of the A35R nucleotide sequence of this invention (or its complement) could be used as a primer and/or probe. A nonlimiting example of a primer pair is: 5' atggacgccgcgtttgttatta 3' (SEQ ID NO:5) and 5' tgataaaaaattactatt 3' (SEQ ID NO:6), which could be used to amplify an A35R sequence by PCR. An example of a probe to detect A35R nucleic acid could be 5' tgataaaaaattactattgc 3' (SEQ ID NO:7).—

In certain embodiments, the fragments and/or polypeptides of this invention can be fused with a "carrier" protein or peptide to produce a fusion protein. Such fusion can be carried out, for example, by linking a nucleic acid of this invention in frame with a nucleic acid encoding a carrier protein or fragment thereof of this invention and expressing the linked nucleotide sequence to produce the fusion protein. For example, the carrier protein or peptide can be fused to a polypeptide and/or fragment of this invention to increase the stability thereof (e.g., decrease the turnover rate) in the cell and/or subject. Exemplary carrier proteins include, but are not limited to, glutathione-S-transferase or maltose-binding protein. The carrier protein or peptide can alternatively be a reporter protein. For example, the fusion protein can comprise a polypeptide and/or fragment of this invention and a reporter protein or peptide (e.g., green fluorescence protein (GFP), β-glucoronidase, β-galactosidase, luciferase, and the like) for easy detection of transformed cells and transgene expression. Any suitable carrier protein and/or nucleic acid encoding the carrier protein, as is well known in the art can be used to produce a fusion protein of this invention.

A variety of protocols for detecting the presence of and/or measuring the amount of polypeptides, fragments and/or peptides of this invention in a sample, using polyclonal and/or monoclonal antibodies specific for the polypeptide, fragment and/or peptide are known in the art. Examples of such protocols include, but are not limited to, enzyme immunoassays (EIA), agglutination assays, immunoblots (Western blot; dot/slot blot, etc.), radioimmunoassays (RIA), immunodiffusion assays, chemiluminescence assays, antibody library screens, expression arrays, enzyme-linked immunosorbent assays (ELISA), radioimmunoassays (RIA), immunoprecipitation, Western blotting, competitive binding assays, immunofluorescence, immunohistochemical staining precipitation/flocculation assays and fluorescence-activated cell sorting (FACS). These and other assays are described, among other places, in Hampton et al. (*Serological Methods, a Laboratory Manual*, APS Press, St Paul, Minn. (1990)) and Maddox et al. (*J. Exp. Med.* 158:1211-1216 (1993)).

Furthermore, a number of assays for identification, detection and/or amplification of nucleic acid sequences are well known in the art. For example, various protocols can be employed in the methods of this invention to amplify nucleic acid. As used herein, the term "oligonucleotide-directed amplification procedure" refers to template-dependent processes that result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term "template dependent process" refers to nucleic acid synthesis of a RNA or a DNA molecule wherein the sequence of the newly synthesized strand of nucleic acid is dictated by the well-known rules of complementary base pairing. Typically, vector mediated methodologies involve the introduction of the nucleic acid fragment into a DNA or RNA vector, the clonal amplification of the vector, and the recovery of the amplified nucleic acid fragment. Examples of such methodologies are provided in U.S. Pat. No. 4,237,224 (incorporated herein by reference in its entirety). Nucleic acids, used as a template for amplification methods can be isolated from cells according to standard methodologies (Sambrook et al., 1989). The nucleic acid can be genomic DNA or fractionated or whole cell RNA. Where RNA is used, it may be desired to convert the RNA to a complementary DNA. In one embodiment, the RNA can be whole cell RNA and is used directly as the template for amplification.

Pairs of primers that selectively hybridize to nucleic acids corresponding to the A35R gene or coding sequence are contacted with the nucleic acid under conditions that permit selective hybridization. The term "primer," as defined herein, is meant to encompass any nucleic acid that is capable of priming the synthesis of a nascent nucleic acid in a template dependent process. Typically, primers are oligonucleotides from ten to twenty bases in length, but shorter (e.g., 6, 7, 8, or 9 bases) or longer (e.g., 21, 22, 23, 24, 25, 26, 27, 28, 29, 30, 35, 40, 45, 50 bases) sequences can be employed. Primers can in double-stranded or single-stranded form, although the single-stranded form is commonly used.

Once hybridized, the nucleic acid: primer hybridization complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In some embodiments, the detection can be performed by visual means. Alternatively, the detection can involve indirect identification of the product via chemiluminescence, radioactive scintigraphy of incorporated radiolabel or fluorescence or chemiluminescence label or even via a system using electrical or thermal impulse signals (e.g., Affymax technology).

A number of template dependent processes are available to amplify the sequences present in a given template sample. One of the best-known amplification methods is the polymerase chain reaction (referred to as PCR), which is described in detail in U.S. Pat. Nos. 4,683,195, 4,683,202 and 4,800,159, each incorporated herein by reference in its entirety.

Briefly, in PCR, two primer sequences are prepared that are complementary to regions on opposite complementary strands of the target sequence. An excess of deoxynucleoside triphosphates is added to a reaction mixture along with a DNA polymerase, e.g., a Taq polymerase. If the particular target sequence is present in a sample, the primers will bind to the target sequence and the polymerase will cause the primers to be extended along the sequence by adding on nucleotides. By raising and lowering the temperature of the reaction mixture, the extended primers will dissociate from the target sequence to form reaction products, excess primers will bind to the target sequence and to the reaction products and the process is repeated.

A reverse transcriptase PCR amplification procedure can be performed in order to quantify the amount of mRNA amplified. Methods of reverse transcribing RNA into cDNA are well known in the art (e.g., Sambrook et al., 1989). Alternative methods for reverse transcription employ thermostable, RNA-dependent DNA polymerases. These methods are described, for example, in PCT Publication No. WO 90/07641, filed Dec. 21, 1990, incorporated herein by reference in its entirety. Polymerase chain reaction methodologies are well known in the art.

Another method for nucleic acid amplification is the ligase chain reaction ("LCR"), disclosed in Eur. Pat. Appl. No. 320308, incorporated herein by reference in its entirety. In LCR, two complementary probe pairs are prepared and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 (incorporated by reference herein in its entirety) describes a method similar to LCR for binding probe pairs to a target sequence.

Qbeta replicase (QβR), described in PCT Application No. PCT/US87/00880, (incorporated herein by reference), can also be used as an amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]triphosphates in one strand of a restriction site may also be useful in the amplification of nucleic acids in the present invention.

Strand Displacement Amplification (SDA), described in U.S. Pat. Nos. 5,455,166, 5,648,211, 5,712,124 and 5,744, 311, each incorporated herein by reference, is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present.

The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification method, as described in Intl. Pat. Appl. No. PCT/US89/01025, which is incorporated herein by reference in its entirety, may be used in accordance with the present invention. In one embodiment, "modified" primers are used in a PCR-like, template- and enzyme-dependent synthesis. The primers may be modified by labeling with a capture moiety (e.g., biotin) and/or a detectable moiety (e.g., enzyme). In another embodiment, an excess of labeled probes is added to a sample. In the presence of the target sequence, the probe binds and is cleaved catalytically. After cleavage, the target sequence is released intact, available to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (PCT Publication No. WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7, T3 or SP6. In an isothermal cyclic reaction, the RNAs are reverse transcribed into single stranded DNA, which is then converted to double-stranded DNA, and then transcribed once again with an RNA polymerase such as T7, T3 or SP6. The resulting products, whether truncated or complete, indicate target specific sequences.

Eur. Pat. Appl. No. 329822 (incorporated herein by reference in its entirety) discloses a nucleic acid amplification process involving cyclically synthesizing single stranded RNA (ssRNA), ssDNA, and double-stranded DNA (dsDNA), which can be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA).

The resultant ssDNA is a template for a second primer, which also includes the sequences of an RNA polymerase promoter (exemplified by T7 RNA polymerase) 5' to its homology to the template. This primer is then extended by DNA polymerase (exemplified by the large Klenow fragment of E. coli DNA polymerase I), resulting in a double-stranded DNA (dsDNA) molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle, leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Application WO 89/06700 (incorporated herein by reference in its entirety) discloses a nucleic acid sequence amplification scheme based on the hybridization of a promoter/primer sequence to a target single-stranded DNA (ssDNA), followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated by reference herein).

Methods based on ligation of two (or more) oligonucleotides in the presence of nucleic acid having the sequence of the resulting "di-oligonucleotide," thereby amplifying the dioligonucleotide, can also be used in the amplification step of the present invention.

Following any amplification, it is desirable to separate the amplification product from the template and the excess primer for the purpose of determining whether specific amplification has occurred. In one embodiment, amplification products can be separated by agarose, agarose-acrylamide or polyacrylamide gel electrophoresis using standard methods (e.g., Sambrook et al., 1989).

Alternatively, chromatographic techniques can be used to effect separation. There are many kinds of chromatography that can be used in the present invention: such as, for example, adsorption, partition, ion exchange and molecular sieve, as well as many specialized techniques for using them, including column, paper, thin-layer and gas chromatography.

Amplification products must be visualized in order to confirm amplification of the target sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In some embodiments, visualization is achieved indirectly. Following separation of amplification products, a labeled, nucleic acid probe is brought into contact with the amplified target sequence. The probe preferably is conjugated to a chromophore but may be radiolabeled. In another embodiment, the probe is conjugated to a binding partner, such as an antibody or biotin, and the other member of the binding pair carries a detectable moiety.

In other embodiments, detection can be by Southern blotting and hybridization with a labeled probe. The techniques involved in Southern blotting are well known to those of skill in the art and can be found in many standard books on molecular protocols (e.g., Sambrook et al., 1989). Briefly, amplification products are separated by gel electrophoresis. The gel is then contacted with a membrane, such as nitrocellulose, permitting transfer of the nucleic acid and noncovalent binding. Subsequently, the membrane is incubated with a chromophore-conjugated probe that is capable of hybridizing with a target amplification product. Detection is by exposure of the membrane to x-ray film or ion-emitting detection devices. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel.

Additionally, a wide variety of labeling and conjugation techniques are known in the art that are used in various nucleic acid detection and amplification assays. Methods for producing labeled hybridization probes and/or PCR or other ligation primers for detecting and/or amplifying nucleic acid sequences can include, for example, oligolabeling, nick translation and end-labeling, as well as other well known methods. Alternatively, nucleic acid sequences encoding the polypeptides of this invention, and/or any functional fragment thereof, can be cloned into a plasmid or vector for detection and amplification. Such plasmids and vectors are well known in the art and are commercially available. It is also contemplated that the methods of this invention can be conducted using a variety of commercially available kits (e.g., Pharmacia & Upjohn; Promega; U.S. Biochemical Corp.). Suitable reporter molecules or labels, which can be used for ease of detection, include, for example, radionuclides, enzymes, fluorescence agents, chemiluminescence agents and chromogenic agents, as well as substrates, cofactors, inhibitors, magnetic particles and the like as are well known in the art.

The present invention further includes isolated polypeptides, peptides, proteins, fragments, domains and/or nucleic acid molecules that are substantially equivalent to those described for this invention. As used herein, "substantially equivalent" can refer both to nucleic acid and amino acid sequences, for example a mutant sequence, that varies from a reference sequence by one or more substitutions, deletions, or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologs, as well as methods of obtaining homologs, of the polypeptides and/or fragments of this invention from other poxviruses. As used herein, an amino acid sequence or protein is defined as a homolog of a polypeptide or fragment of the present invention if it shares significant homology to one of the polypeptides and/or fragments of the present invention. Significant homology means at least 30%, 40%, 50%, 60%, 65%, 75%, 80%, 85%, 90%, 95%, 98% and/or 100% homology with another amino acid sequence. Specifically, by using the nucleic acids disclosed herein as a probe or as primers, and techniques such as PCR amplification and colony/plaque hybridization, one skilled in the art can identify homologs of the polypeptides and/or fragments of this invention in any mammalian-tropic poxvirus It is further contemplated that the present invention provides kits for detection of the polypeptides and/or fragments and/or antibodies of this invention in a sample. In one embodiment, the kit can comprise one or more antibodies of this invention, along with suitable buffers, wash solutions and/or other reagents for the detection of antibody/antigen complex formation. In an alternative embodiment, a kit of this invention can comprise a polypeptide, an antigenic peptide of the polypeptide of this invention, a fragment of this invention and/or an antigenic peptide of a fragment of this invention, along with suitable buffers, wash solutions and/or other reagents for the detection of antibody/antigen complex formation.

The present invention further provides a kit for the detection of nucleic acid encoding the polypeptides and/or fragments of this invention. For example, in one embodiment, the kit can comprise one or more nucleic acids of this invention, along with suitable buffers, wash solutions and/or other reagents for the detection of hybridization complex formation and/or amplification product formation.

It would be well understood by one of ordinary skill in the art that the kits of this invention can comprise one or more containers and/or receptacles to hold the reagents (e.g., antibodies, antigens, nucleic acids) of the kit, along with appropriate buffers and/or wash solutions and directions for using the kit, as would be well known in the art. Such kits can further comprise adjuvants and/or other immunostimulatory or immunomodulating agents, as are well known in the art.

In further embodiments, the nucleic acids encoding the polypeptides and/or fragments of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a polypeptide and/or biologically active fragment of this invention.

The present invention further provides a vector comprising a nucleic acid encoding a polypeptide and/or fragment of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, poxvirus, vaccinia virus, adenovirus, retrovirus and/or adeno-associated virus nucleic acid. The nucleic acid or vector of this invention can also be in a liposome or a delivery vehicle, which can be taken up by a cell via receptor-mediated or other type of endocytosis.

The nucleic acid of this invention can be in a cell, which can be a cell expressing the nucleic acid whereby a polypeptide and/or biologically active fragment of this invention is produced in the cell. In addition, the vector of this invention can be in a cell, which can be a cell expressing the nucleic acid of the vector whereby a polypeptide and/or biologically active fragment of this invention is produced in the cell. It is also contemplated that the nucleic acids and/or vectors of this invention can be present in a host animal (e.g., a transgenic animal), which expresses the nucleic acids of this invention and produces the polypeptides and/or fragments of this invention.

The nucleic acid encoding the polypeptide and/or fragment of this invention can be any nucleic acid that functionally encodes the polypeptides and/or fragments of this invention. To functionally encode the polypeptides and/or fragments (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Nonlimiting examples of expression control sequences that can be present in a nucleic acid of this invention include promoters derived from metallothionine genes, actin genes, immunoglobulin genes, CMV, SV40, adenovirus, bovine papilloma virus, etc. A nucleic acid encoding a selected polypeptide and/or fragment can readily be determined based upon the genetic code for the amino acid sequence of the selected polypeptide and/or fragment and many nucleic acids will encode any selected polypeptide and/or fragment. Modifications in the nucleic acid sequence encoding the polypeptide and/or fragment are also contemplated. Modifications that can be useful are modifications to the sequences controlling expression of the polypeptide and/or fragment to make production of the polypeptide and/or fragment inducible or repressible as controlled by the appropriate inducer or repressor. Such methods are standard in the art. The nucleic acid of this invention can be generated by means standard in the art, such as by recombinant nucleic acid techniques and/or by synthetic nucleic acid synthesis or in vitro enzymatic synthesis.

The nucleic acids and/or vectors of this invention can be transferred into a host cell (e.g., a prokaryotic or eukaryotic cell) by well-known methods, which vary depending on the type of cell host. For example, calcium chloride transfection is commonly used for prokaryotic cells, whereas calcium phosphate treatment, transduction and/or electroporation can be used for other cell hosts.

The present invention also provides various screening assays to identify substances that either enhance or inhibit the activity of A35R, either at the protein or nucleic acid level.

In one embodiment, provided herein is a method of identifying a substance having the ability to inhibit or enhance the binding activity of a polypeptide and/or biologically active fragment of this invention comprising contacting the substance with the A35R protein or a biologically active fragment thereof under conditions whereby binding can occur and detecting a decrease or increase in the amount of binding in the presence of the substance as compared to a control amount of binding in the absence of the substance, thereby identifying a substance having the ability to inhibit or enhance the binding activity of the A35R protein.

Inhibition or enhancement of binding activity can be detected by any of a variety of art-recognized methods for evaluating binding activity. As one example, the substance to be tested and the A35R polypeptide and/or fragment can be contacted in the presence of target cells or a target substrate known to bind the A35R polypeptide or fragment. The amount of binding of polypeptide or fragment to the cells or the substrate in the presence of the substance and the amount of binding of polypeptide or fragment to the cells or the substrate in the absence of the substance is determined and a decrease or increase in the amount of binding in the presence of the substance identifies the substance as having the ability to inhibit or enhance binding. Nonlimiting examples of binding targets for A35R protein include antibodies, antibody fragments, ligands, cellular proteins, viral proteins, small molecules and/or drugs that specifically bind A35R protein or an active fragment thereof.

In some embodiments, binding of the A35R polypeptide and/or fragment to target cells or a target substrate can be measured by attaching a detectable moiety to the polypeptide or fragment (e.g., a fluorescence moiety, histochemically detectable moiety, radioactive moiety, etc.). The amount of detectable moiety can be measured in the presence and absence of the substance to be tested and the amounts can be compared to determine inhibition or enhancement.

In addition, the present invention provides a method of identifying a substance having the ability to inhibit or enhance the immunomodulating activity of an A35R polypeptide and/or a biologically active fragment of this invention, comprising contacting the substance with the A35R polypeptide of this invention and/or a biologically active fragment thereof under conditions whereby immunomodulating activity can occur and detecting a decrease or increase in the amount of immunomodulating activity in the presence of the substance as compared to a control amount of immunomodulating activity in the absence of the substance, thereby identifying a substance having the ability to inhibit or enhance the immunomodulating activity of the A35R protein.

Inhibition or enhancement of the immunomodulating activity of the A35R protein can be detected by any of a variety of art-recognized methods for evaluating immunomodulating activity, including the assays for nitric oxide production and interleukin 2 (IL-2) secretion as described in the Examples section herein.

Further provided is a method of identifying a substance having the ability to enhance or inhibit the immunogenic activity of the A35R protein of this invention and/or a biologically active fragment thereof, comprising contacting the substance with the A35R protein or an immunogenic fragment thereof under conditions whereby a measurable immune response can be elicited and detecting an increase or decrease in the amount of immune response in the presence of the substance, as compared to a control amount of immune response in the absence of the substance, thereby identifying a substance having the ability to enhance or inhibit immunogenic activity of the A35R protein. Assays to detect and measure immune responses are well known in the art and can be employed to detect either humoral or cellular immune responses.

It is also contemplated that the present invention includes methods of screening poxviruses for mutants defective in one or more of the biological activities of the A35R protein, for use, for example, in a vaccine preparation. Such mutants can be identified as having a defect in any of the biological activities of the A35R protein according to the protocols described herein and as are known in the art. Such mutants can be further tested for being attenuated in the ability to produce a clinical infection in a subject (i.e., for virulence potential) and then further evaluated for use as a vaccine according to known protocols.

For example, in one embodiment, poxviruses containing a mutation in the A35R coding sequence or lacking the A35R coding sequence) can be generated through such art-known techniques as gene disruption and their virulence potential determined by challenge studies in animals and by assessments of immunomodulating activity as described herein. In addition, complementation studies can be performed to restore the defective activity of the A35R protein, in order to characterize the mutant.

DEFINITIONS

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

A poxvirus of this invention includes but is not limited to vaccinia virus, molluscum contagiosum, camelpox virus, cowpox virus, ectromelia (mousepox) virus, rabbitpox virus, monkeypox virus, raccoonpox virus, taterapox virus, buffalopox virus variola major virus, variola minor virus, lumpy skin disease virus, swinepox virus, Yaba virus, sheeppox virus, myxoma virus volepox virus and any other poxvirus that has an A35R protein, either now known or later identified. Additional poxviruses are listed in Table 1.

The A35R gene and A35R protein of this invention is an A35R gene or A35R protein or its ortholog from a poxvirus of this invention. The A35R gene encodes a 176 amino acid protein in VV Copenhagen strain, modified vaccinia Ankara strain and Tian Tan strain (GenBank AF095689). The VV-A35R orthologs are conserved in all poxviruses with a mammalian host range, ranging in size from 176 to 192 amino acids in all sequenced viruses, except for a large ortholog of 233 amino acids in molluscum contagiosum virus. The gene is fragmented into 60 amino acid and 50 amino acid open reading frames (ORFs) in variola virus sequences (India, Bangladesh and Garcia).

As used herein, "modulate," "modulates" or "modulation" refers to enhancement (e.g., an increase) or inhibition (e.g., diminished, reduced or suppressed) of the specified activity.

The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%.

The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified activity of at least about 5%, 10%, 25%, 35%, 40%, 50%, 60%, 75%, 80%, 90%, 95%, 97%, 98%, 99% or 100%. In particular embodiments, the inhibition or reduction results in little or essentially no detectable activity (at most, an insignificant amount, e.g., less than about 10% or about 5%).

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP §2111.03. Thus, the term "consisting essentially of" when used in a claim of this invention is not intended to be interpreted to be equivalent to "comprising."

"Isolated" as used herein means the nucleic acid or protein or protein fragment of this invention is sufficiently free of contaminants or cell components with which nucleic acids or proteins normally occur. "Isolated" does not mean that the preparation is technically pure (homogeneous), but it is sufficiently pure to provide the nucleic acid or protein or protein fragment in a form in which it can be used therapeutically.

"Epitope" or "antigenic epitope" or "antigenic peptide" as used herein means a specific amino acid sequence which, when present in the proper conformation, provides a reactive site for an antibody or T cell receptor. The identification of epitopes on antigens can be carried out by immunology protocols that are well known in the art. Typically, an epitope or antigenic peptide can be 4, 5, 6, 7, 8, 9, 10, 12, 14, 16, 18, 20, 25, 30, 35, 40, 45 or 50 amino acids in length.

As used herein, the term "polypeptide" or "protein" is used to describe a chain of amino acids that correspond to those encoded by a nucleic acid. A polypeptide of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences disclosed herein are presented in the amino to carboxy direction, from left to right. Nucleotide sequences are presented herein in the 5' to 3' direction, from left to right. It is intended that the nucleic acids of this invention can be either single or double stranded (i.e., including the complementary nucleic acid). A nucleic acid of this invention can be the complement of a nucleic acid described herein.

A "biologically active fragment" or "active fragment" as used herein includes a polypeptide of this invention that comprises a sufficient number of amino acids to have one or more of the biological activities of the polypeptides of this invention. Such biological activities can include, but are not limited to, in any combination, binding activity, immunomodulating activity, virulence activity and/or immunogenic activity, as well as any other activity now known or later identified for the polypeptides and/or fragments of this invention. A fragment of a polypeptide of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention according to the methods described herein, which are routine methods for testing activities of polypeptides, and/or according to any art-known and routine methods for identifying such activities. Such production and testing to identify biologically active fragments of the polypeptides described herein would be well within the scope of one of ordinary skill in the art and would be routine.

Fragments of the polypeptides of this invention are preferably at least about ten amino acids in length and retain one or more of the biological activities (e.g., immunomodulating; virulence activities) and/or the immunological activities of the A35R protein. Examples of the fragments of this invention include, but are not intended to be limited to, the following fragments identified by the amino acid number as shown in the Sequence Listing for SEQ ID NO:2: Amino acids 1-10, 10-20, 20-30, 30-40, 40-50, 50-60, 60-70, 70-80, 80-90, 90-100, 110-120, 120-130, 130-140, 140-150, 150-160, 160-170, 170-180, 180-190, 190-200, 200-210, 210-220, 220-230, 230-240, 240-250, 1-25, 1-50, 1-67, 1-75, 1-100, 1-125, 1-135, 1-145, 1-150, 1-160, 1-170, 1-180, 1-190, 1-200, 1-250, 68-180, 183-223, 50-100, 100-200, 200-250, etc.

It is understood that this list is exemplary only and that a fragment of this invention can be any amino acid sequence containing any combination of contiguous amino acids that are numbered in the Sequence Listing as amino acids 1 through 250 even if that combination is not specifically recited as an example herein. It is also understood that these fragments can be combined in any order or amount. For example, fragment 1-10 can be combined with fragment 10-20 to produce a fragment of amino acids 1-20. As another example, fragment 1-20 can be combined with fragment 50-60 to produce a single fragment of this invention having 31 amino acids (AA 10-20 and AA 50-60). Also fragments can be present in multiple numbers and in any combination in a fragment of this invention. Thus, for example, fragment 1-150 can be combined with a second fragment 1-150 and/or combined with fragment 225-230 to produce a fragment of this invention. Other exemplary fragments of this invention include amino acids 1-60 of variola virus; and the amino acid sequence:
YDDLDISIMDFIGPY (SEQ ID NO:44).

The terms "homology," "identity" and "complementarity" as used herein refer to a degree of similarity between two or more sequences. There may be partial homology or complete homology (i.e., identity). A partially complementary sequence that at least partially inhibits an identical sequence from hybridizing to a target nucleic acid is referred to as "substantially homologous." The inhibition of hybridization of the completely complementary sequence to the target sequence can be examined using a hybridization assay (Southern or Northern blot, solution hybridization and the like) under conditions of low stringency. A substantially homologous sequence or hybridization probe will compete for and inhibit the binding of a completely homologous sequence to the target sequence under conditions of low stringency, as this term is known in the art. This is not to say that conditions of low stringency are such that non-specific binding is permitted; low stringency conditions require that the binding of two sequences to one another be a specific (i.e., selective) interaction. The absence of non-specific binding can be tested by the use of a second target sequence that lacks even a partial degree of complementarity (e.g., less than about 30% identity). In the absence of non-specific binding, the probe will not hybridize to the second non-complementary target sequence.

The term "hybridization" as used herein refers to any process by which a first strand of nucleic acid binds with a second strand of nucleic acid through base pairing. Nucleic acids encoding the polypeptides and/or fragments of this invention can be detected by DNA-DNA or DNA-RNA hybridization and/or amplification using probes, primers and/or fragments of polynucleotides encoding the polypeptides and/or fragments of this invention and/or designed to detect and/or amplify the nucleic acids of this invention.

The term "hybridization complex" as used herein refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells and/or nucleic acids have been fixed).

The term "nucleotide sequence" refers to a heteropolymer of nucleotides or the sequence of these nucleotides. The terms "nucleic acid," "oligonucleotide" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene. Nucleic acids of this invention can comprise a nucleotide sequence that can be identical in sequence to the sequence which is naturally occurring or, due to the well-characterized degeneracy of the nucleic acid code, can include alternative codons that encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained.

The term "probe" or "primer" includes naturally occurring and/or recombinant and/or chemically synthesized single- and/or double-stranded nucleic acids. They can be labeled for detection by nick translation, Klenow fill-in reaction, PCR and/or other methods well known in the art. Probes and primers of the present invention, their preparation and/or labeling are described in Sambrook et al. 1989. *Molecular Cloning: A Laboratory Manual*, Cold Spring Harbor Laboratory, NY and Ausubel et al. 1989. *Current Protocols in Molecular Biology*, John Wiley & Sons, New York N.Y., both of which are incorporated herein by reference in their entirety for these teachings.

The term "stringent" as used herein refers to hybridization conditions that are commonly understood in the art to define the conditions of the hybridization procedure. Stringency conditions can be low, high or medium, as those terms are commonly know in the art and well recognized by one of ordinary skill. In various embodiments, stringent conditions can include, for example, highly stringent (i.e., high stringency) conditions (e.g., hybridization in 0.5 M $NaHPO_4$, 7% sodium dodecyl sulfate (SDS), 1 mM EDTA at 65° C., and washing in 0.1×SSC/0.1% SDS at 68° C.), and/or moderately stringent (i.e., medium stringency) conditions (e.g., washing in 0.2×SSC/0.1% SDS at 42° C.).

"Amplification" as used herein includes the production of multiple copies of a nucleic acid molecule and is generally carried out using polymerase chain reaction (PCR) and/or any other amplification technologies as are well known in the art (Dieffenbach and Dveksler. 1995. *PCR Primer, a Laboratory Manual*, Cold Spring Harbor Press, Plainview, N.Y.).

The term "sample" as used herein is used in its broadest sense. A biological sample suspected of containing a polypeptide, fragment, antibody and/or nucleic acid of this invention can be any biological fluid, an extract from a cell, an extracellular matrix isolated from a cell, a cell (in solution or bound to a solid support), a tissue, a tissue print, and the like. A sample of this invention can also include a substance not obtained from the body of a subject of this invention. Examples of such a sample include but are not limited to, a water or fluid sample, a food or foodstuff sample, a plant or plant material sample, a soil or rock sample, an animal or animal material sample, an animal bedding sample, an animal cage sample, air sample a soil or dirt sample, a cloth, paper or other material used to swab, wipe, dust or clean a surface, an effluent sample, etc.

"Effective amount" as used herein refers to an amount of a compound, agent, substance or composition of this invention that is sufficient to produce a desired effect, which can be a therapeutic effect. The effective amount will vary with the age, general condition of the subject, the severity of the condition being treated, the particular compound, agent, substance or composition administered, the duration of the treatment, the nature of any concurrent treatment, the pharmaceutically acceptable carrier used if any, and like factors within the knowledge and expertise of those skilled in the art. As appropriate, an "effective amount" in any individual case can be determined by one of ordinary skill in the art by reference to the pertinent texts and literature and/or by using routine experimentation. (Remington, *The Science And Practice of Pharmacy* (20th ed. 2000)).

A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components (e.g., pharmaceutically acceptable carriers) include, without limitation, any of the standard pharmaceutical carriers such as phosphate buffered saline solutions, water, emulsions such as oil/water emulsion, microemulsions and various types of wetting agents. In particular, it is intended that a pharmaceutically acceptable carrier be a sterile carrier that is formulated for administration to or delivery into a subject of this invention.

Furthermore, any of the compositions of this invention can comprise a pharmaceutically acceptable carrier and a suitable adjuvant. As used herein, "suitable adjuvant" describes an adjuvant capable of being combined with the polypeptide and/or fragment and/or nucleic acid of this invention to further enhance an immune response without deleterious effect on the subject or the cell of the subject. A suitable adjuvant can be, but is not limited to, MONTANIDE ISA51 (Seppic, Inc., Fairfield, N.J.), SYNTEX adjuvant formulation 1 (SAF-1), composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

The compositions of the present invention can also include other medicinal agents, pharmaceutical agents, carriers, diluents, immunostimulatory cytokines, etc. Actual methods of preparing such dosage forms are known, or will be apparent, to those skilled in this art.

A "tumor antigen" of this invention (i.e., an antigen specifically associated with tumor cells) of this invention can include, for example, HER2/neu and BRCA1 antigens for breast cancer, MART-1/MelanA, gp100, tyrosinase, TRP-1, TRP-2, NY-ESO-1, CDK-4, β-catenin, MUM-1, Caspase-8, KIAA0205, HPVE7, SART-1, PRAME, and p15 antigens, members of the MAGE family, the BAGE family (such as BAGE-1), the DAGE/PRAME family (such as DAGE-1), the GAGE family, the RAGE family (such as RAGE-1), the SMAGE family, NAG, TAG-72, CA125, mutated proto-oncogenes such as p21ras, mutated tumor suppressor genes such as p53, tumor associated viral antigens (e.g., HPV16 E7), the SSX family, HOM-MEL-55, NY-COL-2, HOM-HD-397, HOM-RCC-1.14, HOM-HD-21, HOM-NSCLC-11, HOM-MEL-2.4, HOM-TES-11, RCC-3.1.3, NY-ESO-1, and the SCP family. Members of the MAGE family include, but are not limited to, MAGE-1, MAGE-2, MAGE-3, MAGE-4 and MAGE-11. Members of the GAGE family include, but are not limited to, GAGE-1, GAGE-6. See, e.g., review by Van den Eynde and van der Bruggen (1997) in *Curr. Opin. Immunol.* 9: 684-693, Sahin et al. (1997) in *Curr. Opin. Immunol.* 9: 709-716, and Shawler et al. (1997), the entire contents of which are incorporated by reference herein for their teachings of cancer antigens.

The tumor antigen can also be, but is not limited to, human epithelial cell mucin (Muc-1; a 20 amino acid core repeat for Muc-1 glycoprotein, present on breast cancer cells and pancreatic cancer cells), MUC-2, MUC-3, MUC-18, the Ha-ras oncogene product, carcino-embryonic antigen (CEA), the raf oncogene product, CA-125, GD2, GD3, GM2, TF, sTn, gp75, EBV-LMP 1 & 2, HPV-F4, 6, 7, prostatic serum antigen (PSA), prostate-specific membrane antigen (PSMA), alpha-fetoprotein (AFP), CO17-1A, GA733, gp72, p53, the ras oncogene product, β-HCG, gp43, HSP-70, p17 mel, HSP-70, gp43, HMW, HOJ-1, melanoma gangliosides, TAG-72, mutated proto-oncogenes such as p21ras, mutated tumor suppressor genes such as p53, estrogen receptor, milk fat globulin, telomerases, nuclear matrix proteins, prostatic acid phosphatase, protein MZ2-E, polymorphic epithelial mucin (PEM), folate-binding-protein LK26, truncated epidermal growth factor receptor (EGFR), Thomsen-Friedenreich (T) antigen, GM-2 and GD-2 gangliosides, polymorphic epithelial mucin, folate-binding protein LK26, human chorionic gonadotropin (HCG), pancreatic oncofetal antigen, cancer antigens 15-3, 19-9, 549, 195, squamous cell carcinoma antigen (SCCA), ovarian cancer antigen (OCA), pancreas cancer associated antigen (PaA), mutant K-ras proteins, mutant p53, and chimeric protein p210$_{BCR-ABL}$ and tumor associated viral antigens (e.g., HPV16 E7).

The tumor antigen of this invention can also be an antibody produced by a B cell tumor (e.g., B cell lymphoma; B cell leukemia; myeloma; hairy cell leukemia), a fragment of such an antibody, which contains an epitope of the idiotype of the antibody, a malignant B cell antigen receptor, a malignant B cell immunoglobulin idiotype, a variable region of an immunoglobulin, a hypervariable region or complementarity determining region (CDR) of a variable region of an immunoglobulin, a malignant T cell receptor (TCR), a variable region of a TCR and/or a hypervariable region of a TCR. In one embodiment, the cancer antigen of this invention can be a single chain antibody (scFv), comprising linked $V_H$, and $V_L$ domains, which retains the conformation and specific binding activity of the native idiotype of the antibody.

The present invention is in no way limited to the tumor antigens listed herein. Other tumor antigens be identified, isolated and cloned by methods known in the art such as those disclosed in U.S. Pat. No. 4,514,506, the entire contents of which are incorporated by reference herein.

The cancer to be treated by the methods of this invention can be, but is not limited to, B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, adenocarcinoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcinoma, brain cancer, angiosarcoma, hemangiosarcoma, head and neck carcinoma, thyroid carcinoma, soft tissue sarcoma, bone sarcoma, testicular cancer, uterine cancer, cervical cancer, gastrointestinal cancer, and any other cancer now known or later identified (see, e.g., Rosenberg (1996) *Ann. Rev. Med.* 47:481-491, the entire contents of which are incorporated by reference herein).

Infectious and/or pathogenic agents of this invention can include, but are not limited to, Hepadnaviridae, including hepatitis A, B, C, D, E, F, G, etc. (e.g., HBsAg, HBcAg, HBeAg); Flaviviridae, including human hepatitis C virus (HCV), yellow fever virus and dengue viruses; Retroviridae, including human immunodeficiency viruses (HIV) and human T lymphotropic viruses (HTLV1 and HTLV2); Herpesviridae, including herpes simplex viruses (HSV-1 and HSV-2), Epstein Barr virus (EBV), cytomegalovirus, varicella-zoster virus (VZV), human herpes virus 6 (HHV-6) human herpes virus 8 (HHV-8), and herpes B virus; Papovaviridae, including human papilloma viruses; Rhabdoviridae, including rabies virus; Paramyxoviridae, including respiratory syncytial virus; Reoviridae, including rotaviruses; Bunyaviridae, including hantaviruses; Filoviridae, including Ebola virus; Adenoviridae; Parvoviridae, including parvovirus B-19; Arenaviridae, including Lassa virus; Orthomyxoviridae, including influenza viruses; Poxyiridae, including Orf virus, molluscum contageosum virus, smallpox virus and Monkeypox virus; Togaviridae, including Venezuelan equine encephalitis virus; Coronaviridae, including corona viruses such as the severe acute respiratory syndrome (SARS) virus; Picornaviridae including polioviruses; rhinoviruses; orbiviruses; picodnaviruses; encephalomyocarditis virus (EMV); parainfluenza viruses, adenoviruses, coxsackieviruses, echoviruses, rubeola virus, rubella virus, human papillomaviruses, canine distemper virus, canine contagious hepatitis virus, feline calicivirus, feline rhinotracheitis virus, TGE virus (swine), foot and mouth disease virus, simian virus 5, human parainfluenza virus type 2, human metapneuomovirus, enteroviruses, and any other pathogenic virus now known or later identified (see, e.g., *Fundamental Virology, Fields et al., Eds., 3$^{rd}$ ed.*, Lippincott-Raven, New York, 1996, the entire contents of which are incorporated by reference herein for the teachings of pathogenic viruses).

A pathogenic microorganism of this invention can include but is not limited to, *Rickettsia, Chlamydia, Mycobacteria, Clostridia, Corynebacteria, Mycoplasma, Ureaplasma, Legionella, Shigella, Salmonella*, pathogenic *Escherichia coli* species, *Bordatella, Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., 4$^{th}$ ed., Lippincott, New York, 1990, the entire contents of which are incorporated herein by reference for the teachings of pathogenic microorganisms).

Specific examples of microorganisms include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum, Bacillus anthracis, Salmonella typhi, Vibrio cholera, Pasteurella pestis, Pseudomonas aeruginosa, Campylobacter jejuni, Clostridium difficile, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza*, and enterotoxic *Escherichia coli*.

Pathogenic protozoa can include, but are not limited to, *Plasmodium* species (e.g., malaria antigens), *Babeosis* species, *Schistosoma* species, *Trypanosoma* species, *Pneumocystis carnii, Toxoplasma* species, *Leishmania* species, and any other protozoan pathogen now known or later identified.

Also included are pathogenic yeast and fungi, examples of which can be, but are not limited to, *Aspergillus* species, *Candida species, Cryptococcus* species. *Histoplasma* species, *Coccidioides* species, and any other pathogenic fungus now known or later identified.

Transplantation antigens of this invention include, but are not limited to, different antigenic specificities of HLA-A, B and C Class I proteins. Different antigenic specificities of HLA-DR, HLA-DQ, HLA-DP and HLA-DW Class II proteins can also be used (WHO Nomenclature Committee, *Immunogenetics* 16:135 (1992); Hensen et al., in *Fundamental Immunology*, Paul, Ed., pp. 577-628, Raven Press, New York, 1993; NIB GenBank and EMBL data bases).

The present invention also contemplates the treatment or prevention of allergies and/or allergic reaction, caused by various allergens, which can include, but are not limited to, environmental allergens such as dust mite allergens; plant allergens such as pollen, including ragweed pollen; insect allergens such as bee and ant venom; and animal allergens such as cat dander, dog dander and animal saliva allergens.

An "immunomodulatory molecule" of this invention can be, but is not limited to an immunostimulatory cytokine that can be, but is not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules.

Additional examples of an immunomodulatory molecule of this invention include the adjuvants of this invention, including, for example, SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acylated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153 (the entire contents of which are incorporated herein by reference), or a less reactogenic composition where the QS21 is quenched with cholesterol as disclosed in PCT publication number WO 96/33739 (the entire contents of which are incorporated herein by reference). A particularly potent adjuvant formulation involving QS21 3D-MPL & tocopherol in an oil in water emulsion is described in PCT publication number WO 95/17210 (the entire contents of which are incorporated herein by reference). In addition, the nucleic acid of this invention can include an adjuvant by comprising a nucleotide sequence encoding an A35R protein or active fragment thereof of this invention and a nucleotide sequence that provides an adjuvant function, such as CpG sequences. Such CpG sequences, or motifs, are well known in the art.

The terms "treat," "treating" or "treatment" include any type of action that imparts a modulating effect, which, for example, can be a beneficial effect, to a subject afflicted with a disorder, disease, condition or illness, including improvement in the disorder, disease, condition or illness of the subject (e.g., in one or more symptoms), delay in the progression of the disorder, disease, condition or illness, prevention or delay of the onset of the disorder, disease, condition or illness, and/or change in clinical parameters, disorder, disease, condition or illness status, etc., as would be well known in the art.

As used herein, the term "antibody" includes intact immunoglobulin molecules as well as fragments thereof that are capable of binding the epitopic determinant of an antigen (i.e., antigenic determinant). Antibodies that bind the polypeptides of this invention are prepared using intact polypeptides or fragments as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize the animal (e.g., a mouse, rat, or rabbit). The polypeptide or peptide antigens can also be administered with an adjuvant, as described herein and as otherwise known in the art.

An antibody of this invention can be any type of immunoglobulin, including IgG, IgM, IgA, IgD, and/or IgE. The antibody can be monoclonal or polyclonal and can be of any species of origin, including, for example, mouse, rat, rabbit, horse, goat, sheep or human, or can be a chimeric or humanized antibody (e.g., Walker et al., *Molec. Immunol.* 26:403-11 (1989)). The antibodies can be recombinant monoclonal antibodies produced according to the methods disclosed in U.S. Pat. No. 4,474,893 or U.S. Pat. No. 4,816,567. The antibodies can also be chemically constructed according to methods disclosed in U.S. Pat. No. 4,676,980. The antibody can further be a single chain antibody (e.g., scFv) or bispecific antibody.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281). Antibodies can also be obtained by phage display techniques known in the art or by immunizing a heterologous host with a cell containing an epitope of interest.

The polypeptide, fragment or antigenic epitope that is used as an immunogen can be modified or administered in an adjuvant in order to increase antigenicity. Methods of increasing the antigenicity of a protein or peptide are well known in the art and include, but are not limited to, coupling the antigen with a heterologous protein (such as globulin or β-galactosidase) or through the inclusion of an adjuvant during immunization.

For example, for the production of antibodies, various hosts including goats, rabbits, rats, mice, humans, and others, can be immunized by injection with the polypeptides and/or fragments of this invention, with or without a carrier protein. Additionally, various adjuvants may be used to increase the immunological response. Such adjuvants include, but are not limited to, Freund's complete and incomplete adjuvants, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies can be produced in a hybridoma cell line according to the technique of Kohler and Milstein (*Nature* 265:495-97 (1975)). Other techniques for the production of monoclonal antibodies include, but are not limited to, the human B-cell hybridoma technique, and the EBV-hybridoma technique (Kozbor et al. 1985. *J. Immunol. Methods* 81:31-42; Cote et al. 1983. *Proc. Natl. Acad. Sci.* 80:2026-2030; Cole et al. 1984. *Mol. Cell. Biol.* 62:109-120).

For example, to produce monoclonal antibodies, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in a bacterial cell such as *E. coli* by recombinant techniques known to those skilled in the art (e.g., Huse. *Science* 246:1275-81 (1989)). Any one of a number of methods well known in the art can be used to identify the hybridoma cell, which produces an antibody with the desired characteristics. These include screening the hybridomas by ELISA assay, Western blot analysis, or radioimmunoassay. Hybridomas secreting the desired antibodies are cloned and the class and subclass are identified using standard procedures known in the art.

For polyclonal antibodies, antibody-containing serum is isolated from the immunized animal and is screened for the presence of antibodies with the desired specificity using any of the well known procedures as described herein.

The present invention further provides antibodies of this invention in detectably labeled form. Antibodies can be detectably labeled through the use of radioisotopes, affinity labels (such as biotin, avidin, etc.), enzymatic labels (such as horseradish peroxidase, alkaline phosphatase, etc.) fluorescence labels (such as FITC or rhodamine, etc.), paramagnetic atoms, gold beads, etc. Such labeling procedures are well-known in the art. The labeled antibodies of the present invention can be used for in vitro, in vivo, and in situ assays to identify a polypeptide and/or fragment of this invention in a sample.

In some embodiments, the present invention further provides the above-described antibodies immobilized on a solid support (e.g., beads, plates, slides or wells formed from materials such as latex or polystyrene). Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., *Handbook of Experimental Immunology* 4th Ed., Blackwell Scientific Publications, Oxford, England, Chapter 10 (1986)). Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well know in the art.

In addition, techniques developed for the production of chimeric antibodies or humanized antibodies by splicing mouse antibody genes to human antibody genes to obtain a molecule with appropriate antigen specificity and biological activity can be used (Morrison et al. 1984. *Proc. Natl. Acad. Sci.* 81:6851-6855; Neuberger et al. 1984. *Nature* 312:604-608; Takeda et al. 1985. *Nature* 314:452-454). Alternatively, techniques described for the production of single chain antibodies can be adapted, using methods known in the art, to produce single chain antibodies specific for the polypeptides and fragments of this invention. Antibodies with related specificity, but of distinct idiotypic composition, can be generated by chain shuffling from random combinatorial immunoglobin libraries (Burton 1991. *Proc. Natl. Acad. Sci.* 88:11120-3).

Various immunoassays can be used for screening to identify antibodies having the desired specificity for the proteins and peptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). For example, a two-site, monoclonal-based immunoassay utilizing monoclonal antibodies reactive to two non-interfering epitopes on the proteins or peptides of this invention can be used, as well as a competitive binding assay.

The present invention is more particularly described in the following examples, which are intended as illustrative only since numerous modifications and variations therein will be apparent to those skilled in the art.

EXAMPLES

I. Immunoregulatory Activity of poxvirus A35R Protein

Cell tropism.

Several cell types were split into two groups of equal number for infection. One group was infected with wild-type (Western Reserve or WR) vaccinia virus and the other with the A35R deletion mutant (vaccinia virus that does not contain the A35R protein). Cells were infected at a multiplicity of infection (MOI) of 1. Cells were then incubated approximately 20 hours. Three freeze-thaw cycles were then performed to release newly formed virus particles. Measure of replication was accomplished by titering the cell lysates on a monolayer of BS-C-1 cells and counting the plaques that formed 40 hours later.

Harvest/Infection for Assays.

A 5-9 month old rat (strain: Lewis X from DCM) was injected i.p. with 20 μg of *C. parvum* in 5 ml of HBSS. Three days later the rat was sacrificed and macrophages (peritoneal exudates cells) were harvested. The macrophages were counted and aliquoted in three 15 ml conical tubes prior to a five hour infection incubation at an MOI of 2. Each treatment group was then washed and plated in a 96 well format. Six 1:2 dilutions were performed before incubation with 500 nM GPMBP for 30 minutes. 25,000 Lewis rat CD4+ RSL-11 clones specific for myelin basic protein were added to each well in 80 μl volumes. The plates were incubated for 24 hours at 37° C., 5.0% $CO_2$. After incubation, 150 μl of supernatant were transferred to an empty 96-well plate and frozen for later analysis.

Nitric Oxide Assay.

Fifty microliters of the harvested supernatant were transferred into another 96-well plate followed by the addition of Griess Reagent (1% sulfanilamide-0.1% N-[1-naphthy]ethylenediamine in 2.5% phosphoric acid) into each well. The absorbance was read at 540 nm at time intervals beginning after a five minute incubation at room temperature. Maximum readings were achieved after a 1.5-2 hour incubation.

IL-2 Bioassay.

Fifty microliters of the harvested supernatants were transferred into another 96-well plate. A total of 50,000 CTLL clones (ATCC TIB-214) were washed, resuspended in cRPMI, and added to the wells. After 48 hours of incubation at 37° C., 5.0% $CO_2$, 10 μl of MTS/PMS was added to every sample. The absorbance was read at 492 nm filtered using 690 nm as the reference wavelength.

VA35Δ Mutant Virus.

To construct the VA35Δ mutant virus, wild-type (WR)-infected cells were transfected with a recombinant PCR product containing A34R and A36R flanking sequences with the intervening A35R gene replaced by the *E. coli* gpt gene. The recombinant vA35A was selected in medium containing mycophenolic acid (Roper. 2006. "Characterization of the vaccinia virus A35R protein and its role in virulence" *J. Virol.* 80:306-313; the entire contents of which is incorporated by reference herein for studies to characterize the poxvirus A35R protein).

Cell Tropism.

The growth of wild-type and A35R deletion mutant virus was studied in 18 cell types from six different animals (rats, rabbits, mice, monkeys, hamsters and humans. In one study, the following cell lines were tested: BS-C-1 cells (African green monkey cells), old rat splenocytes, young rat splenocytes, rat thymocytes, differentiated PC-12 cells, undifferentiated PC-12 cells, activated RSL-11 cells, resting RSL-11 cells, PEC, CTLL, brain cells (Heldtilt), HFF cells and R1-T cells. An A35A/wild-type ratio of replication was established. These studies demonstrated that PECs, CTLLs and R1-Ts may have tropism where the deletion mutant had a least a 2-fold greater success replicating than wild-type. Equal replication was consistent in BS-C-1 cells, which were used as the control. Attenuation in mice. Four treatment groups (six mice each) of 14-17 g, 5 week-old female BALB/c mice were anesthetized and intranasally challenged with $10^4$ particle forming units (pfu) of wild type (WR), 35Res (a rescue virus produced by engineering a wild-type A35R gene back into the vA35Δ genome) or 35Del (the vA350 mutant virus), or with PBS. The weight of the mice in each group was measured over a period of days. Over a span of 12 days, the A35R deletion treatment group almost paralleled the PBS control group in that gradual weight gain of 10-11% occurred. The A35-Res and WR groups showed an average weight loss of 16-26%, respectively, by day 12.

Nitric Oxide and IL-2 Bioassay.

Equal volumes of Griess Reagent were added to supernatants to assay nitric oxide in solution. An ELISA plate reader was used to read absorbance. Infected macrophages secreted less nitric oxide than the uninfected macrophages. However, higher levels of nitric oxide produced by the A35A mutant treatment suggests that the presence of the A35R protein inhibits secretion of nitric oxide in infected macrophages. Thus, the presence of A35R in macrophages is associated with inhibiting nitric oxide secretion.

Supernatants were assayed using a cytotoxic T lymphocyte line (CTLL-2), which proliferates based on the concentration of IL-2 in solution. MTS/PMS was added to measure respiration dependent on the amount of proliferation. The absorbance was obtained using an ELISA plate reader. These studies demonstrated that macrophages infected with the A35A mutant stimulated T cells to secrete more IL-2 in solution than both uninfected and wild-type (WR) infected cells. This indicates that the A35R protein restricts the ability of macrophages to stimulate T cells.

Additional studies have not demonstrated any effect of A35R on 1) cytotoxic lymphocyte (CTL) killing; 2) interferon-beta (IFN-β) induced Class I expression in thymocytes; and 3) interferon-gamma (IFN-γ) induced costimulatory molecules (B7.1 molecules) on macrophages.

II. Virulence Activity of poxvirus A35R Protein

Determination of Virulence in Mice.

Groups of six female BALB/c 6-week-old mice were anesthetized and intranasally challenged with $10^4$ to $10^6$ pfu of vA35A, WR, vA35-Res virus, or PBS in 20 μl of 10 mM Tris-HCl (pH 9.0). Virus titers were determined on the day of challenge to confirm virus dose. Individual mice were weighed every two days to monitor health, and mice were sacrificed if they lost 30% of their body weight.

In a second experiment, mice were challenged with $10^5$ and $10^6$ pfu and weighed as described.

The vA35Δ Mutant Virus is Attenuated in Mice.

Over the course of the experiment (14 days), mice challenged with PBS or vA35Δ gained between 10-11% in body weight, whereas mice challenged with $10^4$ pfu of the vA35-Res or VV strain WR lost, on average, 16% and 26% of their body weight, respectively, by day 10. Two WR-challenged mice (and no others) died between days 9 and 11. This experiment was repeated and attenuation of the vA35A was also seen at higher challenge doses. At $10^5$ pfu, one mouse challenged with vA35A died, compared to four with WR and six with vA35-Res. When challenged with $10^6$ pfu, all mice died, but survival was increased by one to two days in the vA35Δ mice. With WR, two mice died on day 6 and four mice died on day 7. When challenged with vA35-Res, all six mice died on day 6; but with vA35A, four mice died on day 7 and two survived until day 8. These data indicate that the A35R protein is important for virulence in mice.

Although the present process has been described with reference to specific details of certain embodiments thereof, it is not intended that such details should be regarded as limitations upon the scope of the invention except as and to the extent that they are included in the accompanying claims.

Throughout this application, various patents and non-patent publications are referenced. The disclosures of these patents and publications in their entireties are hereby incorporated by reference into this application in order to more fully describe the state of the art to which this invention pertains.

TABLE 1

| Viral Orthologous Clusters V2.0 (VOCS) | | |
|---|---|---|
| Virus data | | |
| Virus | Virus name | GenBank Accession No. |
| Vaccinia virus (Tian Tan) | VACV-Tan | AF095689.1 |
| Lumpy skin disease virus (Neethling Warmbaths LW) | LSDV-Warm | AF409137 |
| Lumpy skin disease virus (Neethling vaccine LW 1959) | LSDV-1959 | AF409138 |
| Fowlpox virus (HP1-438 Munich) | FWPV-Munich | AJ581527 |
| Orf virus (NZ2- Sequence 1 from Patent WO03006654) | ORFV-NZ2_Patent | AX754989 |
| Camelpox virus CMS (CMS) | CMLV-CMS | AY009089 |
| Sheeppox virus (A) | SPPV-A | AY077833 |
| Sheeppox virus (NISKHI) | SPPV-NISKHI | AY077834 |
| Goatpox virus (G20-LKV) | GTPV-G20LKV | AY077836 |
| Orf virus (OV-IA82) | ORFV-IA82 | AY386263 |
| Rabbitpox virus (Utrecht) | RPXV-Utr | AY484669 |
| Vaccinia virus (Acambis 3000 Modified Virus Ankara (MVA)) | VACV-Acambis | AY603355 |
| Monkeypox Virus Walter Reed 267 | MPXV-WRAIR | AY603973 |
| Vaccinia virus (LC16m8) | VACV-LC16m8 | AY678275 |
| Vaccinia virus (Lister) | VACV-Lister | AY678276 |
| Vaccinia virus (LC16mO) | VACV-LC16mO | AY678277 |
| Deerpox virus (W-1170-84) | DPV-W84 | AY689437 |
| Monkeypox virus (Sierra Leone) | MPXV-SL | AY741551 |
| Monkeypox virus (COP-58) | MPXV-COP | AY753185 |
| Monkeypox virus (USA_2003_044) | MPXV-USA_2003_044 | DQ011153 |
| Monkeypox virus (Congo_2003_358) | MPXV-Congo_2003_358 | DQ011154 |

TABLE 1-continued

| Viral Orthologous Clusters V2.0 (VOCS) | | |
|---|---|---|
| Monkeypox virus (Zaire_1979-005) | MPXV-Zaire_1979_005 | DQ011155 |
| Monkeypox virus (Liberia_1970_184) | MPXV-Liberia_1970_184 | DQ011156 |
| Monkeypox virus (USA_2003_039) | MPXV-USA_2003_039 | DQ011157 |
| Orf virus (NZ2) | ORFV-NZ2 | DQ184476 |
| Variola major virus (Bangladesh-1975) | VARV-Bsh | L22579.1 |
| Myxoma virus (Lausanne) | MYXV-Laus | NC_001132.2 |
| Shope Rabbit fibroma virus (Kasza) | SFV-Kas | NC_001266 |
| Vaccinia virus (Copenhagen) | VACV-Cop | NC_001559.1 |
| Variola virus (India 3 Major, 1967) | VARV-Ind | NC_001611.1 |
| Molluscum contagiosum virus (subtype 1) | MOCV-1 | NC_001731.1 |
| Melanoplus sanguinipes entomopoxvirus (Tucson) | MSEV-Tuc | NC_001993.1 |
| Fowlpox virus (Virulent-Iowa) | FWPV-Vir_Iowa | NC_002188.1 |
| Amsacta moorei entomopoxvirus (Moyer) | AMEV | NC_002520.1 |
| Yaba-like Disease Virus (Smith) | YLDV | NC_002642 |
| Lumpy skin disease virus (Neethling 2490) | LSDV-Neeth | NC_003027.1 |
| Monkeypox virus (Zaire) | MPXV-Zre | NC_003310.1 |
| Swinepox virus (Nebraska 17077-99) | SWPV-Neb | NC_003389.1 |
| Camelpox virus (Kazakhstan M-96) | CMLV-M96 | NC_003391.1 |
| Cowpox virus (Brighton Red) | CPXV-BR | NC_003663.2 |
| Sheeppox virus (Turkey-TU-V02127) | SPPV-TU | NC_004002 |
| Goatpox virus (Pellor) | GTPV-Pellor | NC_004003 |
| Ectromelia virus (Moscow) | ECTV-Mos | NC_004105.1 |
| Yaba monkey tumor virus YMTV | NC_005179 | |
| Canarypox virus (ATCC VR-111) | CNPV | NC_005309 |
| Orf virus (OV-SA00) | ORFV-SA00 | NC_005336 |
| Bovine papular stomatitis virus (BV-AR02) | BPSV-AR02 | NC_005337 |
| Deerpox virus (W-848-83) | DPV-W83 | NC_006966 |
| Vaccinia virus (Western Reserve) | VACV-WR | NC_006998 |
| Ectromelia virus (Naval) | ECTV-Nav | PBR |
| Vaccinia virus (Modified Vaccinia Ankara) | VACV-MVA | U94848.1 |
| Cowpox virus (GRI-90) | CPXV-GRI | X94355 |
| Variola minor virus (Garcia-1966) | VARV-Gar | Y16780.1 |

| Genes in family "Unknown (Cop-A35R)" | | | | | |
|---|---|---|---|---|---|
| Gene name | GenBank Accession | Virus name | ORF start | ORF stop | No. of amino acids |
| MOCV-1-145R | 9629077 | MOCV-1 | 163178 | 163879 | 233 |
| MYXV-Lau-m123R | 9633759 | MYXV-Laus | 116937 | 117476 | 179 |
| SFV-Kas-s123R | 6578652 | SFV-Kas | 116088 | 116627 | 179 |
| VARV-Gar-A39R | 5830703 | VARV-Gar | 136286 | 136468 | 60 |
| VARV-Ind-A38R | 9627663 | VARV-Ind | 135262 | 135444 | 60 |
| VACV-MVA-146R | 2772791 | VACV-MVA | 135418 | 135948 | 176 |
| VACV-Cop-A35R | 335511 | VACV-Cop | 143448 | 143978 | 176 |
| VACV-Tan-TA45R | 6969831 | VACV-Tan | 144144 | 144674 | 176 |
| YLDV-124R | 12085107 | YLDV | 115059 | 115598 | 179 |
| LSDV-Nee-124 | 15150563 | LSDV-Neeth | 114604 | 115179 | 191 |
| MPXV-Zre-A37R | 17975060 | MPXV-Zre | 144036 | 144566 | 176 |
| SWPV-Neb-121 | 18640207 | SWPV-Neb | 112809 | 113366 | 185 |
| CMLV-M96-154 | 18640388 | CMLV-M96 | 146790 | 147320 | 176 |
| ECTV-Mos-137 | 22164743 | ECTV-Mos | 152897 | 153427 | 176 |
| RPXV-Utr-143 | 44971506 | RPXV-Utr | 149272 | 149805 | 177 |
| SPPV-TU-119 | 21492576 | SPPV-TU | 114222 | 114797 | 191 |
| CPXV-BR-171 | 20178533 | CPXV-BR | 161528 | 162058 | 176 |

TABLE 1-continued

Viral Orthologous Clusters V2.0 (VOCS)

| | | | | | |
|---|---|---|---|---|---|
| CMLV-CMS-152R | 19718123 | CMLV-CMS | 144907 | 145437 | 176 |
| LSDV-1959-124 | 22595817 | LSDV-1959 | 114440 | 115015 | 191 |
| LSDV-Warm-124 | 22595659 | LSDV-Warm | 114610 | 115185 | 191 |
| ECTV-Nav-157 | 0 | ECTV-Nav | 150677 | 151207 | 176 |
| VACV-WR-158 | 66275955 | VACV-WR | 144462 | 144992 | 176 |
| CPXV-GRI-A36R | 30519528 | CPXV-GRI | 160934 | 161464 | 176 |
| YMTV-124R | 38229287 | YMTV | 109364 | 109942 | 192 |
| ORFV-NZ2_Patent-113 | 32167505 | ORFV-NZ2_Patent | 111949 | 112488 | 179 |
| BPSV-AR02-110 | 41018863 | BPSV-AR02 | 112527 | 113081 | 184 |
| ORFV-AI82-108 | 41018598 | ORFV-IA82 | 111489 | 112085 | 198 |
| ORFV-SA00-108 | 41018731 | ORFV-SA00 | 112723 | 113262 | 179 |
| VACV-Acambis-148 | 47088474 | VACV-Acambis | 129628 | 130158 | 176 |
| MPXV-WRAIR-141 | 0 | MPXV-WRAIR | 144107 | 144637 | 176 |
| SPPV-A-119 | 0 | SPPV-A | 114198 | 114773 | 191 |
| SPPV-NISKHI-119 | 0 | SPPV-NISKHI | 114001 | 114576 | 191 |
| GTPV-Pellor-119 | 0 | GTPV-Pellor | 113955 | 114530 | 191 |
| GTPV-G20LKV-119 | 0 | GTPV-G20LKV | 114018 | 114593 | 191 |
| DPV-W83-134 | 0 | DPV-W83 | 123533 | 124078 | 181 |
| DPV-W84-134 | 0 | DPV-W84 | 126583 | 127128 | 181 |
| VACV-LC16m8-m8202R | 56713552 | VACV-LC16m8 | 147115 | 147645 | 176 |
| VACV-LC16mO-mO202R | 56713836 | VACV-LC16mO | 147114 | 147644 | 176 |
| VACV-Lister-m8202R | 0 | VACV-Lister | 146991 | 147521 | 176 |
| MPXV-COP-141 | 59858947 | MPXV-COP | 144350 | 144880 | 176 |
| MPXV-SL-141 | 58220611 | MPXV-SL | 144152 | 144682 | 176 |
| MPXV-USA_2003_044-155 | 68448826 | MPXV-USA_2003_044 | 144173 | 144703 | 176 |
| MPXV-Zaire_1979_005-155 | 68449229 | MPXV-Zaire_1979_010454145 | 144675 | 176 | |
| MPXV-Congo_2003_358-155 | 68449027 | MPXV-Congo_2003_315484176 | 144706 | 176 | |
| MPXV-Liberia_1970_184-155 | 68449428 | MPXV-Liberia_1970_114844596 | 145126 | 176 | |
| MPXV-USA_2003_039-155 | 68449628 | MPXV-USA_2003_039 | 144173 | 144703 | 176 |
| ORFV-NZ2-111 | 74230824 | ORFV-NZ2 | 111955 | 112494 | 179 |

TABLE 2

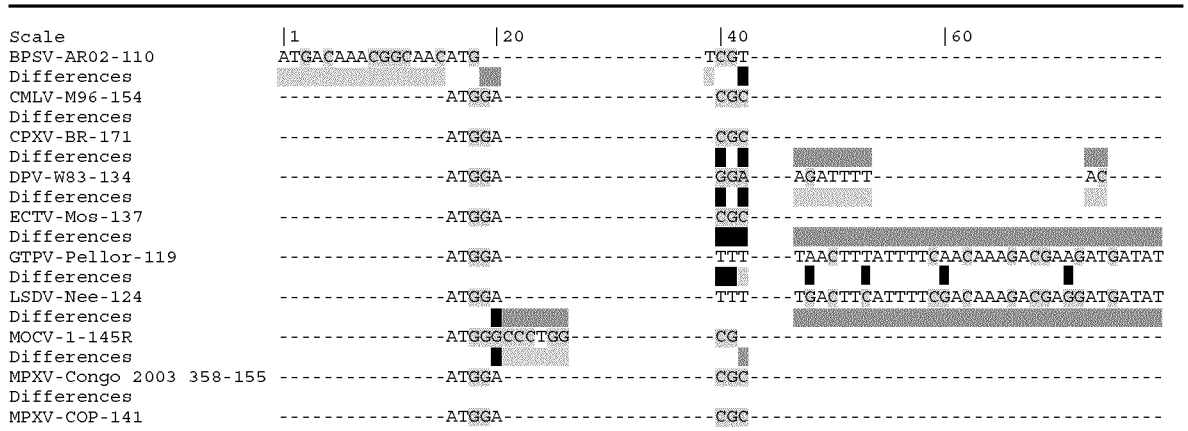

TABLE 2-continued

```
Differences
MPXV-Zre-A37R              ---------------ATGGA------------------CGC-------------------------------
Differences
MYXV-Lau-m123R             ---------------ATGGA------------------CGC----CGAT-----------------AGAAT-----
Differences
ORFV-NZ2 Patent-113        ---------------ATG--------------------TCGC-----------------------------------
Differences
RPXV-Utr-143               ---------------ATGGA------------------CGC-------------------------------
Differences
SFV-Kas-s123R              ---------------ATGGA------------------CGC----CGAT-----------------AGAAT-----
Differences
SPPV-TU-119                ---------------ATGGA------------------TTT----TGACTTCATTTTCAACAAAGACGAGGATGATAT
Differences
SWPV-Neb-121               -------ATGTATCAATGGAT-----------------CGT----CGAT-----------------ATGGC--TAC
Differences
VACV-Acambis-148           ---------------ATGGA------------------CGC-------------------------------
Differences
VACV-Cop-A35R              ---------------ATGGA------------------CGC-------------------------------
Differences
VACV-LC16m8-m8202R         ---------------ATGGA------------------CGC-------------------------------
Differences
VACV-MVA-146R              ---------------ATGGA------------------CGC-------------------------------
Differences
VACV-WR-158                ---------------ATGGA------------------CGC-------------------------------
Differences
YLDV-124R                  ---------------ATGGAAA----------------TCGC----CGGTT---------------------
Differences
YMTV-124R                  ---------------ATGAAAAGTTATAGTGTGTTTATCCACAATACGATTG---------------AAAAC---AT
Scale                      |1              |20                   |40                 |60

Scale                      |80                |100                 |120                 |140
BPSV-AR02-110              ----GCCTTCAAATACTCACTCCATTTGGACTAATCTTCGCACCCGACGATGTTCGGCTGCGTGAGATCGCGCT-GGAA
Differences
CMLV-M96-154               ---CGCGTTTG--TTATTACTCCAATGGGTGTGTTGACTATAACAGAT---------------ACATTATATTATGAT
Differences
CPXV-BR-171                ---CGCGTTTG--TTATTACTCCAATGGGTGTGTTGACTATAACAGAT---------------ACATTGTATGATGAT
Differences
DPV-W83-134                ----AACATTGT--TAACTGTTTTA----GGAACTATGAGAATTGAAAAT---AAGAATCTC-ATAAAACCTATGATGAT
Differences
ECTV-Mos-137               ---CGCGTTTG--TTATTACTCCAATGGGTGTGTTGACTATAACAGAT---------------ACATTATATGAGGAT
Differences
GTPV-Pellor-119            TTATACGTTAA--TAACAACTTTA---GGTGTATTAAAAATAAAAAAG---AAAGAAATA-TCAAAAGTTTGTAGTGAT
Differences
LSDV-Nee-124               TTATACGTTAA--TAACAACTTTA---GGTGTATTAAAAATAAAAAAG---AAAGAAATA-TCAAAAGTTTGTAGTGAG
Differences
MOCV-1-145R                ----GCTTTCCTGTCATCACCCCGCTGGGCCGCATGCACCTACGCGCCGACATGCGCACGCGCGTCAT-GTGCGTGGAC
Differences
MPXV-Congo 2003 358-155    ---CGCGTTTG--TTATTACTCCAATGGGTGTGTTGACTATAACAGAT---------------ACATTGTATGATGAT
Differences
MPXV-COP-141               ---CGCGTTTG--TTATTACTCCAATGGGTGTGTTGACTATAACAGAT---------------ACATTGTATGATGAT Differences
MPXV-Zre-A37R              ---CGCGTTTG--TTATTACTCCAATGGGTGTGTTGACTATAACAGAT---------------ACATTGTATGATGAT
Differences
MYXV-Lau-m123R             ---TACGTGCG--TGACGGCCCTA---GGCGTGTTATATACGTCAC---GACGAGATA-GACACGGTGCGTTCTGAA
Differences
ORFV-NZ2 Patent-113        ----GACTTCAAATACTGACCTCATTTGGACAAATCTTCGCACCCGACGAAGCTCGGCTGCGCGAGATCGCGCG-TGAT
Differences
RPXV-Utr-143               ---CGCGTTTG--TTATTACTCCAATGGGTGTGTTGACTATAACAGAT---------------ACATTGTATGATGAT
Differences
SFV-Kas-s123R              ----AACGTGCG--TGACAGCCCTA---GGCGTGTTGTCTATACACCAC---GACGAGATG-AACATGGTGTGTTCTGAA
Differences
SPPV-TU-119                TTATACGTTAA--TAACAACTTTA---GGTGTATTAAAAATAAAAAAA---AAAGAAATA-TCAAAGTTTGTAGTGAA
Differences
SWPV-Neb-121               CTATACATTCG--TAACATCATTG---GGTGTATTGAAACTATCAGAA---GATAATGTA-TCAAGATCGTTCTCAGAT
Differences
VACV-Acambis-148           ---CGCGTTTG--TTATTACTCCAATGGGTGTGTTGACTATAACAGAT---------------ACATTGTATGATGAT
Differences
VACV-Cop-A35R              ---CGCGTTTG--TTATTACTCCAATGGGTGTGTTGACTATAACAGAT---------------ACATTGTATGATGAT
Differences
VACV-LC16m8-m8202R         ---CGCGTTTG--TTATTACTCCAATGGGTGTGTTGACTATAACAGAT---------------ACATTGTATGATGAT
Differences
VACV-MVA-146R              ---CGCGTTTG--TTATTACTCCAATGGGTGTGTTGACTATAACAGAT---------------ACATTGTATGATGAT
Differences
VACV-WR-158                ---CGCGTTTG--TTATTACTCCAATGGGTGTGTTGACTATAACAGAT---------------ACATTGTATGATGAT
Differences
YLDV-124R                  --ATAATTTTA--TAATTACTCATTTGGAGTAATAAAAATACATAGTGTAAATCATTTT-AAGACTGTATGTGAGGAT
Differences
YMTV-124R                  GTATAATGTCG--TTATTACTTCATTTGGAGTAATAAATATATACGGTTTTGAACATTTA-AAAACCGTATGTGAAGAT
Scale                      |80                |100                 |120                 |140
```

TABLE 2-continued

| Scale | \|160 | \|180 | \|200 | \|220 |
|---|---|---|---|---|
| BPSV-AR02-110 | CTGGGGATCACCTA | -----CGTTTCCCGCGCATTCGGAGAC | ---ATGTTGT-ACGGCGA | -GATGTCGTTCACCTCCTTA |
| Differences | | | | |
| CMLV-M96-154 | CTTGATATCTCAAT | -----AATG----GACTTTATAGGACC | ---ATACATT-ATAGGTAACATAAAAACTGTCCAAATA | |
| Differences | | | | |
| CPXV-BR-171 | CTTGATATCTCAAT | -----CATG----GACTTTATAGGACC | ---ATACATC-ATAGGTAACATAAAAACTGTCCAAATA | |
| Differences | | | | |
| DPV-W83-134 | TTGGGTATAAACAT | -----TGTT----GATGATTTTGGACC | ---CTATAAA-CTCGCATCTTTGGAAATTTCTTTAGTT | |
| Differences | | | | |
| ECTV-Mos-137 | CTCGATATCTCAAT | -----AATA----GACTTTATAGGACC | ---ATATATT-ATAGGTAACATAAAAACTGTCCAAATA | |
| Differences | | | | |
| GTPV-Pellor-119 | CTAGACATTAATCT | -----TATA----GAAACATTAGGACC | ---TTATAAC-GTAGTATCTTTAAATATATACCCATTT | |
| Differences | | | | |
| LSDV-Nee-124 | CTAGGAATTAATCT | -----TATA----GAAACATTAGGACC | ---TTATAAC-GTAGTATCTTTAAATATACACCCATTT | |
| Differences | | | | |
| MOCV-1-145R | TTTGGCGTGACCATGGACACGCT | ----GCGCGTGCTGGGCCCCTACGTGGTCATGGTGCCCATG | ---CTCGAGCCTGCC | |
| Differences | | | | |
| MPXV-Congo 2003 358-155 | CTCGATATCTCAAT | -----CATG----GACTTTATAGGACC | ---ATACATT-ATAGGTAACATAAAAATTGTCCAAATA | |
| Differences | | | | |
| MPXV-COP-141 | CTCGATATCTCAAT | -----CATG----GACTTTATAGGACC | ---ATACATT-ATAGGTAACATAAAAATGTCCAAATA | |
| Differences | | | | |
| MPXV-Zre-A37R | CTCGATATCTCAAT | -----CATG----GACTTTATAGGACC | ---ATACATT-ATAGGTAACATAAAAATGTCCAAATA | |
| Differences | | | | |
| MYXV-Lau-m123R | CTGGGAATAACGTT | -----CATA----GGAGACGTGGGACC | ---GTATCGT-GTAGCGACTTTAAATATTTGTCCGGTG | |
| Differences | | | | |
| ORFV-NZ2 Patent-113 | TTGGGAATATGCAC | -----CATAAAACGCGCATTCGGCGAC | ---ATGCTGT-ACGGCTT-TATAGACTTCGACCCGGTG | |
| Differences | | | | |
| RPXV-Utr-143 | CTCGATATCTCAAT | -----CATG----GACTTTATAGGACC | ---ATACATT-ATAGGTAACATAAAAACTGTCCAAATA | |
| Differences | | | | |
| SFV-Kas-s123R | CTGGGAATTACATT | -----CATA----GGAGACATTGGACC | ---GTATCGC-GTGGCGACTTTAAATATTTGTCCGGTG | |
| Differences | | | | |
| SPPV-TU-119 | CTAGACATTAATTT | -----TATA----GAAACATTAGGACC | ---TTATAAT-GTAGTATCTTTAAATATACACCCATTT | |
| Differences | | | | |
| SWPV-Neb-121 | TTAGGCATTACCAT | -----TATT----GATCGTATAGGTCC | ---ATATCAT-ATAGCATCGATAGAATTACATTCTATT | |
| Differences | | | | |
| VACV-Acambis-148 | CTCGATATCTCAAT | -----CATG----GACTTTATAGGACC | ---ATACATT-ATAGGTAACATAAAAACTGTCCAAATA | |
| Differences | | | | |
| VACV-Cop-A35R | CTCGATATTTCATT | -----CATG----GACTTTATAGGACC | ---ATACATT-ATAGGTAACATAAAAACTGTCCAAATA | |
| Differences | | | | |
| VACV-LC16m8-m8202R | CTCGATATCTCAAT | -----CATG----GACTTTATAGGACC | ---ATACATT-ATAGGTAACATAAAAACTGTCCAAATA | |
| Differences | | | | |
| VACV-MVA-146R | CTCGATATCTCAAT | -----CATG----GACTTTATAGGACC | ---ATACATT-ATAGGTAACATAAAAACTGTCCAAATA | |
| Differences | | | | |
| VACV-WR-158 | CTCGATATCTCAAT | -----CATG----GACTTTATAGGACC | ---ATACATT-ATAGGTAACATAAAAACTGTCCAAATA | |
| Differences | | | | |
| YLDV-124R | TTAGGCATCGTTAT | -----TGTT----GACTATATAGGTGA | ---ATACGCA-ATAGCGACGTTAGAAGTTCAAGAAATA | |
| Differences | | | | |
| YMTV-124R | TTAGGTATTGTTGT | -----TTTT----GACTTTGTAGGA A | ---GTACGCC-AT GCAACATTAAA G CAAGAAATA | |
| Scale | \|160 | \|180 | \|200 | \|220 |

| Scale | \|240 | \|260 | \|280 | \|300 |
|---|---|---|---|---|
| BPSV-AR02-110 | CCCATGAAC--GAGGTGCCCGCGT | ---GCGTGTCGGACTGCTACCTTGCCGTGAACGGGAACCTCAT | ---ACCGTGCAC | |
| Differences | | | | |
| CMLV-M96-154 | GATGTACGG--GATATAAATATTCCGACATGCAAAAATGCTACTTTAGCTATAAGGGTAAAATAGTTCCTCAAGATTC | | | |
| Differences | | | | |
| CPXV-BR-171 | GATGTACGG--GATATAAATATTCCGATATGCAAAAATGCTACTTTAGCTATAAGGGTAAAATAGTTCCTCAGGATTC | | | |
| Differences | | | | |
| DPV-W83-134 | TCTTCAGAATTGTTAAAAACCTAT--GATTTACAGGATTGTTATATAGCCCATAATGGAATTGTGTT---ACATTGTTC | | | |
| Differences | | | | |
| ECTV-Mos-137 | GATGTATGG--GATATAAATATTCCGACATGCAAAAATGCTACTTTAGCTATAAGGGTAAAATAGTTCCTCAGGATTC | | | |
| Differences | | | | |
| GTPV-Pellor-119 | CCTAACAA--TTTCATGAACAATCAAATTTGATTAACTGCTATATATCTTATAATGGGACACTGTT---TCACTGTTC | | | |
| Differences | | | | |
| LSDV-Nee-124 | CCTAACAA--TTTCATAGAACAATCAAATTTGATTAATTGTTATATATCTTATAATGGGACACTGTT---TCACTGTTC | | | |
| Differences | | | | |
| MOCV-1-145R | AGCGCCAGC--CTGCTGGCACCGCGCGCGCTCCGAGACTGCTACGTCGCGGCGCACGGTGTGCTACT---GCACTGCAG | | | |
| Differences | | | | |
| MPXV-Congo 2003 358-155 | GATGCACGG--GATATAAATATTCCGACATGCAAAAATGCTACTTTAGCTATAAGGGTAAAATAGTTCCTCAGGATTC | | | |
| Differences | | | | |
| MPXV-COP-141 | GATATACGG--GATATAAATATTCCGACATGCAAAAATGCTACTTTAGCTATAAGGGTAAAATAGTTCCTCAGGATTC | | | |

TABLE 2-continued

| Name | Sequence |
|---|---|
| Differences | |
| MPXV-Zre-A37R | GATGCACGC--GATATAAAATATTCCGACATGCAAAAATGCTACTTTAGCTATAAGGGTAAAATAGTTCCTCAGGATTC |
| Differences | |
| MYXV-Lau-m123R | GCGTTAGA--CGATGTATACCAACGAGGCGTGACTAATTGTTACATCGTCAGTGACGGAAGGATTAC---ACGCTGTTC |
| Differences | |
| ORFV-NZ2 Patent-113 | CCCCTGACC--CAAGTAAACATGC----TCATGTCCAACTGCTACTTCGCGGTCAACGGCAACCTGCT---TCCGTGCAC |
| Differences | |
| RPXV-Utr-143 | GATGTACGG--GATATAAAATATTCCGACATGCAAAAATGCTACTTTAGCTATAAGGGTAAAATAGTTCCTCAGGATTC |
| Differences | |
| SFV-Kas-s123R | GCGTTCGA--TGATGTACATCAACGTGGCGTGATTAACTGTTTATATCGTCAGTGATGAAGGATTAT---ACGCTGTTC |
| Differences | |
| SPPV-TU-119 | CCTAACAA--TTTTATAGAACAATCAAATTTGATTAACTGTTATATATCTTATAATGGGAGACTGTT---TCACTGTTC |
| Differences | |
| SWPV-Neb-121 | CCAATGGAG--TATATAACACAAAAAGATTTAGAAAAATGTTATATAGTTCATAATGGTTTGATATT---ACAATGCTC |
| Differences | |
| VACV-Acambis-148 | GATGTACGG--GATATAAAATATTCCGACATGCAAAAATGCTACTTTAGCTATAAGGGTAAAATAGTTCCTCAGGATTC |
| Differences | |
| VACV-Cop-A35R | GATGTACGG--GATATAAAATATTCCGACATGCAAAAATGCTACTTTAGCTATAAGGGTAAAATAGTTCCTCAGGATTC |
| Differences | |
| VACV-LC16m8-m8202R | GATGTACGG--GATATAAAATATTCCGACATGCAAAAATGCTACTTTAGCTATAAGGGTAAAATAGTTCCTCAGGATTC |
| Differences | |
| VACV-MVA-146R | GATGTACGG--GATATAAAATATTCCGACATGCAAAAATGCTACTTTAGCTATAAGGGTAAAATAGTTCCTCAGGATTC |
| Differences | |
| VACV-WR-158 | GATGTACGG--GATATAAAATATTCCGACATGCAAAAATGCTACTTTAGCTATAAGGGTAAAATAGTTCCTCAGGATTC |
| Differences | |
| YLDV-124R | AATGTAAA--CCTTATTAACCAAAATGATATATACGATTGTTACGTAGCGTGTAATGGTTTTATAGT---AAACTGTTC |
| Differences | |
| YMTV-124R | AGCGTAAA--CCTTATTACACAAGATGATATAAACGACTGTTATATAGCATGTAACGGTTTTATAGT---AAAATGTTC |
| Scale | \|240     \|260     \|280     \|300 |

| Name | Sequence |
|---|---|
| Scale | \|320     \|340     \|360     \|380 |
| BPSV-AR02-110 | GGAGTCCTTCAGGCTTCGGATACCCATGGACGGCG-TTAAGGCGGCCTACCGCACAGGCACCGGCAAGACGAT---CCT |
| Differences | |
| CMLV-M96-154 | TAATGAT--TTGGCTAGATTCAAC-ATTTATAGCA-TTTGTGCCGCATACAGATCAAAAAATAATCATCAT---AGC |
| Differences | |
| CPXV-BR-171 | TAATGAT--TTGGCTAGATTCAAC-ATTTATAGCA-TTTGTGCTGCATACAGATCAAAAAATACCATCATCAT---AGC |
| Differences | |
| DPV-W83-134 | TTCTGATAATAAATTAAAATATACCGGTATATAAAG-TGTATTCTGTATATATGTCTAAGAAAAGCATAATTAT---TTG |
| Differences | |
| ECTV-Mos-137 | TAATGAT--TTGGCTAGATTCAAC-ATTTATAGCA-TTTGTGCAGCATACAGATCAAAAAATACCATCATCAT---AGC |
| Differences | |
| GTPV-Pellor-119 | TAAAGATGAAAGACTGAGTATCCCAATAAATGGCT-TGTATAGAGGGTTTTACTCTAACAATAGTTTTATATT---TTC |
| Differences | |
| LSDV-Nee-124 | TAAAGATGAAAGACTGAGTATCCCAATAAATGGCT-TGTATAGAGGGTTTTACTCTAACAATAGTTTTATATT---TTC |
| Differences | |
| MOCV-1-145R | CGAGCTCGCGTACCTGTGCGCGCCCATGACACGCA-TCTTCGCCGTCTTTCGGCGCGCCGCCGCTACGTGCT---CTG |
| Differences | |
| MPXV-Congo 2003 358-155 | TAATGAT--TTGGCTAGATTCAAC-ATTTATAGTA-TTTGTACCGCATACAGATCAAAAAATACCATCATCAT---AGC |
| Differences | |
| MPXV-COP-141 | TAATGAT--TTGGCTAGATTCAAC-ATTTATAGTA-TTTGTACCGCATACAGATCAAAAAATACCATCATCAT---AGC |
| Differences | |
| MPXV-Zre-A37R | TAATGAT--TTGGCTAGATTCAAC-ATTTATAGTA-TTTGTACCGCATACAGATCAAAAAATACCATCATCAT---AGC |
| Differences | |
| MYXV-Lau-m123R | TAATCAATACAGGTTAACATTTCCTATACACAAGG-TGTATACGGTGTATAAATCTATTAATAGTTTTATGTT---GTG |
| Differences | |
| ORFV-NZ2 Patent-113 | GGAGGACTTCCGGCT-CAGACTCCCGGCAACGGAGATCTCTGCGGCCTACCTGACGAGAACGGGACGGACGAT---CCT |
| Differences | |
| RPXV-Utr-143 | TAATGAT--TTGGCTAGATTCAAC-ATTTATAGCA-TTTGTGCCGCATACAGATCAAAAAATACCATCATCATCATAGC |
| Differences | |
| SFV-Kas-s123R | TAACCAGTACAGGCTAGCATTTCCCATACACAAGG-TATATACGGTGTATAAATCTATTAATAGTTTTATGTT---TTG |
| Differences | |
| SPPV-TU-119 | TAAAGATGAAAGACTGAGTATCCCAATAAATGGAT-TGTATAGAGGGTTTTACTCTAATAATAGTTTTATATT---TTC |
| Differences | |
| SWPV-Neb-121 | TAAAGATAATAATCTAAATATGCATGTTCATAATG-TACATCGCGCTTATCATTCTGTTAATAGTTGCATATT---ATG |
| Differences | |
| VACV-Acambis-148 | TAATGAT--TTGGCTAGATTCAAC-ATTTATAGCA-TTTGTGCCGCATACAGATCAAAAAATACCATCATCAT---AGC |
| Differences | |
| VACV-Cop-A35R | TAATGAT--TTGGCTAGATTCAAC-ATTTATAGCA-TTTGTGCCGCATACAGATCAAAAAATACCATCATCAT---AGC |
| Differences | |
| VACV-LC16m8-m8202R | TAATGAT--TTGGCTAGATTCAAC-ATTTATAGCA-TTTGTGCCGCATACAGATCAAAAAATACCATCATCAT---AGC |
| Differences | |
| VACV-MVA-146R | TAATGAT--TTGGCTAGATTCAAC-ATTTATAGCA-TTTGTGCCGCATACAGATCAAAAAATACCATCATCAT---AGC |
| Differences | |
| VACV-WR-158 | TAATGAT--TTGGCTAGATTCAAC-ATTTATAGCA-TTTGTGCCGCATACAGATCAAAAAATACCATCATCAT---AGC |
| Differences | |
| YLDV-124R | TAAGTTAAATAATGTTCCGTTTCCCGTAACACAGG-TATATTATGCATTTCTTACAAAAACAAAATATTATT---ATG |
| Differences | |
| YMTV-124R | TGAGTATAACAAGGTTCCGTTTCCCGTAATACAGA-TATATTGTGCTTTTCTTACAAAGAGCAAAATTTTATT---ATG |
| Scale | \|320     \|340     \|360     \|380 |

TABLE 2-continued

```
Scale                          |400              |420              |440              |460
BPSV-AR02-110                  CTGCGGCCCCGA-----ATTCAACGTCGTGAACCCCTCCGGCTTTCGTCCGGCCCTGCGGCTCCGCGAGCTCAGCCAC-
Differences
CMLV-M96-154                   ATGTGACTATG------ATATCATGTTAGATAT------AGAATGTAAACATCAGCCATTTTATCTATTCCCATCTAT-
Differences
CPXV-BR-171                    ATGCGACTATG------ATATCATGTTAGATAT------AGAAGGTAAACATCAGCCATTTTATCTATTCCCATCTAT-
Differences
DPV-W83-134                    TTTTGATGAA-------TGTCCAAAATTGTTTAT------AGATGGAAAATCTCAACCTTTCTATATTTTATCTTCTTCA
Differences
ECTV-Mos-137                   ATGCGACTATG------ATATCATGTTAGATAT------AGAAGGTAAACATCAGCCATTTTATCTATTCCCATCTAT-
Differences
GTPV-Pellor-119                TTTTGATAAAGAAAATTATGGTAAGCTACTAAT------TGATGAAAAAGAACAATATTTTTACCTAGGGACAGC-ATA
Differences
LSDV-Nee-124                   TTTTGATAAAGAAAATTATGGTAAGCTACTAAT------TGATGAAAAAGAACAATATTTTTACCTAGGGACAGC-ATA
Differences
MOCV-1-145R                    CTGCGACGAC-------TACGACGTGCTGCGCACGCACGTGGGCGGCTCTGCCTTCAGCGTGCGCAGGTTCACAGACG
Differences
MPXV-Congo 2003 358-155        ATGCGACTATG------ATATCATGTTAGATAT------AGAAGGTAAACATCAACCATTTTATCTATTCCCATCTAT-
Differences
MPXV-COP-141                   ATGCGACTATG------ATATCATGTTAGATAT------AGAAGGTAAACATCAACCATTTTATCTATTCCCATCTAT-
Differences
MPXV-Zre-A37R                  ATGCGACTATG------ATATCATGTTAGATAT------AGAAGGTAAACATCAACCATTTTATCTATTCCCATCTAT-
Differences
MYXV-Lau-m123R                 TTTCGATAAA-------TGTTTCAAATTACGCAT------AGATAACAATCCCAAGATTTCTTCATCACATCGTCTATA
Differences
ORFV-NZ2 Patent-113            GTGCGGCAAAGA-----CTTCAACATAGTAGCGCCGTCGGGGTTCAAGCCGTCCATGCGGCTGCGCGACCTCAGTCAC-
Differences
RPXV-Utr-143                   ATGCGACTATG------ATATCATGTTAGATAT------AGAAGATAAACATCAGCCATTTTATCTATTCCCATCTAT-
Differences
SFV-Kas-s123R                  TTTTGATAAA-------TGTTTCAAATTACACAT------AGATACCAACCACCAAGATTTCTTCATTACGTCATCTATA
Differences
SPPV-TU-119                    TTTTGATAAAGAAAATTATGGTAAGTTACTAAT------TGATGAAAAAAACAATATTTTTACCTAGGCACAGC-ATA
Differences
SWPV-Neb-121                   TTTCGATAGA-------TATCCGAGGCTTAGTTT------GGAGGGAAAATATCAACCTTTTTATATATCAACATCTACA
Differences
VACV-Acambis-148               ATGCGACTATG------ATATCATGTTAGATAT------AGAAGATAAACATCAGCCATTTTATCTATTCCCATCTAT-
Differences
VACV-Cop-A35R                  ATGCGACTATG------ATATCATGTTAGATAT------AGAAGATAAACATCAGCCATTTTATCTATTCCCATCTAT-
Differences
VACV-LC16m8-m8202R             ATGCGACTATG------ATATCATGTTAGATAT------AGAAGATAAACATCAGCCATTTTATCTATTCCCATCTAT-
Differences
VACV-MVA-146R                  ATGCGACTATG------ATATCATGTTAGATAT------AGAAGATAAACATCAGCCATTTTATCTATTCCCATCTAT-
Differences
VACV-WR-158                    ATGCGACTATG------ATATCATGTTAGATAT------AGAAGATAAACATCAGCCATTTTATCTATTCCCATCTAT-
Differences
YLDV-124R                      TTGCGATAAA-------TATCCAAAACTATCAAT------AAACAATAAAATACAGCCATTTTACATTTCTTCTTCCAT-
Differences
YMTV-124R                      TTGTGATTAT-------CACCCAAAACTGTTTGT------GGATAACATGTTACAACCGTTTTATATTTCTTTCTCTAT-
Scale                          |400              |420              |440              |460

Scale                          |480              |500              |520              |540
BPSV-AR02-110                  ---GTGGCGGCGCATACAGAGATCTTAGAGCTGTAC------TCGGAGTCCGGCAACTACGAGTTCATCATGGGGCCAA
Differences
CMLV-M96-154                   --TGATGTTTTTAACGCTACAATAATAGAAGCGTATAACCTGTATACAGCTGGAGATTATCATCTGATCATCAATCCTT
Differences
CPXV-BR-171                    --TGATGTTTTTAACGCTACAATCATAGAAGCGTATAACCTGTACACAGCTGGAGATTATCATCTGATCATCAATCCTT
Differences
DPV-W83-134                    T-TAATGATG--GATGCGCATATTATTGAAGTGTATAATTTATATGATGAGGGTGATTATCATATTATTTTAAACCCTT
Differences
ECTV-Mos-137                   --TGATGTTTTTAACGCTACAATCATAGAAGCGTATAATCTGTATACAGCTGGAGATTATCATCTGATCATCAATCCTT
Differences
GTPV-Pellor-119                --TGATAGTTAATTCAAATATCATTGAAGTGTATAATTTATACAGGAAAGGAGATTACAATTTTATTATAAATCCAT
Differences
LSDV-Nee-124                   --TGATATAGTTAATTCAAATATCATCGAAGTGTATAATTTATACAGGAAAGGAGATTACAATTTTATTATAAATCCAT
Differences
MOCV-1-145R                    C-GGACTTCGAGCGCGTGCGCGTGCTCGAGCTCTACAACTACAACTACTGCGGCGAGTACCAGTTGGTGCTGCTGCCCT
Differences
MPXV-Congo 2003 358-155        --TGATGTTTTTAACGCTACAATCATAGAAGCGTATAATCTGTATACAGCTGGAGATTATCATCTGATCATCAATCCTT
Differences
MPXV-COP-141                   --TGATGTTTTTAACGCTACAATCATAGAAGCGTATAATCTGTATACAGCTGGAGATTATCATCTGATCATCAATCCTT
```

TABLE 2-continued

```
Differences
MPXV-Zre-A37R              --TGATGTTTTTAACGCTACAATCATAGAAGCGTATAATCTGTATACAGCTGGAGATTATCATCTGATCATCAATCCTT
Differences
MYXV-Lau-m123R             G-CGATTCAG--GACGCGCGGGTACTCGAAGTGTACAACCTGTATAAGAAAGGGGACTATCATCTCATTCTCAATCCCA
Differences
ORFV-NZ2 Patent-113        ---GTGTCTGCGCTTGTAGAGATCCTGGAAGTCTAC------GACGAGTCCGGGGAGTACCAATTCGTGCTCGGCCCCA
Differences
RPXV-Utr-143               --TGATGTTTTTAACGCTACAATCATAGAAGCGTATAACCTGTATACAGCTGGAGATTATCATCTAATCATCAATCCTT
Differences
SFV-Kas-s123R              G-CGATTCAG--GATGCACGATCCTTGAAGTGTACAACCTTTACAAGAAAGGGGACTACCATTTCATTCTCAATCCCA
Differences
SPPV-TU-119                --TGATATAGTTAATTCAAATATCATCGAAGTGTATAATTTATACAGGAAAGGAGATTACAATTTTATTATAAGTCCAT
Differences
SWPV-Neb-121               TGCATTACTGCTAAT---AGTATAATGGAAGTTTATAATTTTGAATAAAAAAGATGATTATGAATTTATTATAAATCCAT
Differences
VACV-Acambis-148           --TGATGTTTTTAACGCTACAATCATAGAAGCGTATAACCTGTATACAGCTGGAGATTATCATCTAATCATCAATCCTT
Differences
VACV-Cop-A35R              --TGATGTTTTTAACGCTACAATCATAGAAGCGTATAACCTGTATACAGCTGGAGATTATCATCTAATCATCAATCCTT
Differences
VACV-LC16m8-m8202R         --TGATGTTTTTAACGCTACAATCATAGAAGCGTATAACCTGTATACAGCTGGAGATTATCATCTAATCATCAATCCTT
Differences
VACV-MVA-146R              --TGATGTTTTTAACGCTACAATCATAGAAGCGTATAACCTGTATACAGCTGGAGATTATCATCTAATCATCAATCCTT
Differences
VACV-WR-158                --TGATGTTTTTAACGCTACAATCATAGAAGCGTATAACCTGTATACAGCTGGAGATTATCATCTAATCATCAATCCTT
Differences
YLDV-124R                  --TTACATATTAGAATCAAAAATATTAGAAGTTCATAACTTATATAATAAAGGAGATTATCACTTTATAATTAATCCTT
Differences
YMTV-124R                  --TTGTATATTGGAATCACGAGTATTAGAGGTTTATAATTTATATAATAAGGGTGACTATTATCTTATAATCAATCCTT
Scale                             |480          |500          |520          |540

Scale                             |560          |580          |600          |620
BPSV-AR02-110              GCGCGCGCTTCATGACGTCGCTCATGGCAAAGGAGTCCGTCTGCCTGTT---CGGATCCGGGTGGTGCGTCGTCGACCT
Differences
CMLV-M96-154               CAGATAATCTGAAAATGAAATTGTCGTTTAACTCTTCATTCTGCATATCAGACGGCAATGGATGGATCATAATTGA--T
Differences
CPXV-BR-171                CAGATGATCTGAAAATGAAATTGTCGTTTAATTCTTCATTCTGTATATCAGACGGCAATGGATGGATCATAATTGA--T
Differences
DPV-W83-134                CAAAAAATTTTCTAAAATATATAAGTGATAGATTTTATTTATGTTTAATAGACAAAAATGGTTGGGCTATTGCCGA--T
Differences
ECTV-Mos-137               CAGATGATCTGAAAATGAAATTGTTGTTTAATTCTTCATTCTGCATATCAGACGGCAATGGATGGCTCATAATTGA--T
Differences
GTPV-Pellor-119            CGGATATTTTTTTAAAAATGATAGCTAATCAATCAAAAAATGTGCTTAACTGATAAAAGTGGGTGGTGTATTGTGGA--T
Differences
LSDV-Nee-124               CGGATAATTTTTTAGAAAATGATAGCTAATCAATCAAAAAATGTGCTTAACTGATAAAAGTGGGTGGTGTATTGTGGA--T
Differences
MOCV-1-145R                CCGTGCGACTCCTGCGCCAGCTGCAGTCTTGTGCTACGTACTGCTTGGACGACGGGCACGGCTGGCTAGCGGTCGACGC
Differences
MPXV-Congo 2003 358-155    CAGATAATCTGAAAATGAAATTGTCGTTTAATTCTTCATTTTGTATATCAGACGGCAATGGATGGATTATAATTGA--T
Differences
MPXV-COP-141               CAGATAATCTGAAAATGAAATTGTCGTTTAATTCTTCATTTTGTATATCAGAVGGCAATGGATGGATTATAATTGA--T Differences
MPXV-Zre-A37R              CAGATAATCTGAAAATGAAATTGTCGTTTAATTCTTCATTTTGTATATCAGACGGCAATGGATGGATTATAATTGA--T
Differences
MYXV-Lau-m123R             GCGACGCGTTTCTAAACGGGTTGGTAAAGAAATACAACGTCTGTCTGTCGTCCAACACAGGATGGGTGATCGCCGA--T
Differences
ORFV-NZ2 Patent-113        GCGCGCAGTTCATGCTGCGGCTGATGGAGAAGGAGAACGTCTGTCTGTT---CGGCAGCGGGTGGTGCATAGTGGACCT
Differences
RPXV-Utr-143               CAGATAATCTGAAAATGAAATTGTCGTTTAATTCTTCATTCTGCATATCAGACGGCAATGGATGGATCATAATTGA--T
Differences
SFV-Kas-s123R              GTGATGTGTTCTTAAATGTTTTGGTAAAGAAATACAATGTCTGTTTGACGTCCAACACAGGATGGGTGATCGCCGA--T
Differences
SPPV-TU-119                CAGATAATTTTTTAAAAATGATTTCTAATCAATCAAAAAATGTGCTTAACTGATAAAAGTGGGTGGTGTATTGTGGA--T
Differences
SWPV-Neb-121               CTGAAACATTTATAAAACATTATTAAAGAAAAATCAAATATATGTTTAACGGATAAACATGGCTGGATTATAATCGA--T
Differences
VACV-Acambis-148           CAGATAATCTGAAAATGAAATTGTCGTTTAATTCTTCATTCTGCATATCAGACGGCAATGGATGGATCATAATTGA--T
Differences
VACV-Cop-A35R              CAGATAATCTGAAAATGAAATTGTCGTTTAATTCTTCATTCTGCATATCAGACGGCAATGGATGGATTATAATTGA--T
Differences
VACV-LC16m8-m8202R         CAGATAATCTGAAAATGAAATTGTCGTTTAATTCTTCATTCTGCATATCAGACGGCAATGGATGGATCATAATTGA--T
Differences
VACV-MVA-146R              CAGATAATCTGAAAATGAAATTGTCGTTTAATTCTTCATTCTGCATATCAGACGGCAATGGATGGATCATAATTGA--T
Differences
VACV-WR-158                CAGATAATCTGAAAATGAAATTGTTGTTTAATTCTTCATTCTGCATATCAGACGGCAATGGATGGATCATAATTGA--T
Differences
YLDV-124R                  CGACCGATTTTTTAATGTTTTAGGAAAATGGTTAACTTTTGTTTAATGACAAAAATGGGTGGATTATAATCGA--T
Differences
YMTV-124R                  CAATTGATTTTTTAACATTTTTGGTAAAAACCGTTAGCTTCTGTTTAACTGACAGGAACGGATGGGTTATAATCGA--C
Scale                             |560          |580          |600          |620
```

TABLE 2-continued

```
Scale                            |640        |660        |680        |700
BPSV-AR02-110                    CCGGAGG----------------------------ATATC-----------------
Differences
CMLV-M96-154                     GGGAAAT----------------------------GCAAT-----------------
Differences
CPXV-BR-171                      GGGAAAT----------------------------GCAAT-----------------
Differences
DPV-W83-134                      G-GAAAA----------------------------GTGA------------------
Differences
ECTV-Mos-137                     GGGAAAT----------------------------GCAAT-----------------
Differences
GTPV-Pellor-119                  ATAAAAA----------------------------ATGA------------------
Differences
LSDV-Nee-124                     ATAAAAA----------------------------ATGA------------------
Differences
MOCV-1-145R                      GTGCGAGTGCCCGCTCTCGCGCTTCCGCTTCGCGCTGCCTTCGTCGCCGCGCGCGAACGCGCCGCCAGCCACGCCGCCG
Differences
MPXV-Congo 2003 358-155          GGGAAAT----------------------------GTAAT-----------------
Differences
MPXV-COP-141                     GGGAAAT----------------------------GTAAT-----------------
Differences
MPXV-Zre-A37R                    GGGAAAT----------------------------GTAAT-----------------
Differences
MYXV-Lau-m123R                   GGGAAAA----------------------------GTGA------------------
Differences
ORFV-NZ2 Patent-113              GCGCAAG----------------------------CTGGA-----------------
Differences
RPXV-Utr-143                     GGGAAAT----------------------------GCAAT-----------------
Differences
SFV-Kas-s123R                    GGAAAAA----------------------------GTGA------------------
Differences
SPPV-TU-119                      ATAAAAA----------------------------ATGA------------------
Differences
SWPV-Neb-121                     GGCAAAA----------------------------ATGA------------------
Differences
VACV-Acambis-148                 GGGAAAT----------------------------GCAAT-----------------
Differences
VACV-Cop-A35R                    GGGAAAT----------------------------GCAAT-----------------
Differences
VACV-LC16m8-m8202R               GGGAAAT----------------------------GCAAT-----------------
Differences
VACV-MVA-146R                    GGGAAAT----------------------------GCAAT-----------------
Differences
VACV-WR-158                      GGGAAAT----------------------------GCAAT-----------------
Differences
YLDV-124R                        GTAAAA-----------------------------GTGA------------------
Differences
YMTV-124R                        GCAAAA-----------------------------GTGA------------------
Scale                            |640        |660        |680        |700

Scale                            |720        |740        |760        |780
BPSV-AR02-110                    ----CTTTACCCCGTGA--------------------
Differences
CMLV-M96-154                     ----AGTAATTTTTTATCATAA---------------
Differences
CPXV-BR-171                      ----AGTAATTTTTTATCATAA---------------
Differences
DPV-W83-134                      ----AATTAAATATTAATTAA----------------
Differences
ECTV-Mos-137                     ----AGTAATTTTTTATCATAA---------------
Differences
GTPV-Pellor-119                  ----AATAGAATATTAA--------------------
Differences
LSDV-Nee-124                     ----AATAGAATATTAA--------------------
Differences
MOCV-1-145R                      GCCGCGTGGCCGCTCGAGCGATCACAAACGCCGGCGGAAACGCTGTTGCCGCCCGCGCGCCCGCTCGAGCCGCCGAAAC
Differences
MPXV-Congo 2003 358-155          ----AGTAATTTTTTATCATAA---------------
Differences
MPXV-COP-141                     ----AGTAATTTTTTATCATAA---------------
```

TABLE 2-continued

| | | | | |
|---|---|---|---|---|
| Differences | | | | |
| MPXV-Zre-A37R | ----AGTAATTTTTTATCATAA------------------------------------------- | | | |
| Differences | | | | |
| MYXV-Lau-m123R | ----AATAGAATAG------------------------------------------------- | | | |
| Differences | | | | |
| ORFV-NZ2 Patent-113 | ----CGTACCCATATAA--------------------------------------------- | | | |
| Differences | | | | |
| RPXV-Utr-143 | ----AGTAATTTTTTATCATAA------------------------------------------- | | | |
| Differences | | | | |
| SFV-Kas-s123R | ----AATAGAATAG--------------------------------------------------- | | | |
| Differences | | | | |
| SPPV-TU-119 | ----AATAGAATATTAA--------------------------------------------- | | | |
| Differences | | | | |
| SWPV-Neb-121 | ----AATTAAATATTAA--------------------------------------------- | | | |
| Differences | | | | |
| VACV-Acambis-148 | ----AGTAATTTTTTATCATAA------------------------------------------- | | | |
| Differences | | | | |
| VACV-Cop-A35R | ----AGTAATTTTTTATCATAA------------------------------------------- | | | |
| Differences | | | | |
| VACV-LC16m8-m8202R | ----AGTAATTTTTTATCATAA------------------------------------------- | | | |
| Differences | | | | |
| VACV-MVA-146R | ----AGTAATTTTTTATCATAA------------------------------------------- | | | |
| Differences | | | | |
| VACV-WR-158 | ----AGTAATTTTTTATCATAA------------------------------------------- | | | |
| Differences | | | | |
| YLDV-124R | ----AATAA----------------------------------------------------- | | | |
| Differences | | | | |
| YMTV-124R | ----AATAATACATTAG--------------------------------------------- | | | |
| Scale | \|720 | \|740 | \|760 | \|780 |
| Scale | \|800 | | | |
| BPSV-AR02-110 | -------- | | | |
| Differences | | | | |
| CMLV-M96-154 | -------- | | | |
| Differences | | | | |
| CPXV-BR-171 | -------- | | | |
| Differences | | | | |
| DPV-W83-134 | -------- | | | |
| Differences | | | | |
| ECTV-Mos-137 | -------- | | | |
| Differences | | | | |
| GTPV-Pellor-119 | -------- | | | |
| Differences | | | | |
| LSDV-Nee-124 | -------- | | | |
| Differences | | | | |
| MOCV-1-145R | TGAAATAA | | | |
| Differences | | | | |
| MPXV-Congo 2003 358-155 | -------- | | | |
| Differences | | | | |
| MPXV-COP-141 | -------- | | | |
| Differences | | | | |
| MPXV-Zre-A37R | -------- | | | |
| Differences | | | | |
| MYXV-Lau-m123R | -------- | | | |
| Differences | | | | |
| ORFV-NZ2 Patent-113 | -------- | | | |
| Differences | | | | |
| RPXV-Utr-143 | -------- | | | |
| Differences | | | | |
| SFV-Kas-s123R | -------- | | | |
| Differences | | | | |
| SPPV-TU-119 | -------- | | | |
| Differences | | | | |
| SWPV-Neb-121 | -------- | | | |
| Differences | | | | |
| VACV-Acambis-148 | -------- | | | |
| Differences | | | | |
| VACV-Cop-A35R | -------- | | | |
| Differences | | | | |
| VACV-LC16m8-m8202R | -------- | | | |
| Differences | | | | |
| VACV-MVA-146R | -------- | | | |
| Differences | | | | |
| VACV-WR-158 | -------- | | | |
| Differences | | | | |
| YLDV-124R | -------- | | | |
| Differences | | | | |
| YMTV-124R | -------- | | | |
| Scale | \|800 | | | |

In Table 2:
BPSV, Bovine popular stomatitis virus (SEQ ID NO: 8)
CMLV, Camelpox virus (SEQ ID NO: 9)
CPXV, Cowpox virus (SEQ ID NO: 10)
DPV, Deerpox virus (SEQ ID NO: 11)

TABLE 2-continued

ECTV, Ectromelia virus (SEQ ID NO: 12)

GTPV, Goatpox virus Pellor (SEQ ID NO: 13)

LSDV, Lumpy skin disease virus (SEQ ID NO: 14)

MOCV, Molluscum contagiosum virus (SEQ ID NO: 15)

MPXV, Monkeypox virus (SEQ ID NOs: 16, 17 and 18)

MYXV, Myxoma virus (SEQ ID NO: 19)

ORFV, Orf virus (SEQ ID NO: 20)

RPXV, Rabbitpox virus (SEQ ID NO: 21)

SFV, Rabbit fibroma virus (SEQ ID NO: 22)

SPPV, Sheeppox virus (SEQ ID NO: 23)

SWPV, Swinepox virus (SEQ ID NO: 24)

VACV, Vaccinia virus (SEQ ID NOS: 25, 26, 27, 28 and 29)

YLDV, Yaba-like disease virus (SEQ ID NO: 30)

YMTV, Yaba-like monkey tumor virus (SEQ ID NO: 31)

TABLE 3

```
Scale            |1          |20         |40         |60         |80
BPSV-AR02-110    --------MTNGNMSCLQILTPFGLIFAPDDVRLREIALELGITY-VSRAFGDMLYGEMSFTSLPMNEVP-ACVSDCYLAVNGNLIPC
Differences
DPV-W83-134      -----------MEEDFTTLLTVLGTMRIENKN-LIKTYDDLGINI---VDDFGPYKLASLEISLVSSELLKTYDLQDCYIAHNGIVLHC
Differences
LSDV-Nee-124     --MDFDFIFDKDEDDIYTLITTLGVLKIKKK-EISKVCSELGINL--IETLGPYNVVSLNIHPFPNNFIEQSNLINCYISYNGTLFHC
Differences
MOCV-1-145R      -----------MGPGGFPVITPLGRMHLRADMRTRVMCVDFGVTMDTLRVLGPYVVMVPMLEPASASLLAPRALRDCYVAAHGVLLHC
Differences
MYXV-Lau-m123R   ------------MDADRITCVTALGVLYIRHD-EIDTVRSELGITF--IGDVGPYRVATLNICPVALDDVYQRGVTNCYIVSDGRITRC
Differences
ORFV-NZ2-113     -------------MSRLQILTSFGQIFAPDEARLREIARDLGICT-IKRAFGDMLYGFIDFDPVPLTQVNML-MSNCYFAVNGNLLPC
Differences
SPPV-TU-119      --MDFDFIFNKDEDDIYTLITTLGVLKIKKK-EISKVCSELDINF--IETLGPYNVVSLNIHPFPNNFIEQSNLINCYISYNGRLFHC
Differences
SWPV-Neb-121     -------MYQWIVDMATYTFVTSLGVLKLSED-NVSRSFSDLGITI---IDRIGPYHIASIELHSIPMEYITQKDLEKCYIVHNGLILQC
Differences
VACV-Cop-A35R    -------------MDAAFVITPMGVLTIT-----DTLYDDLDISI---MDFIGPYIIGNIKTVQIDVRDIKYSDMQKCYFSYKGKIVPQ
Differences
VARV-Ind-A38R    -------------MDTTFVITPMGMLTIT-----DTLYDDLDISI---MDFIGPYIIGNIKTVQIDVRDIKYSDMQKCYFS--------
Differences
YLDV-124R        ----------MEIAGYNFIITSFGVIKIHSVNHFKTVCEDLGIVI---VDYIGEYAIATLEVQEINVNLINQNDIYDCYVACNGFIVNC
Differences
YMTV-124R        MKSYSVFIHNTIENMYNVVITSFGVINIYGFEHLKTVCEDLGIVV--FDFVGEYAIATLNAQEISVNLITQDDINDCYIACNGFIVKC
Scale            |1          |20         |40         |60         |80

Scale                       |100         |120        |140        |160
BPSV-AR02-110    TESFRLRIPMDGVKAAYRTGTGKTILCGPE---FNVVNPSGFRPALRL--RELSHVAAHTEILELYS--ESGNYEFIMGPSARFMTSLM
Differences
DPV-W83-134      SSDNKLNIPVYKVYSVYMSKKSIIICFDE---CPKLFIDGKSQPFYIL--SSSLM--MDAHIIEVYNLYDEGDYHIILNPSKNFLKYIS
Differences
LSDV-Nee-124     SKDERLSIPINGLYRGFYSNNSFIFSFDKENYGKLLIDEKEQYFYLG--TAYDI--VNSNIIEVYNLYRKGDYNFIINPSDNFLEMIA
Differences
MOCV-1-145R      SELAYLCAPMTRIFAVFPRARRRYVLCCDD--YDVLRTHVGGSAFSVRRFTDADF--ERVRVLELYNYNYCGEYQLVLLPSVRLLRQLQ
Differences
MYXV-Lau-m123R   SNQYRLTFPIHKVYTVYKSINSFMLCFDK--CFKLRIDNNPQDFFIT--SSIAI--QDARVLEVYNLYKKGDYHLILNPSDAFLNGLV
Differences
ORFV-NZ2-113     TEDFRLRLPATEISAAYLTRTGRTILCGKD--FNIVAPSGFKPSMRL--RDLSHVSALVEILEVYD--ESGEYQFVLGPSAQFMLRLM
Differences
SPPV-TU-119      SKDERLSIPINGLYRGFYSNNSFIFSFDKENYGKLLIDEKKQYFYLG--TAYDI--VNSNIIEVYNLYRKGDYNFIINPSDNFLKMIS
Differences
SWPV-Neb-121     SKDNNLNMHVHNVHRAYHSVNSCILCFDR--YPRLSLEGKYQPFYIS--TSTCI--TANSIMEVYNKNKKDDYEFIINPSETFIKHIK
Differences
VACV-Cop-A35R    DSNDLARFNIYSICAAYRSKNTIIIACDY--DIMLDIEDKHQPFYLF--PSIDV--FNATIIEAYNLYTAGDYHLIINPSDNLKMKLS
Differences
VARV-Ind-A38R    ----------------------------------------------------------------------------------------
Differences
YLDV-124R        SKLNNVPFPVTQVYYAFLTKNKILLCCDK--YPKLSINNKIQPFYIS--SSIYI--LESKILEVHNLYNKGDYHFIINPSTDFLMFLG
Differences
YMTV-124R        SEYNKVPFPVIQIYCAFLTKSKILLCCDY--HPKLFVDNMLQPFYIS--FSICI--LESRVLEVYNLYNKGDYYLIINPSIDFLTFLV
Scale                       |100         |120        |140        |160
```

TABLE 3-continued

```
Scale              |180              |200              |220              |240              |260
BPSV-AR02-110      AKESVCLFG-SGWCVVDL-------------------------------------RRISFTP---
Differences        ■■ ■■■  ■  ■                                           ■■■■■■
DPV-W83-134        DRFYLCLIDKNGWAIADG-------------------------------------KVKLNIN---
Differences        ■   ■ ■ ■■■                                            ■
LSDV-Nee-124       NQSKMCLTDKSGWCIVDI-------------------------------------KNEIEY----
Differences                                                               ■
MOCV-1-145R        SCATYCLDDGHGWLAVDACECPLSRFRFALPSSPRANAPPATPPAAWPLERSQTPAETLLPPARPLEPPKLK
Differences        ■■  ■    ■ ■ ■
MYXV-Lau-m123R     KKYNVCLSSNTGWVIADG-------------------------------------KSEIE-----
Differences        ■■   ■    ■
ORFV-NZ2-113       EKENVCLFG-SGWCIVDL-------------------------------------RKLDVPI---
Differences        ■   ■   ■  ■                                           ■
SPPV-TU-119        NQSKMCLTDKSGWCIVDI-------------------------------------KN I Y----
Differences        ■■ ■■                                                  ■
SWPV-Neb-121       EKSNICLTDKHGWIIIDG-------------------------------------KNEIKY----
Differences        ■■ ■■ ■  ■                                             ■■
VACV-Cop-A35R      FNSSFCISDGNGWIIIDG-------------------------------------KCNSNPLS--
Differences
VARV-Ind-A38R      ------------------
Differences
YLDV-124R          KMVNFCLTDKNGWIIVDV-------------------------------------KVK-------
Differences        ■■ ■ ■  ■■■                                            ■
YMTV-124R          KTCSFCLTDRNGWVIIDA-------------------------------------KSEIIH----
Scale              |180              |200              |220              |240              |260
```

In Table 3:
BPSV, Bovine popular stomatitis virus (SEQ ID NO: 32)
DPV, Deerpox virus (SEQ ID NO: 33)
LSDV, Lumpy skin disease virus (SEQ ID NO: 34)
MOCV, Molluscum contagiosum virus (SEQ ID NO: 35)
MYXV, Myxoma virus (SEQ ID NO: 36)
ORFV, Orf virus (SEQ ID NO: 37)
SPPV Sheeppox virus (SEQ ID NO: 38)
SWPV, Swinepox virus (SEQ ID NO: 39)
VACV, Vaccinia virus (SEQ ID NO: 40)
VARY, Variola virus (SEQ ID NO: 41)
YLDV, Yaba-like disease virus (SEQ ID NO: 42)
YMTV, Yaba-like monkey tumor virus (SEQ ID NO: 43)

What is claimed is:

1. A method of treating cancer in a subject, comprising administering to the subject an effective amount of a poxvirus engineered to delete or disrupt nucleic acid encoding an A35R protein.

2. The method of claim 1, wherein the poxvirus further comprises nucleic acid selected from the group consisting of:

a) nucleic acid encoding a costimulatory molecule;
b) nucleic acid encoding a tumor antigen; and
c) nucleic acid encoding an immunomodulatory protein.

3. The method of claim 2, wherein the costimulatory molecule is B7.1, ICAM-1, or LFA-3.

* * * * *

UNITED STATES PATENT AND TRADEMARK OFFICE
CERTIFICATE OF CORRECTION

PATENT NO. : 9,028,837 B2  Page 1 of 1
APPLICATION NO. : 13/722590
DATED : May 12, 2015
INVENTOR(S) : Roper It is certified that error appears in the above-identified patent and that said Letters Patent is hereby corrected as shown below:

Specification

Column 5, Line 21: Please correct "(LL-2)" to read -- (IL-2) --
Column 8, Line 20: Please correct "I MEC-expressing"
        to read -- I MHC-expressing --
Column 34, Line 33: Please correct "vA35A" to read -- vA35Δ --
Column 34, Line 48: Please correct "An A35A/wild-type"
        to read -- An A35Δ/wild-type --
Column 34, Line 53: Please begin a new paragraph at "Attenuation in mice." So that it reads as follows:
    the control.
    · Attenuation in mice.
Column 34, Line 58: Please correct "(the vA350 mutant virus),"
        to read -- (the vA35Δ mutant virus), --
Column 35, Line 3: Please correct "A35A" to read -- A35Δ --
Column 35, Line 13: Please correct "A35A" to read -- A35Δ --
Column 35, Line 29: Please correct "vA35A," to read -- vA35Δ, --
Column 36, Line 12: Please correct "vA35A" to read -- vA35Δ --
Column 36, Line 14: Please correct "vA35A" to read -- vA35Δ --
Column 36, Line 19: Please correct "vA35A," to read -- vA35Δ, --

Signed and Sealed this
Fifteenth Day of March, 2016

Michelle K. Lee
*Director of the United States Patent and Trademark Office*

SEQUENCE LISTING

<160> NUMBER OF SEQ ID NOS: 44

<210> SEQ ID NO 1
<211> LENGTH: 528
<212> TYPE: DNA
<213> ORGANISM: Vaccinia virus

<400> SEQUENCE: 1
atggacgccg cgtttgttat tactccaatg ggtgtgttga ctataacaga tacattgtat 60
gatgatctcg atatttcaat catggacttt ataggaccat acattatagg taacataaaa 120
actgtccaaa tagatgtacg ggatataaaa tattccgaca tgcaaaaatg ctactttagc 180
tataagggta aaatagttcc tcaggattct aatgatttgg ctagattcaa catttatagc 240
atttgtgccg catacagatc aaaaaatacc atcatcatag catgcgacta tgatatcatg 300
ttagatatag aagataaaca tcagccattt tatctattcc catctattga tgtttttaac 360
gctacaatca tagaagcgta taacctgtat acagctggag attatcatct aatcatcaat 420
ccttcagata atctgaaaat gaaattgtcg tttaattctt cattctgcat atcagacggc 480
aatggatgga ttataattga tgggaaatgc aatagtaatt ttttatca 528

<210> SEQ ID NO 2
<211> LENGTH: 176
<212> TYPE: PRT
<213> ORGANISM: Vaccinia virus

<400> SEQUENCE: 2

Met Asp Ala Ala Phe Val Ile Thr Pro Met Gly Val Leu Thr Ile Thr

```
                1               5                   10                  15
Asp Thr Leu Tyr Asp Asp Leu Asp Ile Ser Ile Met Asp Phe Ile Gly
                20                  25                  30

Pro Tyr Ile Ile Gly Asn Ile Lys Thr Val Gln Ile Asp Val Arg Asp
                35                  40                  45

Ile Lys Tyr Ser Asp Met Gln Lys Cys Tyr Phe Ser Tyr Lys Gly Lys
 50                  55                  60

Ile Val Pro Gln Asp Ser Asn Asp Leu Ala Arg Phe Asn Ile Tyr Ser
 65                  70                  75                  80

Ile Cys Ala Ala Tyr Arg Ser Lys Asn Thr Ile Ile Ala Cys Asp
                85                  90                  95

Tyr Asp Ile Met Leu Asp Ile Glu Asp Lys His Gln Pro Phe Tyr Leu
                100                 105                 110

Phe Pro Ser Ile Asp Val Phe Asn Ala Thr Ile Ile Glu Ala Tyr Asn
                115                 120                 125

Leu Tyr Thr Ala Gly Asp Tyr His Leu Ile Ile Asn Pro Ser Asp Asn
                130                 135                 140

Leu Lys Met Lys Leu Ser Phe Asn Ser Ser Phe Cys Ile Ser Asp Gly
145                 150                 155                 160

Asn Gly Trp Ile Ile Ile Asp Gly Lys Cys Asn Ser Asn Phe Leu Ser
                165                 170                 175

<210> SEQ ID NO 3
<211> LENGTH: 60
<212> TYPE: PRT
<213> ORGANISM: Variola virus

<400> SEQUENCE: 3

Met Asp Thr Thr Phe Val Ile Thr Pro Met Gly Met Leu Thr Ile Thr
1               5                   10                  15

Asp Thr Leu Tyr Asp Asp Leu Asp Ile Ser Ile Met Asp Phe Ile Gly
                20                  25                  30

Pro Tyr Ile Ile Gly Asn Ile Lys Thr Val Gln Ile Asp Val Arg Asp
                35                  40                  45

Ile Lys Tyr Ser Asp Met Gln Lys Cys Tyr Phe Ser
 50                  55                  60

<210> SEQ ID NO 4
<211> LENGTH: 60
<212> TYPE: PRT
<213> ORGANISM: Variola virus

<400> SEQUENCE: 4

Met Asp Thr Thr Phe Val Ile Thr Pro Met Gly Met Leu Thr Ile Thr
1               5                   10                  15

Asp Thr Leu Tyr Asp Asp Leu Asp Ile Ser Ile Met Asp Phe Ile Gly
                20                  25                  30

Pro Tyr Ile Ile Gly Asn Ile Lys Thr Val Gln Ile Asp Val Arg Asp
                35                  40                  45

Ile Lys Tyr Ser Asp Met Gln Lys Cys Tyr Phe Ser
 50                  55                  60

<210> SEQ ID NO 5
<211> LENGTH: 22
<212> TYPE: DNA
<213> ORGANISM: Artificial
<220> FEATURE:
<223> OTHER INFORMATION: Example PCR primer sequence
```

-continued

```
<400> SEQUENCE: 5
atggacgccg cgtttgttat ta 22

<210> SEQ ID NO 6
<211> LENGTH: 18
<212> TYPE: DNA
<213> ORGANISM: Artificial
<220> FEATURE:
<223> OTHER INFORMATION: Example PCR primer sequence
<400> SEQUENCE: 6
tgataaaaaa ttactatt 18

<210> SEQ ID NO 7
<211> LENGTH: 20
<212> TYPE: DNA
<213> ORGANISM: Artificial
<220> FEATURE:
<223> OTHER INFORMATION: Example A35R probe sequence
<400> SEQUENCE: 7
tgataaaaaa ttactattgc 20

<210> SEQ ID NO 8
<211> LENGTH: 555
<212> TYPE: DNA
<213> ORGANISM: Bovine papular stomatitis virus
<400> SEQUENCE: 8
atgacaaacg gcaacatgtc gtgccttcaa atactcactc catttggact aatcttcgca 60
cccgacgatg ttcggctgcg tgagatcgcg ctggaactgg ggatcaccta cgtttcccgc 120
gcattcggag acatgttgta cggcgagatg tcgttcacct ccttacccat gaacgaggtg 180
cccgcgtgcg tgtcggactg ctaccttgcc gtgaacggga acctcatacc gtgcacggag 240
tccttcaggc ttcggatacc catggacggc gttaaggcgg cctaccgcac aggcaccggc 300
aagacgatcc tctgcggccc cgaattcaac gtcgtgaacc cctccggctt tcgtccggcc 360
ctgcggctcc gcgagctcag ccacgtggcg gcgcatacag agatcttaga gctgtactcg 420
gagtccggca actacgagtt catcatgggg ccaagcgcgc gcttcatgac gtcgctcatg 480
gcaaaggagt ccgtctgcct gttcggatcc gggtggtgcg tcgtcgacct ccggaggata 540
tcctttaccc cgtga 555

<210> SEQ ID NO 9
<211> LENGTH: 531
<212> TYPE: DNA
<213> ORGANISM: Camelpox virus
<400> SEQUENCE: 9
atggacgccg cgtttgttat tactccaatg ggtgtgttga ctataacaga tacattatat 60
tatgatcttg atatctcaat aatggacttt ataggaccat acattatagg taacataaaa 120
actgtccaaa tagatgtacg ggatataaaa tattccgaca tgcaaaaatg ctactttagc 180
tataagggta aaatagttcc tcaagattct aatgatttgg ctagattcaa catttatagc 240
atttgtgccg catacagatc aaaaaataca atcatcatag catgtgacta tgatatcatg 300
ttagatatag aatgtaaaca tcagccattt tatctattcc catctattga tgtttttaac 360
gctacaataa tagaagcgta taacctgtat acagctggag attatcatct gatcatcaat 420
```

-continued

```
ccttcagata atctgaaaat gaaattgtcg tttaactctt cattctgcat atcagacggc    480
aatggatgga tcataattga tgggaaatgc aatagtaatt ttttatcata a             531
```

```

<210> SEQ ID NO 10
<211> LENGTH: 531
<212> TYPE: DNA
<213> ORGANISM: Cowpox virus

<400> SEQUENCE: 10
atggacgccg cgtttgttat tactccaatg ggtgtgttga ctataacaga tacattgtat     60
gatgatcttg atatctcaat catggacttt ataggaccat acatcatagg taacataaaa    120
actgtccaaa tagatgtacg ggatataaaa tattccgata tgcaaaaatg ctactttagc    180
tataagggta aaatagttcc tcaggattct aatgatttgg ctagattcaa catttatagc    240
atttgtgctg catacagatc aaaaaatacc atcatcatag catgcgacta tgatatcatg    300
ttagatatag aaggtaaaca tcagccattt tatctattcc catctattga tgtttttaac    360
gctacaatca tagaagcgta taacctgtac acagctggag attatcatct gatcatcaat    420
ccttcagatg atctgaaaat gaaattgtcg tttaattctt cattctgtat atcagacggc    480
aatggatgga tcataattga tgggaaatgc aatagtaatt ttttatcata a             531
```

```
<210> SEQ ID NO 11
<211> LENGTH: 546
<212> TYPE: DNA
<213> ORGANISM: Deerpox virus
<400> SEQUENCE: 11
atggaggaag attttacaac attgttaact gttttaggaa ctatgagaat tgaaaataag     60
aatctcataa aaacctatga tgatttgggt ataaacattg ttgatgattt tggaccctat    120
aaactcgcat ctttggaaat ttctttagtt tcttcagaat tgttaaaaac ctatgattta    180
caggattgtt atatagccca taatggaatt gtgttacatt gttcttctga taataaatta    240
aatataccgg tatataaagt gtattctgta tatatgtcta agaaaagcat aattatttgt    300
tttgatgaat gtccaaaatt gtttatagat ggaaaatctc aacctttcta tattttatct    360
tcttcattaa tgatggatgc gcatattatt gaagtgtata atttatatga tgagggtgat    420
tatcatatta ttttaaaccc ttcaaaaaat tttctaaaat atataagtga tagattttat    480
ttatgtttaa tagacaaaaa tggttgggct attgccgatg gaaaagtgaa attaaatatt    540
aattaa                                                               546
```

```
<210> SEQ ID NO 12
<211> LENGTH: 531
<212> TYPE: DNA
<213> ORGANISM: Ectromelia virus
<400> SEQUENCE: 12
atggacgccg cgtttgttat tactccaatg ggtgtgttga ctataacaga tacattatat     60
gaggatctcg atatctcaat aatagacttt ataggaccat atattatagg taacataaaa    120
actgtccaaa tagatgtatg ggatataaaa tattccgaca tgcaaaaatg ctactttagc    180
tataagggta aaatagttcc tcaggattct aatgatttgg ctagattcaa catttatagc    240
atttgtgcag catacagatc aaaaaatacc atcatcatag catgcgacta tgatatcatg    300
ttagatatag aaggtaaaca tcagccattt tatctattcc catctattga tgtttttaac    360
gctacaatca tagaagcgta taatctgtat acagctggag attatcatct gatcatcaat    420
```

```
ccttcagatg atctgaaaat gaaattgttg tttaattctt cattctgcat atcagacggc    480
aatggatggc tcataattga tgggaaatgc aatagtaatt ttttatcata a             531

<210> SEQ ID NO 13
<211> LENGTH: 576
<212> TYPE: DNA
<213> ORGANISM: Goatpox virus Pellor

<400> SEQUENCE: 13
atggatttta actttatttt caacaaagac gaagatgata tttatacgtt aataacaact     60
ttaggtgtat taaaaataaa aagaaagaa atatcaaaag tttgtagtga tctagacatt    120
aatcttatag aaacattagg accttataac gtagtatctt aaatatata cccatttcct    180 aacaatttca tagaacaatc aaatttgatt aactgctata tatcttataa tgggacactg    240
tttcactgtt ctaaagatga aagactgagt atcccaataa atggcttgta tagagggttt    300
tactctaaca atagttttat attttctttt gataaagaaa attatggtaa gttactaatt    360
gatgaaaaag aacaatattt ttacctaggg acagcatatg atatagttaa ttcaaatatc    420
attgaagtgt ataatttata caggaaagga gattacaatt ttattataaa tccatcggat    480
atttttttaa aaatgatagc taatcaatca aaaatgtgct taactgataa aagtgggtgg    540
tgtattgtgg atataaaaaa tgaaatagaa tattaa                             576

<210> SEQ ID NO 14
<211> LENGTH: 576
<212> TYPE: DNA
<213> ORGANISM: lumpy skin disease virus

<400> SEQUENCE: 14
atggattttg acttcatttt cgacaaagac gaggatgata tttatacgtt aataacaact     60
ttaggtgtat taaaaataaa aagaaagaa atatcaaaag tttgtagtga gctaggaatt    120
aatcttatag aaacattagg accttataac gtagtatctt aaatataca cccatttcct    180 aacaatttca tagaacaatc aaatttgatt aattgttata tatcttataa tgggacactg    240
tttcactgtt ctaaagatga aagactgagt atcccaataa atggcttgta tagagggttt    300
tactctaaca atagttttat attttctttt gataaagaaa attatggtaa gctactaatt    360
gatgaaaaag aacaatattt ttacctaggg acagcatatg atatagttaa ttcaaatatc    420
atcgaagtgt ataatttata caggaaagga gattacaatt ttattataaa tccatcggat    480 aatttttag aaatgatagc taatcaatca aaaatgtgct taactgataa aagtgggtgg    540
tgtattgtgg atataaaaaa tgaaatagaa tattaa                             576

<210> SEQ ID NO 15
<211> LENGTH: 702
<212> TYPE: DNA
<213> ORGANISM: Molluscum contagiosum virus

<400> SEQUENCE: 15
atgggccctg gcggctttcc tgtcatcacc ccgctgggcc gcatgcacct acgcgccgac     60
atgcgcacgc gcgtcatgtg cgtggacttt ggcgtgacca tggacacgct gcgcgtgctg    120
ggcccctacg tggtcatggt gcccatgctc gagcctgcca gcgccagcct gctggcaccg    180
cgcgcgctcc gagactgcta cgtcgcggcg cacggtgtgc tactgcactg cagcgagctc    240
gcgtacctgt gcgcgcccat gacacgcatc ttcgccgtct ttcgcgcgcg ccgccgctac    300
```

```
gtgctctgct gcgacgacta cgacgtgctg cgcacgcacg tgggcggctc tgccttcagc    360
gtgcgcaggt tcacagacgc ggacttcgag cgcgtgcgcg tgctcgagct ctacaactac    420
aactactgcg gcgagtacca gttggtgctg ctgccctccg tgcgactcct gcgccagctg    480
cagtcttgtg ctacgtactg cttggacgac gggcacggct ggctagcggt cgacgcgtgc    540
gagtgcccgc tctcgcgctt ccgcttcgcg ctgccttcgt cgccgcgcgc gaacgcgccg    600
ccagccacgc cgccggccgc gtggccgctc gagcgatcac aaacgccggc ggaaacgctg    660
ttgccgcccg cgcgcccgct cgagccgccg aaactgaaat aa                       702

<210> SEQ ID NO 16
<211> LENGTH: 531
<212> TYPE: DNA
<213> ORGANISM: Monkeypox virus

<400> SEQUENCE: 16
atggacgccg cgtttgttat tactccaatg ggtgtgttga ctataacaga tacattgtat     60
gatgatctcg atatctcaat catggacttt ataggaccat acattatagg taacataaaa    120
attgtccaaa tagatgcacg ggatataaaa tattccgaca tgcaaaaatg ctactttagc    180 tataaggggta aaatagttcc tcaggattct aatgatttgg ctagattcaa catttatagt    240
atttgtaccg catacagatc aaaaaatacc atcatcatag catgcgacta tgatatcatg    300
ttagatatag aaggtaaaca tcaaccattt tatctattcc catctattga tgttttttaac   360 gctacaatca tagaagcgta taatctgtat acagctggag attatcatct gatcatcaat    420
ccttcagata atctgaaaat gaaattgtcg tttaattctt cattttgtat atcagacggc    480
aatggatgga ttataattga tgggaaatgt aatagtaatt ttttatcata a             531

<210> SEQ ID NO 17
<211> LENGTH: 531
<212> TYPE: DNA
<213> ORGANISM: Monkeypox virus

<400> SEQUENCE: 17
atggacgccg cgtttgttat tactccaatg ggtgtgttga ctataacaga tacattgtat     60
gatgatctcg atatctcaat catggacttt ataggaccat acattatagg taacataaaa    120
attgtccaaa tagatatacg ggatataaaa tattccgaca tgcaaaaatg ctactttagc    180 tataaggggta aaatagttcc tcaggattct aatgatttgg ctagattcaa catttatagt    240
atttgtaccg catacagatc aaaaaatacc atcatcatag catgcgacta tgatatcatg    300
ttagatatag aaggtaaaca tcaaccattt tatctattcc catctattga tgttttttaac   360 gctacaatca tagaagcgta taatctgtat acagctggag attatcatct gatcatcaat    420
ccttcagata atctgaaaat gaaattgtcg tttaattctt cattttgtat atcagacggc    480
aatggatgga ttataattga tgggaaatgt aatagtaatt ttttatcata a             531

<210> SEQ ID NO 18
<211> LENGTH: 531
<212> TYPE: DNA
<213> ORGANISM: Monkeypox virus

<400> SEQUENCE: 18
atggacgccg cgtttgttat tactccaatg ggtgtgttga ctataacaga tacattgtat     60
gatgatctcg atatctcaat catggacttt ataggaccat acattatagg taacataaaa    120
attgtccaaa tagatgcacg ggatataaaa tattccgaca tgcaaaaatg ctactttagc    180
```

```
tataagggta aaatagttcc tcaggattct aatgatttgg ctagattcaa catttatagt    240
atttgtaccg catacagatc aaaaaatacc atcatcatag catgcgacta tgatatcatg    300
ttagatatag aaggtaaaca tcaaccattt tatctattcc catctattga tgttttttaac   360 gctacaatca tagaagcgta taatctgtat acagctggag attatcatct gatcatcaat    420
ccttcagata atctgaaaat gaaattgtcg tttaattctt catttgtat atcagacggc     480 aatggatgga ttataattga tgggaaatgt aatagtaatt ttttatcata a              531
```

```
<210> SEQ ID NO 19
<211> LENGTH: 540
<212> TYPE: DNA
<213> ORGANISM: Myxoma virus

<400> SEQUENCE: 19
atggacgccg atagaattac gtgcgtgacg gccctaggcg tgttatatat acgtcacgac    60
gagatagaca cggtgcgttc tgaactggga ataacgttca taggagacgt gggaccgtat   120
cgtgtagcga cttttaaatat ttgtccggtg gcgttagacg atgtatacca acgaggcgtg   180
actaattgtt acatcgtcag tgacggaagg attacacgct gttctaatca atacaggtta    240
acatttccta tacacaaggt gtatacggtg tataaatcta ttaatagttt tatgttgtgt    300
ttcgataaat gtttcaaatt acgcatagat aacaatcccc aagatttctt catcacatcg    360
tctatagcga ttcaggacgc gcgggtactc gaagtgtaca acctgtataa gaaaggggac    420
tatcatctca ttctcaatcc cagcgacgcg tttctaaacg ggttggtaaa gaaatacaac    480
gtctgtctgt cgtccaacac aggatgggtg atcgccgatg ggaaaagtga aatagaatag   540
```

```
<210> SEQ ID NO 20
<211> LENGTH: 540
<212> TYPE: DNA
<213> ORGANISM: Orf virus

<400> SEQUENCE: 20
atgtcgcgac ttcaaatact gacctcattt ggacaaatct tcgcacccga cgaagctcgg    60
ctgcgcgaga tcgcgcgtga tttgggaata tgcaccataa aacgcgcatt cggcgacatg   120
ctgtacggct ttatagactt cgacccggtg ccctgaccc aagtaaacat gctcatgtcc    180
aactgctact tcgcggtcaa cggcaacctg cttccgtgca cggaggactt ccggctcaga    240
ctcccggcaa cggagatctc tgcggcctac ctgacgagaa cgggacggac gatcctgtgc    300
ggcaaagact tcaacatagt agcgccgtcg gggttcaagc cgtccatgcg gctgcgcgac    360
ctcagtcacg tgtctgcgct tgtagagatc ctggaagtct acgacgagtc cggggagtac    420
caattcgtgc tcgccccag cgcgcagttc atgctgcggc tgatggagaa ggagaacgtc    480
tgtctgttcg gcagcgggtg gtgcatagtg gacctgcgca agctggacgt acccatataa    540
```

```
<210> SEQ ID NO 21
<211> LENGTH: 534
<212> TYPE: DNA
<213> ORGANISM: Rabbitpox virus

<400> SEQUENCE: 21
atggacgccg cgtttgttat tactccaatg ggtgtgttga ctataacaga tacattgtat    60
gatgatctcg atatctcaat catggacttt ataggaccat acattatagg taacataaaa   120
actgtccaaa tagatgtacg ggatataaaa tattccgaca tgcaaaaatg ctactttagc    180
```

| | |
|---|---|
| tataagggta aaatagttcc tcaggattct aatgatttgg ctagattcaa catttatagc | 240 |
| atttgtgccg catacagatc aaaaaatacc atcatcatca tagcatgcga ctatgatatc | 300 |
| atgttagata tagaagataa acatcagcca ttttatctat tcccatctat tgatgttttt | 360 |
| aacgctacaa tcatagaagc gtataacctg tatacagctg gagattatca tctaatcatc | 420 |
| aatccttcag ataatctgaa atgaaattg tcgtttaatt cttcattctg catatcagac | 480 |
| ggcaatggat ggatcataat tgatgggaaa tgcaatagta atttttatc ataa | 534 |

<210> SEQ ID NO 22
<211> LENGTH: 540
<212> TYPE: DNA
<213> ORGANISM: Rabbit fibroma virus

<400> SEQUENCE: 22

| | |
|---|---|
| atggacgccg atagaataac gtgcgtgaca gccctaggcg tgttgtctat acaccacgac | 60 |
| gagatgaaca tggtgtgttc tgaactggga attacattca taggagacat tggaccgtat | 120 |
| cgcgtggcga ctttaaatat ttgtccggtg gcgttcgatg atgtacatca acgtggcgtg | 180 |
| attaactgtt atatcgtcag tgatggaagg attatacgat gttctaacca gtacaggcta | 240 |
| gcatttccca tacacaaggt atatacggtg tataaatcta ttaatagttt tatgttttgt | 300 |
| tttgataaat gtttcaaatt acacatagat accaaccacc aagatttctt cattacgtca | 360 |
| tctatagcga ttcaggatgc acgagtcctt gaagtgtaca acctttacaa gaaaggagac | 420 |
| taccatttca ttctcaatcc cagtgatgtg ttcttaaatg ttttggtaaa gaaatacaat | 480 |
| gtctgtttga cgtccaacac aggatgggtg atcgccgatg gaaaaagtga aatagaatag | 540 |

<210> SEQ ID NO 23
<211> LENGTH: 576
<212> TYPE: DNA
<213> ORGANISM: sheeppox virus

<400> SEQUENCE: 23

| | |
|---|---|
| atggattttg acttcatttt caacaaagac gaggatgata tttatacgtt aataacaact | 60 |
| ttaggtgtat taaaaataaa aaaaaagaa atatcaaaag tttgtagtga actagacatt | 120 |
| aattttatag aaacattagg accttataat gtagtatctt taaatataca cccatttcct | 180 |
| aacaatttta tagaacaatc aaatttgatt aactgttata tatcttataa tgggagactg | 240 |
| tttcactgtt ctaaagatga agactgagt atcccaataa atggattgta tagagggttt | 300 |
| tactctaata tagttttat attttcttt gataaagaaa attatggtaa gttactaatt | 360 |
| gatgaaaaaa aacaatattt ttacctaggc acagcatatg atatagttaa ttcaaatatc | 420 |
| atcgaagtgt ataatttata caggaaagga gattacaatt ttattataag tccatcagat | 480 |
| aatttttaa aaatgatttc taatcaatca aaaatgtgct taactgataa aagtgggtgg | 540 |
| tgtattgtgg atataaaaaa tgaaatagaa tattaa | 576 |

<210> SEQ ID NO 24
<211> LENGTH: 558
<212> TYPE: DNA
<213> ORGANISM: Swinepox virus

<400> SEQUENCE: 24

| | |
|---|---|
| atgtatcaat ggatcgtcga tatggctacc tatacattcg taacatcatt gggtgtattg | 60 |
| aaactatcag aagataatgt atcaagatcg ttctcagatt taggcattac cattattgat | 120 |
| cgtataggtc catatcatat agcatcgata gaattacatt ctattccaat ggagtatata | 180 |

```
acacaaaaag atttagaaaa atgttatata gttcataatg gtttgatatt acaatgctct    240
aaagataata atctaaatat gcatgttcat aatgtcatc gcgcttatca ttctgttaat    300
agttgcatat tatgtttcga tagatatccg aggcttagtt tggagggaaa atatcaacct   360
ttttatatat caacatctac atgcattact gctaatagta taatggaagt ttataatttg   420
aataaaaaag atgattatga atttattata aatccatctg aaacatttat aaaacatatt   480
aaagaaaaat caaatatatg tttaacggat aaacatggct ggattataat cgatggcaaa   540
aatgaaatta aatattaa                                                 558

<210> SEQ ID NO 25
<211> LENGTH: 531
<212> TYPE: DNA
<213> ORGANISM: Vaccinia virus

<400> SEQUENCE: 25
atggacgccg cgtttgttat tactccaatg ggtgtgttga ctataacaga tacattgtat    60
gatgatctcg atatctcaat catggacttt ataggaccat acattatagg taacataaaa   120
actgtccaaa tagatgtacg ggatataaaa tattccgaca tgcaaaaatg ctactttagc   180
tataagggta aaatagttcc tcaggattct aatgatttgg ctagattcaa catttatagc   240
atttgtgccg catacagatc aaaaaatacc atcatcatag catgcgacta tgatatcatg   300
ttagatatag aagataaaca tcagccattt tatctattcc catctattga tgtttttaac   360
gctacaatca tagaagcgta taacctgtat acagctggag attatcatct aatcatcaat   420
ccttcagata atctgaaaat gaaattgtcg tttaattctt cattctgcat atcagacggc   480
aatggatgga tcataattga tgggaaatgc aatagtaatt ttttatcata a             531

<210> SEQ ID NO 26
<211> LENGTH: 531
<212> TYPE: DNA
<213> ORGANISM: Vaccinia virus

<400> SEQUENCE: 26
atggacgccg cgtttgttat tactccaatg ggtgtgttga ctataacaga tacattgtat    60
gatgatctcg atatttcaat catggacttt ataggaccat acattatagg taacataaaa   120
actgtccaaa tagatgtacg ggatataaaa tattccgaca tgcaaaaatg ctactttagc   180
tataagggta aaatagttcc tcaggattct aatgatttgg ctagattcaa catttatagc   240
atttgtgccg catacagatc aaaaaatacc atcatcatag catgcgacta tgatatcatg   300
ttagatatag aagataaaca tcagccattt tatctattcc catctattga tgtttttaac   360
gctacaatca tagaagcgta taacctgtat acagctggag attatcatct aatcatcaat   420
ccttcagata atctgaaaat gaaattgtcg tttaattctt cattctgcat atcagacggc   480
aatggatgga ttataattga tgggaaatgc aatagtaatt ttttatcata a             531

<210> SEQ ID NO 27
<211> LENGTH: 531
<212> TYPE: DNA
<213> ORGANISM: Vaccinia virus

<400> SEQUENCE: 27
atggacgccg cgtttgttat tactccaatg ggtgtgttga ctataacaga tacattgtat    60
gatgatctcg atatctcaat catggacttt ataggaccat acattatagg taacataaaa   120
```

| | |
|---|---|
| actgtccaaa tagatgtacg ggatataaaa tattccgaca tgcaaaaatg ctactttagc | 180 |
| tataagggta aaatagttcc tcaggattct aatgatttgg ctagattcaa catttatagc | 240 |
| atttgtgccg catacagatc aaaaaatacc atcatcatag catgcgacta tgatatcatg | 300 |
| ttagatatag aagataaaca tcagccattt tatctattcc catctattga tgttttaac | 360 |
| gctacaatca tagaagcgta taacctgtat acagctggag attatcatct aatcatcaat | 420 |
| ccttcagata atctgaaaat gaaattgtcg tttaattctt cattctgcat atcagacggc | 480 |
| aatggatgga tcataattga tgggaaatgc aatagtaatt ttttatcata a | 531 |

<210> SEQ ID NO 28
<211> LENGTH: 531
<212> TYPE: DNA
<213> ORGANISM: Vaccinia virus

<400> SEQUENCE: 28

| | |
|---|---|
| atggacgccg cgtttgttat tactccaatg ggtgtgttga ctataacaga tacattgtat | 60 |
| gatgatctcg atatctcaat catggacttt ataggaccat acattatagg taacataaaa | 120 |
| actgtccaaa tagatgtacg ggatataaaa tattccgaca tgcaaaaatg ctactttagc | 180 |
| tataagggta aaatagttcc tcaggattct aatgatttgg ctagattcaa catttatagc | 240 |
| atttgtgccg catacagatc aaaaaatacc atcatcatag catgcgacta tgatatcatg | 300 |
| ttagatatag aagataaaca tcagccattt tatctattcc catctattga tgttttaac | 360 |
| gctacaatca tagaagcgta taacctgtat acagctggag attatcatct aatcatcaat | 420 |
| ccttcagata atctgaaaat gaaattgtcg tttaattctt cattctgcat atcagacggc | 480 |
| aatggatgga tcataattga tgggaaatgc aatagtaatt ttttatcata a | 531 |

<210> SEQ ID NO 29
<211> LENGTH: 531
<212> TYPE: DNA
<213> ORGANISM: Vaccinia virus

<400> SEQUENCE: 29

| | |
|---|---|
| atggacgccg cgtttgttat tactccaatg ggtgtgttga ctataacaga tacattgtat | 60 |
| gatgatctcg atatctcaat catggacttt ataggaccat acattatagg taacataaaa | 120 |
| actgtccaaa tagatgtacg ggatataaaa tattccgaca tgcaaaaatg ctactttagc | 180 |
| tataagggta aaatagttcc tcaggattct aatgatttgg ctagattcaa catttatagc | 240 |
| atttgtgccg catacagatc aaaaaatacc atcatcatag catgcgacta tgatatcatg | 300 |
| ttagatatag aagataaaca tcagccattt tatctattcc catctattga tgttttaac | 360 |
| gctacaatca tagaagcgta taacctgtat acagctggag attatcatct aatcatcaat | 420 |
| ccttcagata atctgaaaat gaaattgttg tttaattctt cattctgcat atcagacggc | 480 |
| aatggatgga tcataattga tgggaaatgc aatagtaatt ttttatcata a | 531 |

<210> SEQ ID NO 30
<211> LENGTH: 540
<212> TYPE: DNA
<213> ORGANISM: Yaba-like disease virus

<400> SEQUENCE: 30

| | |
|---|---|
| atggaaatcg ccggttataa ttttataatt acttcatttg gagtaataaa aatacatagt | 60 |
| gtaaatcatt ttaagactgt atgtgaggat ttaggcatcg ttattgttga ctatataggt | 120 |
| gaatacgcaa tagcgacgtt agaagttcaa gaaataaatg taaaccttat taaccaaaat | 180 |

```
gatatatacg attgttacgt agcgtgtaat ggttttatag taaactgttc taagttaaat      240
aatgttccgt ttcccgtaac acaggtatat tatgcatttc ttacaaaaaa caaaatatta      300
ttatgttgcg ataaatatcc aaaactatca ataaacaata aaatacagcc attttacatt      360
tcttcttcca tttacatatt agaatcaaaa atattagaag ttcataactt atataataaa      420
ggagattatc actttataat taatccttcg accgattttt taatgttttt aggaaaaatg      480
gttaactttt gttaactga caaaaatggg tggattatag tcgatgtaaa agtgaaataa       540
```

<210> SEQ ID NO 31
<211> LENGTH: 579
<212> TYPE: DNA
<213> ORGANISM: Yaba monkey tumor virus

<400> SEQUENCE: 31

```
atgaaaagtt atagtgtgtt tatccacaat acgattgaaa acatgtataa tgtcgttatt      60
acttcatttg gagtaataaa tatatacggt tttgaacatt taaaaaccgt atgtgaagat     120
ttaggtattg ttgtttttga ctttgtagga gagtacgcca tcgcaacatt aaacgctcaa     180
gaaataagcg taaaccttat tacacaagat gatataaacg actgttatat agcatgtaac     240
ggttttatag taaaatgttc tgagtataac aaggttccgt ttcccgtaat acagatatat     300
tgtgcttttc ttacaaagag caaaatttta ttatgttgtg attataccc aaaactgttt      360 gtggataaca tgttacaacc gttttatatt tctttctcta tttgtatatt ggaatcacga     420 gtattgagg tttataattt ataataag ggtgactatt atcttataat caatccttca        480
attgattttt taacattttt ggtaaaaacc gttagcttct gtttaactga caggaacgga     540
tgggttataa tcgacgcaaa aagtgaaata atacattag                            579
```

<210> SEQ ID NO 32
<211> LENGTH: 184
<212> TYPE: PRT
<213> ORGANISM: Bovine papular stomatitis virus

<400> SEQUENCE: 32

Met Thr Asn Gly Asn Met Ser Cys Leu Gln Ile Leu Thr Pro Phe Gly
1               5                   10                  15

Leu Ile Phe Ala Pro Asp Asp Val Arg Leu Arg Glu Ile Ala Leu Glu
            20                  25                  30

Leu Gly Ile Thr Tyr Val Ser Arg Ala Phe Gly Asp Met Leu Tyr Gly
        35                  40                  45

Glu Met Ser Phe Thr Ser Leu Pro Met Asn Glu Val Pro Ala Cys Val
    50                  55                  60

Ser Asp Cys Tyr Leu Ala Val Asn Gly Asn Leu Ile Pro Cys Thr Glu
65                  70                  75                  80

Ser Phe Arg Leu Arg Ile Pro Met Asp Gly Val Lys Ala Ala Tyr Arg
                85                  90                  95

Thr Gly Thr Gly Lys Thr Ile Leu Cys Gly Pro Glu Phe Asn Val Val
            100                 105                 110

Asn Pro Ser Gly Phe Arg Pro Ala Leu Arg Leu Arg Glu Leu Ser His
        115                 120                 125

Val Ala Ala His Thr Glu Ile Leu Glu Leu Tyr Ser Glu Ser Gly Asn
    130                 135                 140

Tyr Glu Phe Ile Met Gly Pro Ser Ala Arg Phe Met Thr Ser Leu Met
145                 150                 155                 160

```
Ala Lys Glu Ser Val Cys Leu Phe Gly Ser Gly Trp Cys Val Val Asp
                165                 170                 175

Leu Arg Arg Ile Ser Phe Thr Pro
            180
```

<210> SEQ ID NO 33
<211> LENGTH: 181
<212> TYPE: PRT
<213> ORGANISM: Deerpox virus

<400> SEQUENCE: 33

```
Met Glu Glu Asp Phe Thr Thr Leu Leu Thr Val Leu Gly Thr Met Arg
1               5                   10                  15

Ile Glu Asn Lys Asn Leu Ile Lys Thr Tyr Asp Asp Leu Gly Ile Asn
                20                  25                  30

Ile Val Asp Asp Phe Gly Pro Tyr Lys Leu Ala Ser Leu Glu Ile Ser
            35                  40                  45

Leu Val Ser Ser Glu Leu Leu Lys Thr Tyr Asp Leu Gln Asp Cys Tyr
    50                  55                  60

Ile Ala His Asn Gly Ile Val Leu His Cys Ser Ser Asp Asn Lys Leu
65                  70                  75                  80

Asn Ile Pro Val Tyr Lys Val Tyr Ser Val Tyr Met Ser Lys Lys Ser
                85                  90                  95

Ile Ile Ile Cys Phe Asp Glu Cys Pro Lys Leu Phe Ile Asp Gly Lys
            100                 105                 110

Ser Gln Pro Phe Tyr Ile Leu Ser Ser Leu Met Met Asp Ala His
        115                 120                 125

Ile Ile Glu Val Tyr Asn Leu Tyr Asp Glu Gly Asp Tyr His Ile Ile
    130                 135                 140

Leu Asn Pro Ser Lys Asn Phe Leu Lys Tyr Ile Ser Arg Phe Tyr
145                 150                 155                 160

Leu Cys Leu Ile Asp Lys Asn Gly Trp Ala Ile Ala Asp Gly Lys Val
                165                 170                 175

Lys Leu Asn Ile Asn
            180
```

<210> SEQ ID NO 34
<211> LENGTH: 191
<212> TYPE: PRT
<213> ORGANISM: lumpy skin disease virus

<400> SEQUENCE: 34

```
Met Asp Phe Asp Phe Ile Phe Asp Lys Asp Glu Asp Ile Tyr Thr
1               5                   10                  15

Leu Ile Thr Thr Leu Gly Val Leu Lys Ile Lys Lys Lys Glu Ile Ser
                20                  25                  30

Lys Val Cys Ser Glu Leu Gly Ile Asn Leu Ile Glu Thr Leu Gly Pro
            35                  40                  45

Tyr Asn Val Val Ser Leu Asn Ile His Pro Phe Pro Asn Asn Phe Ile
    50                  55                  60

Glu Gln Ser Asn Leu Ile Asn Cys Tyr Ile Ser Tyr Asn Gly Thr Leu
65                  70                  75                  80

Phe His Cys Ser Lys Asp Glu Arg Leu Ser Ile Pro Ile Asn Gly Leu
                85                  90                  95

Tyr Arg Gly Phe Tyr Ser Asn Asn Ser Phe Ile Phe Ser Phe Asp Lys
            100                 105                 110
```

```
Glu Asn Tyr Gly Lys Leu Leu Ile Asp Glu Lys Glu Gln Tyr Phe Tyr
            115                 120                 125

Leu Gly Thr Ala Tyr Asp Ile Val Asn Ser Asn Ile Ile Glu Val Tyr
        130                 135                 140

Asn Leu Tyr Arg Lys Gly Asp Tyr Asn Phe Ile Ile Asn Pro Ser Asp
145                 150                 155                 160

Asn Phe Leu Glu Met Ile Ala Asn Gln Ser Lys Met Cys Leu Thr Asp
                165                 170                 175

Lys Ser Gly Trp Cys Ile Val Asp Ile Lys Asn Glu Ile Glu Tyr
            180                 185                 190

<210> SEQ ID NO 35
<211> LENGTH: 233
<212> TYPE: PRT
<213> ORGANISM: Molluscum contagiosum virus

<400> SEQUENCE: 35

Met Gly Pro Gly Gly Phe Pro Val Ile Thr Pro Leu Gly Arg Met His
1               5                   10                  15

Leu Arg Ala Asp Met Arg Thr Arg Val Met Cys Val Asp Phe Gly Val
            20                  25                  30

Thr Met Asp Thr Leu Arg Val Leu Gly Pro Tyr Val Val Met Val Pro
        35                  40                  45

Met Leu Glu Pro Ala Ser Ala Ser Leu Leu Ala Pro Arg Ala Leu Arg
    50                  55                  60

Asp Cys Tyr Val Ala Ala His Gly Val Leu Leu His Cys Ser Glu Leu
65                  70                  75                  80

Ala Tyr Leu Cys Ala Pro Met Thr Arg Ile Phe Ala Val Phe Arg Ala
                85                  90                  95

Arg Arg Arg Tyr Val Leu Cys Cys Asp Asp Tyr Asp Val Leu Arg Thr
            100                 105                 110

His Val Gly Gly Ser Ala Phe Ser Val Arg Arg Phe Thr Asp Ala Asp
        115                 120                 125

Phe Glu Arg Val Arg Val Leu Glu Leu Tyr Asn Tyr Asn Tyr Cys Gly
    130                 135                 140

Glu Tyr Gln Leu Val Leu Leu Pro Ser Val Arg Leu Leu Arg Gln Leu
145                 150                 155                 160

Gln Ser Cys Ala Thr Tyr Cys Leu Asp Asp Gly His Gly Trp Leu Ala
                165                 170                 175

Val Asp Ala Cys Glu Cys Pro Leu Ser Arg Phe Arg Phe Ala Leu Pro
            180                 185                 190

Ser Ser Pro Arg Ala Asn Ala Pro Ala Thr Pro Ala Ala Trp
        195                 200                 205

Pro Leu Glu Arg Ser Gln Thr Pro Ala Glu Thr Leu Pro Pro Ala
    210                 215                 220

Arg Pro Leu Glu Pro Pro Lys Leu Lys
225                 230

<210> SEQ ID NO 36
<211> LENGTH: 179
<212> TYPE: PRT
<213> ORGANISM: Myxoma virus

<400> SEQUENCE: 36

Met Asp Ala Asp Arg Ile Thr Cys Val Thr Ala Leu Gly Val Leu Tyr
1               5                   10                  15
```

```
Ile Arg His Asp Glu Ile Asp Thr Val Arg Ser Glu Leu Gly Ile Thr
             20                  25                  30

Phe Ile Gly Asp Val Gly Pro Tyr Arg Val Ala Thr Leu Asn Ile Cys
         35                  40                  45

Pro Val Ala Leu Asp Asp Val Tyr Gln Arg Gly Val Thr Asn Cys Tyr
     50                  55                  60

Ile Val Ser Asp Gly Arg Ile Thr Arg Cys Ser Asn Gln Tyr Arg Leu
 65                  70                  75                  80

Thr Phe Pro Ile His Lys Val Tyr Thr Val Tyr Lys Ser Ile Asn Ser
                 85                  90                  95

Phe Met Leu Cys Phe Asp Lys Cys Phe Lys Leu Arg Ile Asp Asn Asn
             100                 105                 110

Pro Gln Asp Phe Phe Ile Thr Ser Ser Ile Ala Ile Gln Asp Ala Arg
         115                 120                 125

Val Leu Glu Val Tyr Asn Leu Tyr Lys Lys Gly Asp Tyr His Leu Ile
     130                 135                 140

Leu Asn Pro Ser Asp Ala Phe Leu Asn Gly Leu Val Lys Lys Tyr Asn
145                 150                 155                 160

Val Cys Leu Ser Ser Asn Thr Gly Trp Val Ile Ala Asp Gly Lys Ser
                 165                 170                 175

Glu Ile Glu

<210> SEQ ID NO 37
<211> LENGTH: 179
<212> TYPE: PRT
<213> ORGANISM: Orf virus

<400> SEQUENCE: 37

Met Ser Arg Leu Gln Ile Leu Thr Ser Phe Gly Gln Ile Phe Ala Pro
  1               5                  10                  15

Asp Glu Ala Arg Leu Arg Glu Ile Ala Arg Asp Leu Gly Ile Cys Thr
             20                  25                  30

Ile Lys Arg Ala Phe Gly Asp Met Leu Tyr Gly Phe Ile Asp Phe Asp
         35                  40                  45

Pro Val Pro Leu Thr Gln Val Asn Met Leu Met Ser Asn Cys Tyr Phe
     50                  55                  60

Ala Val Asn Gly Asn Leu Leu Pro Cys Thr Glu Asp Phe Arg Leu Arg
 65                  70                  75                  80

Leu Pro Ala Thr Glu Ile Ser Ala Ala Tyr Leu Thr Arg Thr Gly Arg
                 85                  90                  95

Thr Ile Leu Cys Gly Lys Asp Phe Asn Ile Val Ala Pro Ser Gly Phe
             100                 105                 110

Lys Pro Ser Met Arg Leu Arg Asp Leu Ser His Val Ser Ala Leu Val
         115                 120                 125

Glu Ile Leu Glu Val Tyr Asp Glu Ser Gly Glu Tyr Gln Phe Val Leu
     130                 135                 140

Gly Pro Ser Ala Gln Phe Met Leu Arg Leu Met Glu Lys Glu Asn Val
145                 150                 155                 160

Cys Leu Phe Gly Ser Gly Trp Cys Ile Val Asp Leu Arg Lys Leu Asp
                 165                 170                 175

Val Pro Ile

<210> SEQ ID NO 38
<211> LENGTH: 191
<212> TYPE: PRT
```

<213> ORGANISM: sheeppox virus

<400> SEQUENCE: 38

Met Asp Phe Asp Phe Ile Phe Asn Lys Asp Glu Asp Ile Tyr Thr
1               5                   10                  15

Leu Ile Thr Thr Leu Gly Val Leu Lys Ile Lys Lys Glu Ile Ser
            20                  25                  30

Lys Val Cys Ser Glu Leu Asp Ile Asn Phe Ile Glu Thr Leu Gly Pro
        35                  40                  45

Tyr Asn Val Val Ser Leu Asn Ile His Pro Phe Pro Asn Asn Phe Ile
    50                  55                  60

Glu Gln Ser Asn Leu Ile Asn Cys Tyr Ile Ser Tyr Asn Gly Arg Leu
65                  70                  75                  80

Phe His Cys Ser Lys Asp Glu Arg Leu Ser Ile Pro Ile Asn Gly Leu
                85                  90                  95

Tyr Arg Gly Phe Tyr Ser Asn Asn Ser Phe Ile Phe Ser Phe Asp Lys
            100                 105                 110

Glu Asn Tyr Gly Lys Leu Leu Ile Asp Glu Lys Lys Gln Tyr Phe Tyr
        115                 120                 125

Leu Gly Thr Ala Tyr Asp Ile Val Asn Ser Asn Ile Ile Glu Val Tyr
    130                 135                 140

Asn Leu Tyr Arg Lys Gly Asp Tyr Asn Phe Ile Ser Pro Ser Asp
145                 150                 155                 160

Asn Phe Leu Lys Met Ile Ser Asn Gln Ser Lys Met Cys Leu Thr Asp
                165                 170                 175

Lys Ser Gly Trp Cys Ile Val Asp Ile Lys Asn Glu Ile Glu Tyr
            180                 185                 190

<210> SEQ ID NO 39
<211> LENGTH: 185
<212> TYPE: PRT
<213> ORGANISM: Swinepox virus

<400> SEQUENCE: 39

Met Tyr Gln Trp Ile Val Asp Met Ala Thr Tyr Thr Phe Val Thr Ser
1               5                   10                  15

Leu Gly Val Leu Lys Leu Ser Glu Asp Asn Val Ser Arg Ser Phe Ser
            20                  25                  30

Asp Leu Gly Ile Thr Ile Ile Asp Arg Ile Gly Pro Tyr His Ile Ala
        35                  40                  45

Ser Ile Glu Leu His Ser Ile Pro Met Glu Tyr Ile Thr Gln Lys Asp
    50                  55                  60

Leu Glu Lys Cys Tyr Ile Val His Asn Gly Leu Ile Leu Gln Cys Ser
65                  70                  75                  80

Lys Asp Asn Asn Leu Asn Met His Val His Asn Val His Arg Ala Tyr
                85                  90                  95

His Ser Val Asn Ser Cys Ile Leu Cys Phe Asp Arg Tyr Pro Arg Leu
            100                 105                 110

Ser Leu Glu Gly Lys Tyr Gln Pro Phe Tyr Ile Ser Thr Ser Thr Cys
        115                 120                 125

Ile Thr Ala Asn Ser Ile Met Glu Val Tyr Asn Leu Asn Lys Lys Asp
    130                 135                 140

Asp Tyr Glu Phe Ile Ile Asn Pro Ser Glu Thr Phe Ile Lys His Ile
145                 150                 155                 160

Lys Glu Lys Ser Asn Ile Cys Leu Thr Asp Lys His Gly Trp Ile Ile

```
                  165                 170                 175

Ile Asp Gly Lys Asn Glu Ile Lys Tyr
            180                 185

<210> SEQ ID NO 40
<211> LENGTH: 176
<212> TYPE: PRT
<213> ORGANISM: Vaccinia virus

<400> SEQUENCE: 40

Met Asp Ala Ala Phe Val Ile Thr Pro Met Gly Val Leu Thr Ile Thr
1               5                   10                  15

Asp Thr Leu Tyr Asp Asp Leu Asp Ile Ser Ile Met Asp Phe Ile Gly
            20                  25                  30

Pro Tyr Ile Ile Gly Asn Ile Lys Thr Val Gln Ile Asp Val Arg Asp
        35                  40                  45

Ile Lys Tyr Ser Asp Met Gln Lys Cys Tyr Phe Ser Tyr Lys Gly Lys
    50                  55                  60

Ile Val Pro Gln Asp Ser Asn Asp Leu Ala Arg Phe Asn Ile Tyr Ser
65                  70                  75                  80

Ile Cys Ala Ala Tyr Arg Ser Lys Asn Thr Ile Ile Ala Cys Asp
                85                  90                  95

Tyr Asp Ile Met Leu Asp Ile Glu Asp Lys His Gln Pro Phe Tyr Leu
            100                 105                 110

Phe Pro Ser Ile Asp Val Phe Asn Ala Thr Ile Glu Ala Tyr Asn
        115                 120                 125

Leu Tyr Thr Ala Gly Asp Tyr His Leu Ile Ile Asn Pro Ser Asp Asn
    130                 135                 140

Leu Lys Met Lys Leu Ser Phe Asn Ser Ser Phe Cys Ile Ser Asp Gly
145                 150                 155                 160

Asn Gly Trp Ile Ile Ile Asp Gly Lys Cys Asn Ser Asn Phe Leu Ser
                165                 170                 175

<210> SEQ ID NO 41
<211> LENGTH: 60
<212> TYPE: PRT
<213> ORGANISM: Variola virus

<400> SEQUENCE: 41

Met Asp Thr Thr Phe Val Ile Thr Pro Met Gly Met Leu Thr Ile Thr
1               5                   10                  15

Asp Thr Leu Tyr Asp Asp Leu Asp Ile Ser Ile Met Asp Phe Ile Gly
            20                  25                  30

Pro Tyr Ile Ile Gly Asn Ile Lys Thr Val Gln Ile Asp Val Arg Asp
        35                  40                  45

Ile Lys Tyr Ser Asp Met Gln Lys Cys Tyr Phe Ser
    50                  55                  60

<210> SEQ ID NO 42
<211> LENGTH: 179
<212> TYPE: PRT
<213> ORGANISM: Yaba-like disease virus

<400> SEQUENCE: 42

Met Glu Ile Ala Gly Tyr Asn Phe Ile Ile Thr Ser Phe Gly Val Ile
1               5                   10                  15

Lys Ile His Ser Val Asn His Phe Lys Thr Val Cys Glu Asp Leu Gly
            20                  25                  30
```

```
Ile Val Ile Val Asp Tyr Ile Gly Glu Tyr Ala Ile Ala Thr Leu Glu
            35                  40                  45

Val Gln Glu Ile Asn Val Asn Leu Ile Asn Gln Asn Asp Ile Tyr Asp
 50                  55                  60

Cys Tyr Val Ala Cys Asn Gly Phe Ile Val Asn Cys Ser Lys Leu Asn
 65                  70                  75                  80

Asn Val Pro Phe Pro Val Thr Gln Val Tyr Tyr Ala Phe Leu Thr Lys
                 85                  90                  95

Asn Lys Ile Leu Leu Cys Cys Asp Lys Tyr Pro Lys Leu Ser Ile Asn
            100                 105                 110

Asn Lys Ile Gln Pro Phe Tyr Ile Ser Ser Ile Tyr Ile Leu Glu
            115                 120                 125

Ser Lys Ile Leu Glu Val His Asn Leu Tyr Asn Lys Gly Asp Tyr His
    130                 135                 140

Phe Ile Ile Asn Pro Ser Thr Asp Phe Leu Met Phe Leu Gly Lys Met
145                 150                 155                 160

Val Asn Phe Cys Leu Thr Asp Lys Asn Gly Trp Ile Ile Val Asp Val
                165                 170                 175

Lys Val Lys

<210> SEQ ID NO 43
<211> LENGTH: 192
<212> TYPE: PRT
<213> ORGANISM: Yaba monkey tumor virus

<400> SEQUENCE: 43

Met Lys Ser Tyr Ser Val Phe Ile His Asn Thr Ile Glu Asn Met Tyr
 1               5                  10                  15

Asn Val Val Ile Thr Ser Phe Gly Val Ile Asn Ile Tyr Gly Phe Glu
                20                  25                  30

His Leu Lys Thr Val Cys Glu Asp Leu Gly Ile Val Val Phe Asp Phe
            35                  40                  45

Val Gly Glu Tyr Ala Ile Ala Thr Leu Asn Ala Gln Glu Ile Ser Val
 50                  55                  60

Asn Leu Ile Thr Gln Asp Asp Ile Asn Asp Cys Tyr Ile Ala Cys Asn
 65                  70                  75                  80

Gly Phe Ile Val Lys Cys Ser Glu Tyr Asn Lys Val Pro Phe Pro Val
                 85                  90                  95

Ile Gln Ile Tyr Cys Ala Phe Leu Thr Lys Ser Lys Ile Leu Leu Cys
            100                 105                 110

Cys Asp Tyr His Pro Lys Leu Phe Val Asp Asn Met Leu Gln Pro Phe
            115                 120                 125

Tyr Ile Ser Phe Ser Ile Cys Ile Leu Glu Ser Arg Val Leu Glu Val
    130                 135                 140

Tyr Asn Leu Tyr Asn Lys Gly Asp Tyr Leu Ile Ile Asn Pro Ser
145                 150                 155                 160

Ile Asp Phe Leu Thr Phe Leu Val Lys Thr Val Ser Phe Cys Leu Thr
                165                 170                 175

Asp Arg Asn Gly Trp Val Ile Asp Ala Lys Ser Glu Ile Ile His
            180                 185                 190

<210> SEQ ID NO 44
<211> LENGTH: 15
<212> TYPE: PRT
<213> ORGANISM: Variola virus
```

```
<400> SEQUENCE: 44

Tyr Asp Asp Leu Asp Ile Ser Ile Met Asp Phe Ile Gly Pro Tyr
1               5                   10                  15
```